(12) United States Patent
Morie et al.

(10) Patent No.: US 7,084,176 B2
(45) Date of Patent: Aug. 1, 2006

(54) N-ARYLPHENYLACETAMIDE DERIVATIVES AND MEDICINAL COMPOSITIONS CONTAINING THE SAME

(75) Inventors: Toshiya Morie, Matsubara (JP); Keiji Adachi, Amagasaki (JP); Kazumi Niidome, Takarazuka (JP); Katsuyoshi Kawashima, Kobe (JP); Isao Shimizu, Akashi (JP); Daisuke Ishii, Nishinomiya (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 324 days.

(21) Appl. No.: 10/480,377

(22) PCT Filed: Jun. 6, 2002

(86) PCT No.: PCT/JP02/05586

§ 371 (c)(1),
(2), (4) Date: Dec. 11, 2003

(87) PCT Pub. No.: WO02/100819

PCT Pub. Date: Dec. 19, 2002

(65) Prior Publication Data

US 2004/0248983 A1    Dec. 9, 2004

(30) Foreign Application Priority Data

Jun. 11, 2001   (JP) .............................. 2001-176252

(51) Int. Cl.
*A01N 37/12*    (2006.01)
*A01N 37/44*    (2006.01)

(52) U.S. Cl. .................. 514/563; 514/449; 514/618; 514/619; 514/450; 514/453; 514/459; 562/450; 564/86

(58) Field of Classification Search ................ 514/563, 514/449, 618, 619, 450, 453, 459; 562/450; 564/86
See application file for complete search history.

(56) References Cited

U.S. PATENT DOCUMENTS 5,013,759 A    5/1991   Berman et al.

FOREIGN PATENT DOCUMENTS

| EP | 0 282 127 | | 9/1988 |
|---|---|---|---|
| EP | 0 282 127 A2 | * | 9/1988 |
| EP | 0 462 933 | | 12/1991 |
| EP | 0 525 360 A2 | * | 2/1993 |
| EP | 525360 | | 2/1993 |
| EP | 721939 | | 7/1996 |
| GB | 2168975 | | 1/1986 |
| WO | 99/29674 | | 6/1999 |
| WO | 00/16756 | | 3/2000 |
| WO | WO 00/16756 | * | 3/2000 |
| WO | 01/23347 | | 4/2001 |

OTHER PUBLICATIONS

Michael J. Caterina et al., "The capsaicin receptor: a heat-activated ion channel in the pain pathway", Nature, 389, pp. 816-824, 1997.
Arpad Szallasi et al., "Vanilloid (Capsaicin) Receptors and Mechanisms", Pharmacol. Rev. 51, pp. 159-211, 1999.
Yuri Ikeda et al., "Involvement of vanilloid receptor VR1 and prostanoids in the acid-induced writhing responses of mice", Life Scienes, 69, pp. 2911-2919, 2001.
Stephen H. Buck et al., "The Neuropharmacology of Capsaicin: Review of Some Recent Obsevations", Pharmacol. Rev., 38, pp. 179-226, 1986.
John M. Janusz, et al., "Vanilloids. 1. Analogs of Capsaicin with Antinociceptive and Antiinflammatory Activity", J. Med. Chem., 36, pp. 2595-2604, 1993.

* cited by examiner

*Primary Examiner*—Johann Richter
*Assistant Examiner*—Chukwuma Nwaonicha
(74) *Attorney, Agent, or Firm*—Wenderoth, Lind & Ponack, L.L.P.

(57) ABSTRACT

N-Arylphenylacetamide derivatives represented by the following formula [I]:

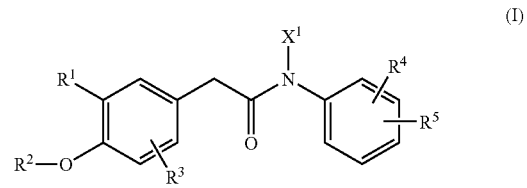

(wherein $R^1$ is $C_{1-6}$ alkoxy, etc.; $R^2$ is hydrogen, $-(CH_2)_m-N(R^6)(R^7)$ (m is an integer of from 1 to 4; $R^6$ is hydrogen, $C_{1-4}$ alkyl, etc., $R^7$ is hydrogen, etc.), etc.; $R^3$ is hydrogen, halogen, etc.; $R^4$ is $C_{6-10}$ alkyl, $-Y-R^8$ (Y is a single bond, $C_{1-6}$ alkylene, $C_{2-6}$ alkenylene, $C_{2-6}$ alkynylene, etc., $R^8$ is aryl, $C_{3-8}$ cycloalkyl, $C_{6-15}$ polycycloalkyl, etc.), etc.; $R^5$ is hydrogen, etc.; and $X^1$ is hydrogen), or pharmaceutically acceptable salts thereof or hydrates or solvates of the same, and a pharmaceutical composition containing the same. These compounds are useful as preventives and/or remedies giving no pain at the early stage of administration, which are efficacious in oral administration and have potent analgesic and antiinflammatory effects.

16 Claims, No Drawings

N-ARYLPHENYLACETAMIDE DERIVATIVES AND MEDICINAL COMPOSITIONS CONTAINING THE SAME

TECHNICAL FIELD

The present invention relates to an N-arylphenylacetamide derivative being useful as an agent for treatment of pain and inflammation, and a pharmaceutical composition containing the same.

BACKGROUND ART

Capsaicin (trans-8-methyl-N-vanillyl-6-nonenamide) is present in juices of *Capsicum* plants, and it has been commonly used as a spice, and further, it has been known to exhibit an analgesic effect and an antiinflammatory effect. Capsaicin has been considered to act on a specific receptor being present in primary afferent sensory nerves (C-fibers: capsaicin-sensitive nerves), whereby it causes a drastic pungency (pain) and further exhibits an analgesic effect and an antiinflammatory effect thereafter. Recently, said receptor has been cloned and named as vanilloid receptor subtype 1 (hereinafter, referred to as VR1) (cf., Nature, 389, 816 (1997)). VR1 has been considered from its amino acid sequence as an ion channel having six transmembrane domains and showing a high $Ca^{2+}$ permeability, and it is suggested that VR1 is possibly activated not only by capsaicin-like compounds but also by thermal stimuli or protons, and further that VR1 may possibly be involved with pain in various clinical conditions. When capsaicin acts on VR1 in primary afferent sensory nerves, a cation channel is opened, and the membrane is depolarized so that neuropeptides such as substance P are released to induce pain. Capsaicin, a pain inducing substance, is actually used in the treatment of painful disorders such as diabetic neuropathy and rheumatic arthritis. The reason for this paradoxical use of capsaicin has been considered that sensory nerves are insensitive (desensitized) to painful stimuli as a result of continuous VR1 cation channel opening after repeatedly application of capsaicin (cf., Pharmacol. Rev., 51, 159 (1999)).

At the moment, narcotic analgesics (morphine, etc.) and nonnarcotic analgesics (NSAIDs, etc.) are commonly used as an analgesic agent. However, the use of narcotic analgesics is strictly restricted, because of development of tolerance, dependency or serious side effects thereof. Further, nonnarcotic analgesics are not effective to severe pain, and it has been known that nonnarcotic analgesics are associated with significant rates of upper digestive disorders or liver disorders by prolonged administration thereof. Under the circumstances, it has been desired to develop an analgesic agent exhibiting a higher analgesic effect with few side effects. Moreover, since there is no effective analgesic agent for neuropathic pains such as pains caused by diabetic neuropathy, post herpetic neuralgia, trigeminal neuralgia, it has also been desired to develop a novel analgesic agent to treat them.

Capsaicin-like compounds acting on VR1 receptor (VR1 receptor agonists) have been considered to exhibit their effects based on a completely different action mechanism from the existing analgesic agents, i.e., desensitization of capsaicin-sensitive sensory nerve, and hence, the efficacy of such compounds has greatly been expected for the treatment of neuropathic pains for which the existing analgesic agents cannot be effective, or pains induced in various pathologic conditions such as rheumatic arthritis.

Since it is reported that capsazepin, which is an only-known VR1 receptor antagonist, exhibits a significant analgesic effect in an animal pain model (cf., Life Science, 69, 2911 (2001)), VR1 receptor antagonists may also be an agent for treatment of various pains.

The compounds with similar actions of capsaicin may be useful as an agent for treatment of diseases in which primary afferent sensory nerves (C-fibers) are concerned, such as essential pruritus, allergy or nonallergic rhinitis, frequent urination and urinary incontinence with overactive bladder, stroke, irritable bowel syndrome, respiratory disorders such as asthma and chronic obstructive pulmonary disease, dermatitis, mucositis, gastric and duodenal ulcers, inflammatory bowel diseases.

Further, since it has been reported that capsaicin exhibits an anti-obesity activity by promoting the hypersecretion of adrenalin (cf., Pharmacol. Rev., 38, 179 (1986)), capsaicin-like compounds will be useful as an agent for treatment of obesity.

As capsaicin analogous compounds having an analgesic activity, JP-A-63-295537 (=EP 0282127B, U.S. Pat. No. 5,099,030, U.S. Pat. No. 5,045,565) discloses beta-aminoethyl-substituted phenyl compounds, JP-A-4-230257 (=EP 0462933B) discloses N-benzyl-N'-phenyl- and -phenylalkyl-thiourea compounds, and WO 00/16756 discloses N-acylvanillinamide derivatives. In addition, J. Med. Chem., 36, 2595 (1993) discloses with respect to the analgesic effects of N-(4-hydroxy-3-methoxybenzyl)-4-pentyl-benzamide, but it is reported that this compound has no analgesic effect. The compounds disclosed in these patent publications and literatures are N-benzylamide derivatives or N-benzylthiourea derivatives, but the compounds of the formula (I) as described hereinafter are phenylacetamide derivatives, and therefore, these compounds are different in the chemical structures thereof.

It has been disclosed that the substituted phenylacetamide derivatives (in JP-A-62-48657 (=EP 206609B, U.S. Pat. No. 5,013,759)) and the N-arylalkylphenylacetamide compounds (in JP-A-5-320113 (=EP 0525360B, U.S. Pat. No. 5,242,944) and JP-A-8-283220 (=EP 0721939B, U.S. Pat. No. 5,670,546)) exhibit an analgesic effect. Furthermore, GB 2168975 discloses an aralkaneamide compound having an analgesic effect. However, these patent publications never specifically disclose the N-arylacetamide derivative of the formula (I) as described below.

WO 99/29674 discloses that the following anilides are compounds inhibiting the metabolism of retinoic acid.

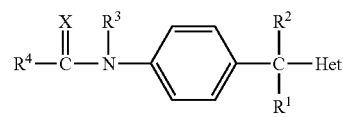

wherein X is O, etc., $R^1$ is hydrogen atom, a $C_{1-6}$ alkyl group, etc., $R^2$ is a hydrogen atom, a $C_{1-12}$ alkyl group, a $C_{2-8}$ alkenyl group, etc., $R^3$ is a hydrogen atom, a $C_{1-6}$ alkyl group, etc., $R^4$ is an aryl group, etc., Het is an unsaturated heterocyclic group selected from a pyrrolyl group, a pyrazolyl group, an imidazolyl group, a triazolyl group, a tetrazolyl group and a pyrimidinyl group, which may optionally be substituted by an amino, a mercapto, a $C_{1-6}$ alkyl, a $C_{1-6}$ alkylthio, or an aryl.

DISCLOSURE OF INVENTION

The present inventors have intensively studied, and have found that the N-arylphenylacetamide derivatives of the following formula (I) exhibit a potent analgesic effect, and hardly cause a pain in the early stage of administration, and further they are efficacious in oral administration, and finally they have accomplished the present invention.

An object of the present invention is to provide a novel N-arylphenylacetamide derivative being useful as an agent for treatment of pain and inflammation. Another object of the present invention is to provide a pharmaceutical composition containing said compound. These objects and other objects or advantages of the present invention may be apparent to any skilled persons in this art from the following disclosure.

The present invention provides an N-arylphenylacetamide derivative of the following formula (I), or a pharmaceutically acceptable salt thereof, or a hydrate or solvate thereof (hereinafter, referred to as "the present compound(s)"), a process for preparing the same, and a pharmaceutical composition containing the same.

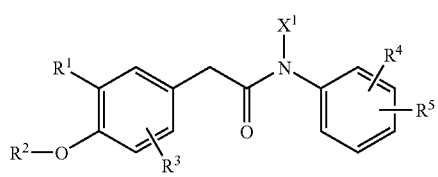
(I)

(wherein $R^1$ is a $C_{1-6}$ alkoxy group, a hydroxy group, a halogen atom, a nitro group, an amino group, a $C_{1-6}$ alkylamino group, a di-($C_{1-6}$ alkyl)-amino group, a $C_{1-6}$ alkylsulfonylamino group, or an arylsulfonylamino group, $R^2$ is a hydrogen atom, a $C_{1-6}$ alkylcarbonyl group, an arylcarbonyl group, —$(CH_2)_m$—$N(R^6)(R^7)$, —$(CH_2)_m OH$ or —$(CH_2)_q COOH$ (in which m is an integer of 2 to 4, q is an integer of 1 to 4, $R^6$ is a hydrogen atom, a $C_{1-3}$ alkyl group, a hydroxy-$C_{2-3}$ alkyl group, an amino-$C_{2-3}$ alkyl group, a formyl group, a $C_{1-3}$ alkylcarbonyl group, a $C_{1-4}$ alkoxycarbonyl group, an arylcarbonyl group, or an aryl-$C_{1-3}$ alkyloxycarbonyl group, $R^7$ is a hydrogen atom, a $C_{1-3}$ alkyl group, a hydroxy-$C_{2-3}$ alkyl group, or an amino-$C_{2-3}$ alkyl group), $R^3$ is a hydrogen atom, a halogen atom, a $C_{1-6}$ alkyl group, a $C_{1-4}$ alkoxy group, an aryl group, or a formyl group, $R^4$ is a $C_{6-10}$ alkyl group, a group of the following formula (A) or a group of the following formula (C), and the group of the formula (A) is a group of the formula:

—Y—$R^8$ (A)

[in which Y is a single bond, a $C_{1-3}$ alkylene group, a $C_{2-3}$ alkenylene group, a $C_{2-3}$ alkynylene group, —$CO(CH_2)_p$—, a $C_{2-3}$ alkenylenecarbonyl group, —O—, —O—$(CH_2)_2$—, —O—$(CH_2)_3$—, or —$CONH(CH_2)_p$—, and p is an integer of 0 to 3, $R^8$ is a monocyclic group or a polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a $C_{2-6}$ alkenyl, a $C_{2-6}$ alkynyl, a trifluoromethyl, a trifluoroethyl, an aryl, an aryl-$C_{1-6}$ alkyl, a $C_{1-6}$ alkoxy, a trifluoromethoxy, a $C_{3-7}$ cycloalkyloxy, an aryloxy, an aryl-$C_{1-3}$ alkyloxy, a $C_{1-6}$ alkylcarbonyl, a $C_{3-7}$ cycloalkylcarbonyl, a formyl, a nitro, an amino, a di-($C_{1-6}$ alkyl)amino, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl, an aryl-$C_{1-3}$ alkyloxycarbonyl, a carboxy and a sulfamoyl; a $C_{5-7}$ cycloalkenyl group which may optionally be substituted by 1 to 4 atoms or groups selected from a $C_{1-6}$ alkyl, a $C_{3-7}$ cycloalkyl, a halogen, a trifluoromethyl, a $C_{1-4}$ alkoxycarbonyl, an aryl, an aryl-$C_{1-6}$ alkyl, a $C_{1-3}$ alkoxy and a hydroxy; or a group of the formula (B):

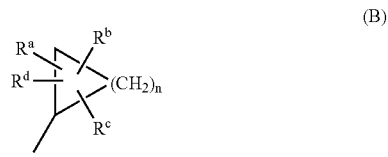
(B)

($R^a$, $R^b$, $R^c$ and $R^d$ are the same or different and each is a hydrogen atom, a $C_{1-6}$ alkyl group, a $C_{3-7}$ cycloalkyl group, a halogen atom, a trifluoromethyl group, a $C_{1-4}$ alkoxycarbonyl group, an aryl group, an aryl-$C_{1-6}$ alkyl group, a $C_{1-3}$ alkoxy group or a hydroxy group, or when $R^a$ and $R^b$ attach to the same carbon atom, then these groups may combine to form an oxo group or a thioxo group, or when $R^c$ and $R^d$ attach to the same carbon atom, then these groups may combine together with said carbon atom to form a spiro ring, or 2 or 3 groups selected from $R^a$, $R^b$ and $R^c$ may combine to form a $C_{6-15}$ polycycloalkyl group, and n is an integer of 1 to 6)], and the group of the formula (C) is a group of the formula:

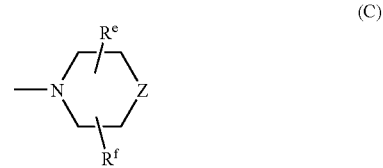
(C)

($R^e$ and $R^f$ are the same or different and each is a hydrogen atom, a $C_{1-6}$ alkyl group, a $C_{3-7}$ cycloalkyl group, a halogen atom, a trifluoromethyl group, a $C_{1-4}$ alkoxycarbonyl group, an aryl group, an aryl-$C_{1-6}$ alkyl group, a $C_{1-3}$ alkoxy group or a hydroxy group, or when $R^e$ and $R^f$ attach to the same carbon atom, then these groups may combine together with said carbon atom to form a spiro ring, and Z is a carbon atom, an oxygen atom or a sulfur atom), $R^5$ is a hydrogen atom, a halogen atom, a $C_{1-6}$ alkyl group, a trifluoromethyl group, a $C_{1-3}$ alkoxy group, a trifluoromethoxy group, a cyano group, a nitro group, an amino group, a hydroxy group, a carboxyl group, a $C_{1-6}$ alkylcarbonyloxymethyl group, or an aryl group, or $R^4$ and $R^5$ may combine together with the benzene ring to which they bond, and form a tetralone ring or an indole ring, which is substituted by one group selected from a $C_{1-8}$ alkyl, a $C_{1-8}$ alkenyl, an aryl-$C_{1-3}$ alkyl, a $C_{3-7}$ cycloalkyl-$C_{1-3}$ alkyl, an arylsulfonyl, a $C_{1-8}$ alkylidene, a $C_{1-8}$ alkenylidene, an aryl-$C_{1-3}$ alkylidene and a $C_{3-7}$ cycloalkyl-$C_{1-3}$ alkylidene, $X^1$ is a hydrogen atom, excluding the compound of the formula (I) wherein $R^4$ is —Y—$R^8$ at the para-position (in which Y is a $C_{1-3}$ alkylene group or a $C_{2-3}$ alkenylene group, and $R^8$ is an unsaturated heterocyclic group selected from a pyrrolyl group, a pyrazolyl group, an imidazolyl group, a triazolyl group, a tetrazolyl group, and a pyrimidyl group, which may optionally be substituted by an amino, a $C_{1-6}$ alkyl, an aryl or a $C_{1-3}$ alkylthio group).

The pharmaceutically acceptable salt of the compound of the formula (I) includes a pharmaceutically acceptable acid addition salt of the compound of the formula (I) having a group being capable of producing an acid addition salt within the structure thereof, or a pharmaceutically acceptable salt with a base of the compound of the formula (I) having a group being capable of producing a salt with a base within the structure thereof. Suitable acid addition salts are, for example, a salt with an inorganic acid such as hydrochloride, hydrobromide, hydroiodide, sulfate, perchlorate, phosphate, etc., and a salt with an organic acid such as oxalate, malonate, maleate, fumarate, lactate, malate, citrate, tartrate, benzoate, trifluoroacetate, acetate, methanesulfonate, p-toluenesulfonate, trifluoromethanesulfonate, etc., an amino acid salt such as glutamate, aspartate, etc. Suitable examples of a salt with a base are an alkali metal salt or an alkaline earth metal salt (e.g., sodium salt, potassium salt, calcium salt, etc.), a salt with an organic base (e.g., pyridine salt, triethylamine salt, etc.), a salt with an amino acid (e.g., a salt with lysine, arginine, etc.).

The compound of the formula (I) or a salt thereof may exist in the form of a hydrate and/or a solvate, and these hydrates and/or solvates are also included in the compounds of the present invention. Further, the compound of the formula (I) may optionally have one or more asymmetric carbon atoms, and may have isomerism. Therefore, the compound of the formula (I) may exist in the form of several stereoisomers, and these stereoisomers, a mixture thereof and racemic compounds thereof are also included in the compounds of the present invention.

The terms in the present specification are explained below.

In the present specification, the number of the carbon atoms is defined such as "$C_{1-6}$ alkylcarbonyl", and the number of the carbon atoms is applied to only the group or moiety immediately following thereto. Therefore, in the above case, since $C_{1-6}$ indicate only the number of carbon atom of the alkyl, and hence, "$C_1$ alkylcarbonyl" means acetyl.

The "halogen atom" is fluorine atom, chlorine atom, bromine atom, and iodine atom.

The "$C_{1-6}$ alkyl group" may be either a straight chain alkyl group or a branched chain alkyl group, for example, methyl, ethyl, propyl, isopropyl, butyl, isobutyl, sec-butyl, tert-butyl, pentyl, isopentyl, hexyl, and the equivalents thereof. The "$C_{6-10}$ alkyl group" may be either a straight chain alkyl group or a branched chain alkyl group, for example, octyl, nonyl, decyl, and the equivalents thereof.

The "$C_{2-6}$ alkenyl group" includes either a straight chain alkenyl group or a branched chain alkenyl group, having at least one double bond, for example, vinyl, allyl, 1-propenyl, isopropenyl, 1-, 2- or 3-butenyl, 2-, 3- or 4-pentenyl, 2-methyl-2-butenyl, 3-methyl-2-butenyl, 5-hexenyl, and the equivalents thereof.

The "$C_{2-6}$ alkynyl group" may be either a straight chain alkynyl group or a branched chain alkynyl group, having at least one triple bond, for example, ethynyl, 1- or 2-propynyl, 1-, 2- or 3-butynyl, 1-methyl-2-propynyl, and the equivalents thereof.

The "$C_{3-7}$ cycloalkyl group" is, for example, cyclopropyl, cyclobutyl, cyclopentyl, cyclohexyl, cycloheptyl, and the equivalents thereof.

The "$C_{5-7}$ cycloalkenyl group" is, for example, cyclopenten-1-yl, cyclohexen-1-yl, cyclohepten-5-yl, and the equivalents thereof.

The "aryl group" includes either an unsubstituted aryl group or a substituted aryl group, and the unsubstituted aryl group is a monocyclic or polycyclic group consisting of 5- or 6-membered aromatic ring, which contains 0 to 3 heteroatoms selected from N, O and S, and when it is a polycyclic group, then it has at least one aromatic ring. Examples of the unsubstituted aryl group are phenyl, naphthyl, fluorenyl, antholyl, biphenylyl, tetrahydronaphthyl, indanyl, phenanthryl, furyl, thienyl, pyrrolyl, imidazolyl, pyrazolyl, oxazolyl, thiazolyl, isoxazolyl, isothiazolyl, pyridyl, pyrazinyl, pyrimidinyl, pyridazinyl, indolyl, quinolyl, benzo[d]-1,3-dioxolanyl, benzo[b]-1,4-dioxolanyl, benzo[d]oxazolyl, benzo[b]-1,4-dioxepinyl, benzo[d]thiazolyl, benzo[b]thiophenyl, benzo[b]furanyl, benzimidazolyl, 1H-imidazo[4,5-b]-pyridyl, tetrahydroquinolyl, tetrahydro-1,8-naphthyridinyl, dibenzo[b,d]-furanyl, and the equivalents thereof.

The substituted aryl group is the above-mentioned unsubstituted aryl groups, which are substituted by 1 to 3 atoms or groups selected from a halogen, a $C_{1-6}$ alkyl, a $C_{3-7}$ cycloalkyl, a $C_{1-3}$ alkoxy, a trifluoromethyl, a trifluoromethoxy, a $C_{1-3}$ alkylthio, a cyano, a hydroxy, a carboxyl, a $C_{1-3}$ alkoxycarbonyl, a $C_{1-3}$ alkylcarbonyl, a formyl, a nitro, an amino, a $C_{1-3}$ alkylamino, a phenyl, a benzyl, and a benzyloxy, and examples of the substituted aryl group are 2-, 3- or 4-methylphenyl, 2-, 3- or 4-ethylphenyl, 2-, 3- or 4-isopropylphenyl, 2-, 3- or 4-tert-butylphenyl, 2-, 3- or 4-fluorophenyl, 2-, 3- or 4-chlorophenyl, 2-, 3- or 4-trifluoromethylphenyl, 2-, 3- or 4-methoxyphenyl, 2-, 3- or 4-difluoromethoxyphenyl, 2-, 3- or 4-trifluoromethoxyphenyl, 2-, 3- or 4-cyanophenyl, 2-, 3- or 4-hydroxyphenyl, 2-, 3- or 4-carboxyphenyl, 2-, 3- or 4-methoxycarbonylphenyl, 2-, 3- or 4-acetylphenyl, 2-, 3- or 4-formylphenyl, 2-, 3- or 4-nitrophenyl, 2-, 3- or 4-cyclohexylphenyl, 2-, 3- or 4-methylthiophenyl, 2-, 3- or 4-aminophenyl, 2-, 3- or 4-phenylphenyl, 2-, 3- or 4-benzylphenyl, 2-, 3- or 4-benzyloxyphenyl, 2,3-difluorophenyl, 2,4-difluorophenyl, 3,4-difluorophenyl, 3,5-difluorophenyl, 2,3-dichlorophenyl, 2,4-dichlorophenyl, 3,4-dichlorophenyl, 3-chloro-4-fluorophenyl, 2,3-dimethylphenyl, 2,4-dimethylphenyl, 3,4-dimethylphenyl, 2-fluoro-4-hydroxyphenyl, 4-hydroxy-3-methoxyphenyl, 4-hydroxy-3,5-dimethoxyphenyl, 2,4,6-trimethylphenyl, 2-aminopyridyl, 2-methylaminopyridyl, 5-methyl-pyrimidinyl, 1-methyl-2-pyrrolyl, 2-acetylamino-4-methyl-5-thiazolyl, 1-methylbenzimidazol-2-yl, 4-methyl-2-thienyl, 5-methyl-2-thienyl, 5-methyl-2-furyl, 5-methylbenzo[d]-1,3-dioxolanyl, 3,5-dimethyl-4-isoxazolyl, and the equivalents thereof.

The "$C_{1-3}$ alkylene group" may be either a straight chain alkylene group or a branched chain alkylene group, and examples thereof are —$CH_2$—, —$CH_2CH_2$—, —$CH_2CH_2CH_2$— and the equivalents thereof.

The "$C_{2-3}$ alkenylene group" may be either a straight chain alkenylene group or a branched chain alkenylene group, having at least one double bond, and examples thereof are —CH═CH—, —$CH_2$—CH═CH—, and the equivalents thereof.

Examples of the "$C_{2-3}$ alkynylene group" are —C≡C—, —$CH_2$—C≡C—, and —C≡C—$CH_2$—.

Examples of complexes consisting of the alkyl, cycloalkyl, alkenyl or alkynyl moiety, or the aryl, alkylene, alkenylene or alkynylene moiety, where the number of carbon atom of these moieties are defined, are ones wherein the above mentioned examples for each group are respectively applied to the relevant moiety. For example, examples of the $C_{1-6}$ alkoxy group are methoxy, ethoxy, propoxy, isopropoxy, butoxy, isobutoxy, tert-butoxy, pentyloxy, isopentyloxy, hexyloxy, and the equivalents thereof.

The group of the formula (B):

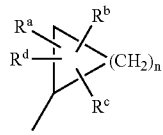

is, for example, an optionally substituted $C_{3-8}$ cycloalkyl group, an optionally substituted $C_{6-15}$ polycycloalkyl group and an optionally substituted spiro ring. The unsubstituted $C_{3-8}$ cycloalkyl group is, for example, a cyclopentyl group, a cyclohexyl group, a cycloheptyl group. The substituted $C_{3-8}$ cycloalkyl group is, for example, a cyclopentyl group, a cyclohexyl group, or a cycloheptyl group, which is substituted by 1 to 4 atoms or groups selected from a methyl, an ethyl, a propyl, an isopropyl, a tert-butyl, a fluorine, a trifluoromethyl, a methoxycarbonyl, a phenyl, a methoxy and a hydroxy; a 3-oxocyclopentyl group; a 3-oxocyclohexyl group; a 3-oxocycloheptyl group, and the equivalents thereof.

The "$C_{6-15}$ polycycloalkyl group" means "groups derived from a $C_{6-15}$ condensed polycyclic saturated hydrocarbons" and "groups derived from a $C_{6-15}$ cross-linked saturated hydrocarbons". Examples of the unsubstituted $C_{6-15}$ polycycloalkyl group are as described below, and the equivalents thereof are also included therein.

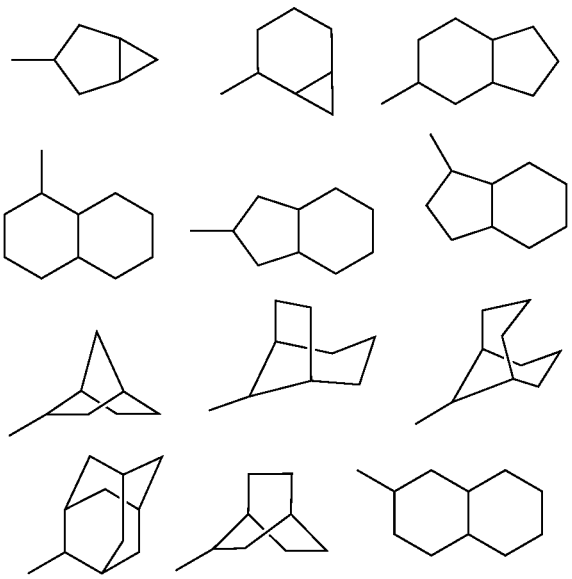

The spiro ring means a 3- to 7-membered one optionally having 0 to 2 heteroatoms selected from O, N and S. Examples of the unsubstituted spiro ring are as described below, and the equivalents thereof are also included therein.

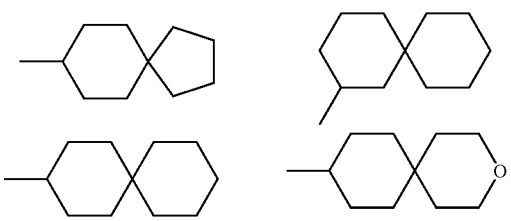

The "$C_{1-8}$ alkylidene" is, for example, a methylidene, an ethylidene, and the equivalents thereof.

Examples of the group of the following formula (C):

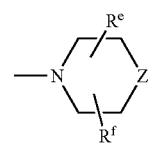

are as described below, and the equivalents thereof are also included therein.

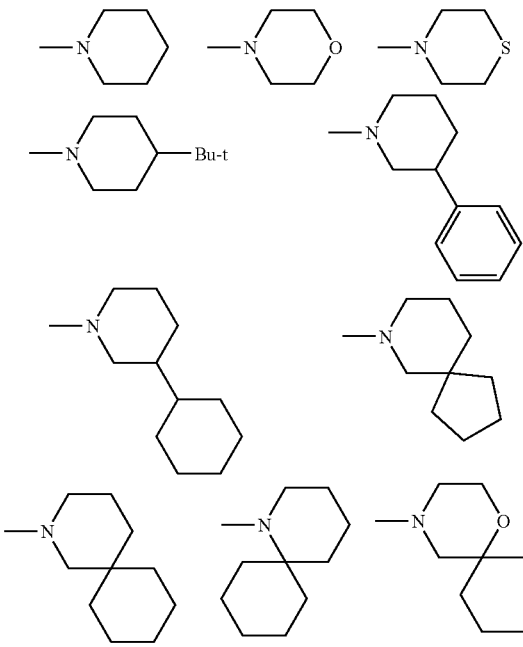

The preferable compounds of the present invention are N-arylphenylacetamide derivatives of the formula (I) or a pharmaceutically acceptable salt thereof, or a hydrate or solvate thereof, where $R^1$ is a $C_{1-4}$ alkoxy group, a hydroxy group, a halogen atom, a nitro group, an amino group, a $C_{1-6}$ alkylsulfonylamino group, or an arylsulfonylamino group, $R^2$ is a hydrogen atom, a $C_{1-6}$ alkylcarbonyl group, an arylcarbonyl group, —$(CH_2)_2$—$N(R^{61})(R^{71})$ (in which $R^{61}$ is a hydrogen atom, a $C_{1-3}$ alkyl group, a hydroxy-$C_{2-3}$ alkyl group, an amino-$C_{2-3}$ alkyl group, a formyl group, a $C_{1-3}$ alkylcarbonyl group, a $C_{1-4}$ alkoxycarbonyl group, an arylcarbonyl group or an aryl-$C_{1-3}$ alkyloxycarbonyl group, and $R^{71}$ is a hydrogen atom, a $C_{1-3}$ alkyl group, a hydroxy-$C_{2-3}$ alkyl group, or an amino-$C_{2-3}$alkyl group), $R^4$ is a $C_{6-10}$ alkyl group, the group of the above-mentioned formula (C), or the group of the above-mentioned formula (A) (provided that in the above-mentioned formula (A), Y is a single bond, a $C_{1-3}$ alkylene group, a $C_{2-3}$ alkenylene group, a $C_{2-3}$ alkynylene group, —CO(CH$_2$)$_{p'}$—, a $C_{2-3}$ alkenylenecarbonyl group, —O— or —O—(CH$_2$)$_2$—, p' is an integer of 0 to 2, $R^8$ is a monocyclic or polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, a trifluoroethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a formyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl, an aryl-$C_{1-3}$ alkyloxycarbonyl and a carboxyl; a $C_{5-7}$ cycloalkenyl group which may optionally be substituted by 1 to 4 atoms or groups selected from a $C_{1-6}$ alkyl, a $C_{3-7}$ cycloalkyl, a halogen, a trifluoromethyl, a $C_{1-4}$ alkoxycarbonyl, an aryl, an aryl-$C_{1-6}$ alkyl, a $C_{1-3}$ alkoxy and a hydroxy; or the group of the above-mentioned formula (B)), $R^3$, $R^5$ and $X^1$ are as defined above.

More preferable compounds are N-arylphenylacetamide derivatives of the formula (I) or a pharmaceutically acceptable salt thereof, or a hydrate or solvate thereof, wherein $R^4$ is located at the meta-position with respect to the group —N($X^1$)—, and $R^1$, $R^2$, $R^3$, $R^4$, $R^5$ and $X^1$ are as defined above.

Further preferable compounds are N-arylphenylacetamide derivatives of the following formula (I') or a pharmaceutically acceptable salt thereof, or a hydrate or solvate thereof.

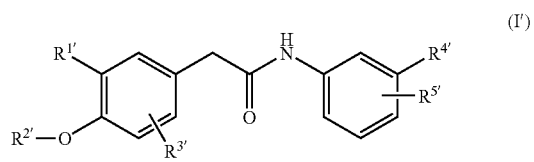

(I')

wherein $R^{1'}$ is a $C_{1-4}$ alkoxy group, a hydroxy group, a halogen atom, a nitro group, an amino group, a $C_{1-6}$ alkylsulfonylamino group or an arylsulfonylamino group, $R^{2'}$ is a hydrogen atom, a $C_{1-6}$ alkylcarbonyl group, an arylcarbonyl group or —(CH$_2$)$_2$—N($R^{6'}$)($R^{7'}$), in which $R^{6'}$ is a hydrogen atom, a $C_{1-3}$ alkyl group, a hydroxy-$C_{2-3}$ alkyl group, an amino-$C_{2-3}$ alkyl group, a formyl group, or an aryl-$C_{1-3}$ alkyloxycarbonyl group, and $R^{7'}$ is a hydrogen atom, a $C_{1-3}$ alkyl group, a hydroxy-$C_{2-3}$ alkyl group, or an amino-$C_{2-3}$ alkyl group, $R^{3'}$ is a hydrogen atom, a halogen atom, a $C_{1-4}$ alkyl group or an aryl group, $R^{4'}$ is a $C_{6-10}$ alkyl group, a group of the following formula (A'), or a group of the following formula (C'), in which the group of the formula (A') is a group of the formula:

—Y'—$R^{8'}$ (A')

[in which Y' is a single bond, —CH$_2$—, —(CH$_2$)$_2$—, —(CH$_2$)$_3$—, —CH=CH—, —C≡C—, —CO—, —COCH$_2$—, —CO(CH$_2$)$_2$—, —COCH=CH—, —O— or —O(CH$_2$)$_2$—, and $R^{8'}$ is a monocyclic or polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, a trifluoroethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl and a carboxy; a $C_{5-7}$ cycloalkenyl group which may optionally be substituted by 1 to 4 atoms or groups selected from a $C_{1-6}$ alkyl, a $C_{3-7}$ cycloalkyl, a fluorine, a trifluoromethyl, an aryl, a $C_{1-3}$ alkoxy and a hydroxy; or a group of the formula (B'):

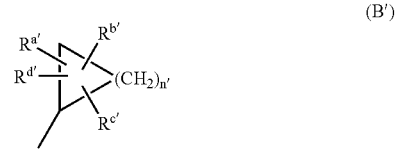

(B')

($R^{a'}$, $R^{b'}$, $R^{c'}$ and $R^{d'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group or a hydroxy group, or when $R^{a'}$ and $R^{b'}$ attach to the same carbon atom, then these groups may combine to form an oxo group, or when $R^{c'}$ and $R^{d'}$0 attach to the same carbon atom, then these groups may combine together with said carbon atom to form a spiro ring, or 2 or 3 groups selected from $R^{a'}$, $R^{b'}$ and $R^{c'}$ may combine to form a $C_{6-15}$ polycycloalkyl group, and n' is an integer of 1 to 5)], and the group of the formula (C') is a group of the formula:

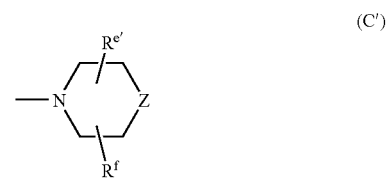

(C')

($R^{e'}$ and $R^{f'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group or a hydroxy group, or $R^{e'}$ and $R^{f'}$ attach to the same carbon atom, then these groups may combine together with said carbon atom to form a spiro ring, and Z is a carbon atom, an oxygen atom or a sulfur atom), $R^{5'}$ is a hydrogen atom, a halogen atom, a $C_{1-3}$ alkyl group, a trifluoromethyl group, a $C_{1-3}$ alkoxy group, a trifluoromethoxy group or an aryl group, or $R^{4'}$ and $R^{5'}$ may combine together with the benzene ring to which they bond, and form a tetralone ring or an indole ring, which is substituted by one group selected from a $C_{1-8}$ alkyl, an aryl-$C_{1-3}$ alkyl, a $C_{3-7}$ cycloalkyl-$C_{1-3}$ alkyl, an arylsulfonyl, a $C_{1-8}$ alkylidene, a $C_{1-8}$ alkenylidene, an aryl-$C_{1-3}$ alkylidene and a $C_{3-7}$ cycloalkyl-$C_{1-3}$ alkylidene.

The compound of the above formula (I') includes N-arylphenylacetamide derivatives of the following formula (Ia), or a pharmaceutically acceptable salt thereof, or a hydrate or solvate thereof.

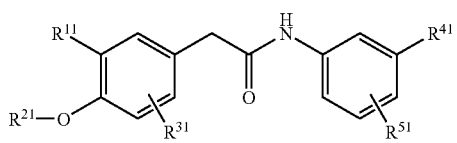

(Ia)

wherein $R^{11}$ is a $C_{1-4}$ alkoxy group, a hydroxy group, a halogen atom, a nitro group, an amino group, a $C_{1-6}$ alkylsulfonylamino group or an arylsulfonylamino group, $R^{21}$ is a hydrogen atom, a $C_{1-6}$ alkylcarbonyl group, an arylcarbonyl group or —$(CH_2)_2$—$N(R^{62})(R^{72})$, in which $R^{62}$ is a hydrogen atom, a $C_{1-3}$ alkyl group, a hydroxy-$C_{2-3}$ alkyl group, an amino-$C_{2-3}$ alkyl group, a formyl group, or an aryl-$C_{1-3}$ alkyloxycarbonyl group, $R^{72}$ is a hydrogen atom, a $C_{1-3}$ alkyl group, a hydroxy-$C_{2-3}$ alkyl group or an amino-$C_{2-3}$ alkyl group, $R^{31}$ is a hydrogen atom, a halogen atom, a $C_{1-4}$ alkyl group or an aryl group, $R^{41}$ is a $C_{6-10}$ alkyl group; a monocyclic group or a polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, a trifluoroethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl and carboxyl; a $C_{5-7}$ cycloalkenyl group which may optionally be substituted by 1 to 4 atoms or groups selected from a $C_{1-6}$ alkyl, a $C_{3-7}$ cycloalkyl, a fluorine, a trifluoromethyl, an aryl, a $C_{1-3}$ alkoxy and a hydroxy; a group of the formula (B'):

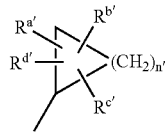

(B')

($R^{a'}$, $R^{b'}$, $R^{c'}$ and $R^{d'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group or a hydroxy group, or when $R^{a'}$ and $R^{b'}$ attach to the same carbon atom, then these groups may combine to form an oxo group, or when $R^{c'}$ and $R^{d'}$ attach to the same carbon atom, then these groups may combine together with said carbon atom to form a spiro ring, or 2 or 3 groups selected from $R^{a'}$, $R^{b'}$ and $R^{c'}$ may combine to form a $C_{6-15}$ polycycloalkyl group, and n' is an integer of 1 to 5); or a group of the formula (C'):

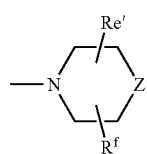

(C')

($R^{e'}$ and $R^{f'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group, or a hydroxy group, or when $R^{e'}$ and $R^{f'}$ attach to the same carbon atom, then these groups may combine together with said carbon atom to form a spiro ring, and Z is a carbon atom, an oxygen atom or a sulfur atom), $R^{51}$ is a hydrogen atom, a halogen atom, a $C_{1-3}$ alkyl group, a trifluoromethyl group, a $C_{1-3}$ alkoxy group, a trifluoromethoxy group or an aryl group.

Preferable compounds of the formula (Ia) are compounds of the formula (Ia), wherein $R^{41}$ is a monocyclic group or a polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, an aryl, an aryl-$C_{1-3}$ alkyl, a $C_{1-3}$ alkoxy, a trifluoromethoxy, a cyano, a $C_{1-3}$ alkylthio, a $C_{1-4}$ alkoxycarbonyl and a carboxyl; a $C_{5-7}$ cycloalkenyl group which may optionally be substituted by 1 to 4 atoms or groups selected from a $C_{1-6}$ alkyl, a $C_{3-7}$ cycloalkyl, a fluorine, a trifluoromethyl, an aryl and a $C_{1-3}$ alkoxy; a group of the formula (B"):

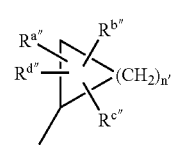

(B")

($R^{a''}$, $R^{b''}$, $R^{c''}$ and $R^{d''}$ are the same or different and each is a hydrogen atom, a $C_{1-6}$ alkyl group, a $C_{3-7}$ cycloalkyl group, a fluorine atom, a trifluoromethyl group, an aryl group, or a $C_{1-3}$ alkoxy group, or when $R^{a''}$ and $R^{b''}$ attach to the same carbon atom, then these group may combine to form an oxo group, or when $R^{c''}$ and $R^{d''}$ attach to the same carbon atom, then these groups may combine together with said carbon atom to form a spiro ring, or 2 or 3 groups selected from $R^{a''}$, $R^{b''}$ and $R^{c''}$ may combine to form a $C_{6-15}$ polycycloalkyl group, and n' is an integer of 1 to 5); or a group of the following formula (C"):

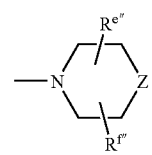

(C")

($R^{e''}$ and $R^{f''}$ are the same or different and each is a hydrogen atom, a $C_{1-6}$ alkyl group, a $C_{3-7}$ cycloalkyl group, a fluorine atom, a trifluoromethyl group, an aryl group or a $C_{1-3}$ alkoxy group, or when $R^{e''}$ and $R^{f''}$ attach to the same carbon atom, then these groups may combine together with said carbon atom to form a spiro ring, Z is a carbon atom, an oxygen atom, or a sulfur atom), $R^{11}$, $R^{21}$, $R^{31}$, $R^{51}$ are as defined above, or a pharmaceutically acceptable salt thereof, or a hydrate or solvent thereof.

More preferably compounds of the formula (Ia) are N-arylphenylacetamide derivatives of the formula (Ia) wherein $R^{11}$ is a methoxy group, $R^{21}$ is a hydrogen atom, an acetyl group, an ethylcarbonyl group, a propylcarbonyl group, an isopropylcarbonyl group, a butylcarbonyl group, a tert-butylcarbonyl group, a benzoyl group or a 2-aminoethyl group, $R^{31}$ is a hydrogen atom or a iodine atom, $R^{41}$ is a phenyl group, a naphthyl group, a thienyl group, a pyrrolyl group, a benzo[d]-1,3-dioxolanyl group, a benzo

[b]furanyl group, a benzo[b]thiophenyl group or a dibenzo[b,d]furanyl group, which may optionally be substituted by 1 to 3 atoms or groups selected from a fluorine, a chlorine, a methyl, an ethyl, a propyl, an isopropyl, a tert-butyl, a cyclopentyl, a cyclohexyl, a trifluoromethyl, a phenyl, a fluorophenyl, a chlorophenyl, a methylphenyl, a trifluoromethylphenyl, a trifluoromethoxyphenyl, a trifluoromethoxy, a methylthio, a methoxycarbonyl, an ethoxycarbonyl, a tert-butoxycarbonyl and a carboxyl; or a cyclohexenyl group, a cyclopentyl group, a cyclohexyl group, a cycloheptyl group, a bicyclo[2,2,2]octyl group, an adamantyl group, a 1-piperidinyl group, a 7-azaspiro[4,5]decan-7-yl group, a 2-azaspiro[5,5]-undecan-2-yl group, a 1-azaspiro[5,5]undecan-1-yl group, a 4-morpholinyl group, a 4-thiomorpholinyl group or a 1-oxa-4-azaspiro-[5,5]undecan-4-yl group, which may optionally be substituted by 1 to 4 atoms or groups selected from a methyl, an ethyl, a propyl, an isopropyl, a tert-butyl, a cyclopentyl, a cyclohexyl, a fluorine, a trifluoromethyl, a phenyl, a fluorophenyl, a chlorophenyl, a methylphenyl, a trifluoromethylphenyl and a trifluoromethoxyphenyl, $R^{51}$ is a hydrogen atom, a fluorine atom, a methyl group, a trifluoromethyl group, a methoxy group, a trifluoromethoxy group or a phenyl group, or a pharmaceutically acceptable salt thereof, or a hydrate or solvate thereof.

N-arylphenylacetamide derivatives of the following formula (Ib), or a pharmaceutically acceptable salt thereof, or a hydrate or solvate thereof may also be included within the compounds of the above formula (I').

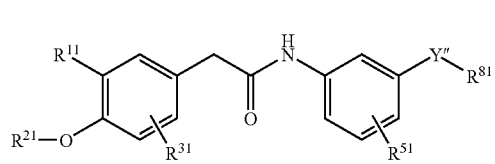

(Ib)

wherein $R^{11}$ is a $C_{1-4}$ alkoxy group, a hydroxy group, a halogen atom, a nitro group, an amino group, a $C_{1-6}$ alkylsulfonylamino group, or an arylsulfonylamino group, $R^{21}$ is a hydrogen atom, a $C_{1-6}$ alkylcarbonyl group, an arylcarbonyl group or —(CH$_2$)$_2$—N(R$^{62}$)(R$^{72}$), in which $R^{62}$ is a hydrogen atom, a $C_{1-3}$ alkyl group, a hydroxy-$C_{2-3}$ alkyl group, an amino-$C_{2-3}$ alkyl group, a formyl group, or an aryl-$C_{1-3}$ alkyloxycarbonyl group, and $R^{72}$ is a hydrogen atom, a $C_{1-3}$ alkyl group, a hydroxy-$C_{2-3}$ alkyl group or an amino-$C_{2-3}$ alkyl group, $R^{31}$ is a hydrogen atom, a halogen atom, a $C_{1-4}$ alkyl group or an aryl group, Y" is —CH$_2$—, —(CH$_2$)$_2$—, —(CH$_2$)$_3$—, —CH═CH—, —C≡C—, —CO—, —COCH$_2$—, —CO(CH$_2$)$_2$—, —COCH═CH—, —O— or —O(CH$_2$)$_2$—, $R^{81}$ is a monocyclic group or a polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl and a carboxyl; a $C_{5-7}$ cycloalkenyl group which may optionally be substituted by 1 to 4 atoms or groups selected from a $C_{1-6}$ alkyl, a $C_{3-7}$ cycloalkyl, a fluorine, a trifluoromethyl, an aryl, a $C_{1-3}$ alkoxy and a hydroxy; or a group of the formula (B'):

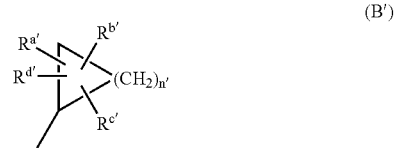

(B')

($R^{a'}$, $R^{b'}$, $R^{c'}$ and $R^{d'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group or a hydroxy group, or when $R^{a'}$ and $R^{b'}$ attach to the same carbon atom, then these groups may combine to form an oxo group, or when $R^{c'}$ and $R^{d'}$ attach to the same carbon atom, then these groups may combine together with said carbon atom to form a spiro ring, or 2 or 3 groups selected from $R^{a'}$, $R^{b'}$ and $R^{c'}$ may combine to form a $C_{6-15}$ polycycloalkyl group, and n' is an integer of 1 to 5), $R^{51}$ is a hydrogen atom, a halogen atom, a $C_{1-3}$ alkyl group, a trifluoromethyl group, a $C_{1-3}$ alkoxy group, a trifluoromethoxy group or an aryl group.

More preferable compounds of the formula (Ib) are compounds of the formula (Ib), wherein Y" is —(CH$_2$)$_2$—, —CH═CH—, —C≡C—, —O— or —O(CH$_2$)$_2$—, $R^{81}$ is a monocyclic group or a polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, an aryl, an aryl-$C_{1-3}$ alkyl, a $C_{1-3}$ alkoxy, a trifluoromethoxy, a cyano, a $C_{1-3}$ alkylthio, a $C_{1-4}$ alkoxycarbonyl and a carboxyl; a $C_{5-7}$ cycloalkenyl group which may optionally be substituted by 1 to 4 atoms or groups selected from a $C_{1-6}$ alkyl, a $C_{3-7}$ cycloalkyl, a fluorine, a trifluoromethyl, an aryl and a $C_{1-3}$ alkoxy; or a group of the formula (B"):

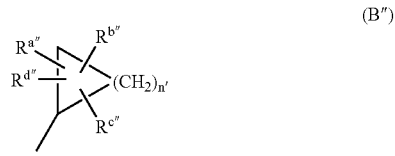

(B")

(wherein $R^{a''}$, $R^{b''}$, $R^{c''}$ and $R^{d''}$ are the same or different and each is a hydrogen atom, a $C_{1-6}$ alkyl group, a $C_{3-7}$ cycloalkyl group, a fluorine atom, a trifluoromethyl group, an aryl group or a $C_{1-3}$ alkoxy group, or when $R^{a''}$ and $R^{b''}$ attach to the same carbon atom, then these groups may combine to form an oxo group, or when $R^{c''}$ and $R^{d''}$ attach to the same carbon atom, then these groups may combine together with said carbon atom to form a spiro ring, or 2 or 3 groups selected from $R^{a''}$, $R^{b''}$ and $R^{c''}$ may combine to form a $C_{6-15}$ polycycloalkyl group, and n' is an integer of 1 to 5), and $R^{11}$, $R^{21}$, $R^{31}$, $R^{51}$ are as defined above, or a pharmaceutically acceptable salt thereof, or a hydrate or solvate thereof.

Further preferable compounds of the formula (Ib) are N-arylphenylacetamide derivatives of the formula (Ib), wherein $R^{11}$ is a methoxy group, $R^{21}$ is a hydrogen atom, an acetyl group, an ethylcarbonyl group, a propylcarbonyl group, an isopropylcarbonyl group, a butylcarbonyl group, a tert-butylcarbonyl group, a benzoyl group, a 2-aminoethyl group, $R^{31}$ is a hydrogen atom or a iodine atom, Y" is —(CH$_2$)$_2$—, —CH═CH—, —C≡C—, —O— or —O(CH$_2$)$_2$—, $R^{81}$ is a phenyl group, a naphthyl group or a thienyl group, which may optionally be substituted by 1 to 3 atoms or groups selected from a fluorine, a chlorine, a methyl, an ethyl, a propyl, an isopropyl, a tert-butyl, a cyclopentyl, a cyclohexyl, a trifluoromethyl, a phenyl, a fluorophenyl, a chlorophenyl, a methylphenyl, a trifluoromethylphenyl, a trifluoromethoxyphenyl, a trifluoromethoxy, a methylthio and a methoxycarbonyl; or a cyclohexenyl group, a cyclopentyl group, a cyclohexyl group, a cycloheptyl group, a bicyclo[2,2,2]octyl group or an adamantyl group, which may optionally be substituted by 1 to 4 atoms or groups selected from a methyl, an ethyl, a propyl, an isopropyl, a tert-butyl, a cyclopentyl, a cyclohexyl, a fluorine, a trifluoromethyl, a phenyl, a fluorophenyl, a chlorophenyl, a methylphenyl, a trifluoromethylphenyl and a trifluoromethoxyphenyl, $R^{51}$ is a hydrogen atom, a fluorine atom, a methyl group, a trifluoromethyl group, a methoxy group, a trifluoromethoxy group or a phenyl group, or a pharmaceutically acceptable salt thereof, or a hydrate or solvate thereof.

N-arylphenylacetamide derivatives of the following formula (Ic) or a pharmaceutically acceptable salt thereof, or a hydrate or solvate thereof may also be included within the compound of the formula (I').

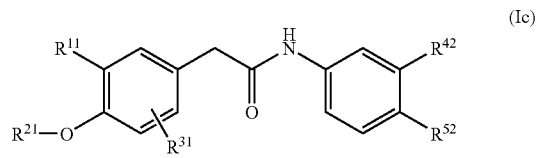

(Ic)

wherein $R^{11}$ is a $C_{1-4}$ alkoxy group, a hydroxy group, a halogen atom, a nitro group, an amino group, a $C_{1-6}$ alkylsulfonylamino group or an arylsulfonylamino group, $R^{21}$ is a hydrogen atom, a $C_{1-6}$ alkylcarbonyl group, an arylcarbonyl group or —(CH$_2$)$_2$—N($R^{62}$)($R^{72}$), in which $R^{62}$ is a hydrogen atom, a $C_{1-3}$ alkyl group, a hydroxy-$C_{2-3}$ alkyl group, an amino-$C_{2-3}$ alkyl group, a formyl group or an aryl-$C_{1-3}$ alkyloxycarbonyl group, and $R^{72}$ is a hydrogen atom, a $C_{1-3}$ alkyl group, a hydroxy-$C_{2-3}$ alkyl group or an amino-$C_{2-3}$ alkyl group, $R^{31}$ is a hydrogen atom, a halogen atom, a $C_{1-4}$ alkyl group or an aryl group, $R^{42}$ and $R^{52}$ may combine together with the benzene ring to which they bond to form a group selected from the following group:

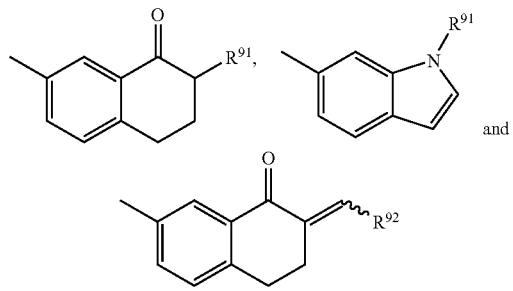

($R^{91}$ is a $C_{1-8}$ alkyl group; an aryl-$C_{1-3}$ alkyl group; a $C_{3-7}$ cycloalkyl-$C_{1-3}$ alkyl group; or an arylsulfonyl group, $R^{92}$ is a $C_{1-7}$ alkyl group; a $C_{1-7}$ alkenyl group; a phenyl group which may optionally be substituted by 1 to 3 atoms or groups selected from a halogen, a $C_{1-6}$ alkyl, a $C_{3-7}$ cycloalkyl, a trifluoromethyl, a trifluoroethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl and a carboxyl; an aryl-$C_{1-2}$ alkyl group; a $C_{3-7}$ cycloalkyl group; or a $C_{3-7}$ cycloalkyl-$C_{1-2}$ alkyl group).

More preferable compounds of the formula (Ic) are N-arylphenylacetamide derivatives of the formula (Ic), wherein $R^{11}$ is a methoxy group, $R^{21}$ is a hydrogen atom, an acetyl group, an ethylcarbonyl group, a propylcarbonyl group, an isopropylcarbonyl group, a butylcarbonyl group, a tert-butylcarbonyl group, a benzoyl group, a 2-aminoethyl group, $R^{31}$ is a hydrogen atom or a iodine atom, $R^{42}$ and $R^{52}$ may combine together with the benzene ring to which they bond to form a group selected from the following group:

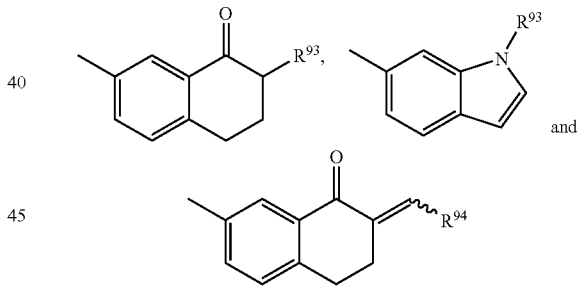

($R^{93}$ is a butyl group, a pentyl group, a hexyl group, an isobutyl group, a heptyl group, or a benzyl group, a phenethyl group or a phenylpropyl group, wherein the benzene ring moiety may optionally be substituted by 1 to 3 atoms or groups selected from a fluorine, a chlorine, a methyl, an ethyl, a propyl, an isopropyl, a tert-butyl, a cyclohexyl, a trifluoromethyl, a phenyl, a fluorophenyl, a chlorophenyl, a methylphenyl, a trifluoromethylphenyl, a trifluoromethoxyphenyl, a trifluoromethoxy, a methylthio and a methoxycarbonyl, and $R^{94}$ is an isopropyl group, or a phenyl group which may optionally be substituted by 1 to 3 atoms or groups selected from a fluorine, a chlorine, a methyl, an ethyl, a propyl, an isopropyl, a tert-butyl, a cyclohexyl, a trifluoromethyl, a phenyl, a fluorophenyl, a chlorophenyl, a methylphenyl, a trifluoromethylphenyl, a trifluoromethoxyphenyl, a trifluoromethoxy, a methylthio and a methoxycarbonyl), or a pharmaceutically acceptable salt thereof, or a hydrate or solvate thereof.

The compounds of the present invention may be grouped as follows, according to the characteristics of the chemical structure of the substituent $R^2$.

Compound of the formula (I) wherein $R^2$ is a hydrogen atom, and $R^1$, $R^3$, $R^4$, $R^5$ and $X^1$ are as defined above, or a pharmaceutically acceptable salt thereof, or a hydrate or solvate thereof;

Compound of the formula (I), wherein $R^2$ is a $C_{1-6}$ alkylcarbonyl group or an arylcarbonyl group, and $R^1$, $R^3$, $R^4$, $R^5$ and $X^1$ are as defined above, or a pharmaceutically acceptable salt thereof, or a hydrate or solvate thereof;

Compound of the formula (I) wherein $R^2$ is —$(CH_2)_m$—$N(R^6)(R^7)$, and $R^1$, $R^3$, $R^4$, $R^5$, m, $R^6$, $R^7$ and $X^1$ are as defined above, or a pharmaceutically acceptable salt thereof, or a hydrate or solvate thereof; and Compound of the formula (I) wherein $R^2$ is —$(CH_2)_m$OH or —$(CH_2)_q$COOH, and $R^1$, $R^3$, $R^4$, $R^5$, m, q and $X^1$ are as defined above, or a pharmaceutically acceptable salt thereof, or a hydrate or solvate thereof.

The N-arylphenylacetamide derivatives of the formulae (I'), (Ia), (Ib) and (Ic), or a pharmaceutically acceptable salt thereof, or a hydrate or solvate thereof may also be grouped according to the above classification.

Examples of the preferable compounds are the following compounds, or a pharmaceutically acceptable salt thereof, or a hydrate or solvate thereof.

N-(3-cyclohexylphenyl)-4-hydroxy-3-methoxyphenylacetamide (the compound of Example 1),
N-[3-(adamantan-2-yl)phenyl]-4-hydroxy-3-methoxyphenylacetamide (the compound of Example 3),
N-(3-cyclopentylphenyl)-4-hydroxy-3-methoxyphenylacetamide (the compound of Example 4),
N-[3-(cyclohexylmethyl)phenyl]-4-hydroxy-3-methoxyphenylacetamide (the compound of Example 5),
N-[3-(cyclohexen-1-yl)phenyl]-4-hydroxy-3-methoxyphenylacetamide (the compound of Example 9),
4-hydroxy-3-methoxy-N-[3-(2-phenylcyclohexan-1-yl)phenyl]-phenylacetamide (the compound of Example 11),
4-hydroxy-3-methoxy-N-[3-(4-methylcyclohexan-1-yl)phenyl]-phenylacetamide (the compound of Example 13),
N-[3-(4-tert-butylcyclohexan-1-yl)phenyl]-4-hydroxy-3-methoxyphenylacetamide (the compound of Example 20),
4-hydroxy-3-methoxy-N-(3-phenylphenyl)phenylacetamide (the compound of Example 35),
4-hydroxy-3-methoxy-N-[3-(2-phenylethynyl)phenyl]phenylacetamide (the compound of Example 36),
4-hydroxy-3-methoxy-N-[3-(2-phenylethyl)phenyl]phenylacetamide (the compound of Example 54),
4-hydroxy-3-methoxy-N-[3-[(Z)-2-phenylvinyl]phenyl]phenylacetamide (the compound of Example 56),
4-(2-aminoethoxy)-3-methoxy-N-[3-(2-phenylethyl)phenyl]-phenylacetamide (the compound of Example 60),
4-(2-aminoethoxy)-N-(3-cyclohexylphenyl)-3-methoxyphenylacetamide (the compound of Example 61),
4-(2-aminoethoxy)-N-[3-(4-tert-butylcyclohexan-1-yl)phenyl]-3-methoxyphenylacetamide (the compound of Example 62),
4-(2-aminoethoxy)-3-methoxy-N-(3-phenylphenyl)phenylacetamide (the compound of Example 63),
4-(2-aminoethoxy)-N-[3-(3-fluorophenyl)phenyl]-3-methoxyphenylacetamide (the compound of Example 66),
4-(2-aminoethoxy)-N-[3-(4-chlorophenyl)phenyl]-3-methoxyphenylacetamide (the compound of Example 67),
4-acetoxy-N-[3-(4-tert-butylcyclohexan-1-yl)phenyl]-3-methoxyphenylacetamide (the compound of Example 69),
4-benzoyloxy-N-[3-(4-tert-butylcyclohexan-1-yl)phenyl]-3-methoxyphenylacetamide (the compound of Example 70),
4-tert-butylcarbonyloxy-N-[3-(4-tert-butylcyclohexan-1-yl)-phenyl]-3-methoxyphenylacetamide (the compound of Example 71),
N-[3-(4-tert-butylcyclohexen-1-yl)phenyl]-4-hydroxy-3-methoxyphenylacetamide (the compound of Example 80),
4-hydroxy-3-methoxy-N-[3-(4-trifluoromethylcyclohexan-1-yl)-phenyl]phenylacetamide (the compound of Example 81),
4-hydroxy-3-methoxy-N-[3-(3-methylcyclohexan-1-yl)phenyl]-phenylacetamide (the compound of Example 83),
N-[3-(2,6-dimethylcyclohexan-1-yl)phenyl]-4-hydroxy-3-methoxyphenylacetamide (the compound of Example 84),
N-[3-(3,5-dimethylcyclohexan-1-yl)phenyl]-4-hydroxy-3-methoxyphenylacetamide (the compound of Example 85),
N-[3-(4-tert-butylpiperidin-1-yl)phenyl]-4-hydroxy-3-methoxyphenylacetamide (the compound of Example 86),
N-[3-(3-cyclohexylpiperidin-1-yl)phenyl]-4-hydroxy-3-methoxyphenylacetamide (the compound of Example 87),
N-[3-(3-methylpiperidin-1-yl)phenyl]-4-hydroxy-3-methoxyphenylacetamide (the compound of Example 88),
N-[3-(4-tert-butylcyclohexan-1-yl)phenyl]-4-hydroxy-5-iodo-3-methoxyphenylacetamide (the compound of Example 98),
4-hydroxy-3-methoxy-N-[3-(2-chlorothiophen-5-yl)phenyl]-phenylacetamide (the compound of Example 100),
4-hydroxy-3-methoxy-N-[3-(1-tert-butoxycarbonylpyrrol-2-yl)-phenyl]phenylacetamide (the compound of Example 101),
4-hydroxy-3-methoxy-N-[3-(2-cyclohexylethyl)phenyl]phenylacetamide (the compound of Example 114),
4-(2-aminoethoxy)-N-[3-(2-cyclohexylphenyl)phenyl]-3-methoxyphenylacetamide (the compound of Example 122),
4-(2-aminoethoxy)-N-[3-(2-fluorophenyl)phenyl]-3-methoxyphenylacetamide (the compound of Example 123),
4-(2-aminoethoxy)-N-[3-(4-fluorophenyl)phenyl]-3-methoxyphenylacetamide (the compound of Example 124),
4-(2-aminoethoxy)-N-[3-(2-chlorophenyl)phenyl]-3-methoxyphenylacetamide (the compound of Example 125),
4-(2-aminoethoxy)-N-[3-(3-chlorophenyl)phenyl]-3-methoxyphenylacetamide (the compound of Example 126),
4-(2-aminoethoxy)-N-[3-(3,5-difluorophenyl)phenyl]-3-methoxyphenylacetamide (the compound of Example 129),
4-(2-aminoethoxy)-3-methoxy-N-[3-(2-methylphenyl)phenyl]-phenylacetamide (the compound of Example 131),
4-(2-aminoethoxy)-3-methoxy-N-[3-(2,4,6-trimethylphenyl)-phenyl]phenylacetamide (the compound of Example 133),
4-(2-aminoethoxy)-N-[3-(3-isopropylphenyl)phenyl]-3-methoxyphenylacetamide (the compound of Example 136),
4-(2-aminoethoxy)-3-methoxy-N-[3-(4-trifluoromethylphenyl)-phenyl]phenylacetamide (the compound of Example 140),
4-(2-aminoethoxy)-3-methoxy-N-[3-(2-trifluoromethylphenyl)-phenyl]phenylacetamide (the compound of Example 142), 4-(2-aminoethoxy)-3-methoxy-N-[3-(2-phenylphenyl)phenyl]-phenylacetamide (the compound of Example 143),
4-(2-aminoethoxy)-3-methoxy-N-[3-(3-phenylphenyl)phenyl]-phenylacetamide (the compound of Example 145),
4-(2-aminoethoxy)-N-[3-(3-methoxycarbonylphenyl)phenyl]-3-methoxyphenylacetamide (the compound of Example 146),
4-(2-aminoethoxy)-3-methoxy-N-[3-(3-trifluoromethoxyphenyl)-phenyl]phenylacetamide (the compound of Example 150),
4-(2-aminoethoxy)-3-methoxy-N-[3-(2-methylthiophenyl)-phenyl]phenylacetamide (the compound of Example 158),
4-(2-aminoethoxy)-3-methoxy-N-[3-(thiophen-3-yl)phenyl]-phenylacetamide (the compound of Example 161),
4-(2-aminoethoxy)-3-methoxy-N-[3-(naphthalen-1-yl)phenyl]-phenylacetamide (the compound of Example 163),
4-(2-aminoethoxy)-N-[3-(2H-benzo[d]-1,3-dioxolan-5-yl)phenyl]-3-methoxyphenylacetamide (the compound of Example 164),
4-(2-aminoethoxy)-N-[3-(benzofuran-2-yl)phenyl]-3-methoxyphenylacetamide (the compound of Example 166),
4-(2-aminoethoxy)-N-[3-(3-tert-butylphenyl)phenyl]-3-methoxyphenylacetamide (the compound of Example 169),
4-(2-aminoethoxy)-N-[(2-fluoro-5-phenyl)phenyl]-3-methoxyphenylacetamide (the compound of Example 170),
4-(2-aminoethoxy)-N-[(2-methoxy-3-fluoro-5-phenyl)phenyl]-3-methoxyphenylacetamide (the compound of Example 171),
4-(2-aminoethoxy)-N-[(2-methyl-5-phenyl)phenyl]-3-methoxyphenylacetamide (the compound of Example 172),
4-(2-aminoethoxy)-3-methoxy-N-[(3-phenyl-4-methyl)phenyl]-phenylacetamide (the compound of Example 173),
4-(2-aminoethoxy)-3-methoxy-N-[(2-methoxy-5-phenyl)phenyl]-phenylacetamide (the compound of Example 177),
4-(2-aminoethoxy)-3-methoxy-N-[(3-trifluoromethyl-5-phenyl)-phenyl]phenylacetamide (the compound of Example 178),
4-(2-aminoethoxy)-3-methoxy-N-[(3-phenyl-4-trifluoromethoxy)-phenyl]phenylacetamide (the compound of Example 179),
4-(2-aminoethoxy)-3-methoxy-N-[(4-methyl-3,5-diphenyl)-phenyl]phenylacetamide (the compound of Example 181),
4-(2-aminoethoxy)-N-[3-(3-cyclohexylphenyl)phenyl]-3-methoxyphenylacetamide (the compound of Example 183),
4-(2-aminoethoxy)-N-[3-(2-tert-butylphenyl)phenyl]-3-methoxyphenylacetamide (the compound of Example 184),
4-(2-aminoethoxy)-3-methoxy-N-[3-(3-phenoxyphenyl)phenyl]-phenylacetamide (the compound of Example 186),
4-(2-aminoethoxy)-3-methoxy-N-[3-(2-phenylethyloxy)phenyl]-phenylacetamide (the compound of Example 187),
4-(2-aminoethoxy)-N-[3-[(cis)-4-tert-butylcyclohexan-1-yl]-phenyl]-3-methoxyphenylacetamide (the compound of Example 194),
4-(2-aminoethoxy)-N-[3-[(trans)-4-tert-butylcyclohexan-1-yl]-phenyl]-3-methoxyphenylacetamide (the compound of Example 195),
4-(2-aminoethoxy)-3-methoxy-N-[3-(piperidin-1-yl)phenyl]-phenylacetamide (the compound of Example 197),
4-(2-aminoethoxy)-N-[3-(3-cyclohexylpiperidin-1-yl)phenyl]-3-methoxyphenylacetamide (the compound of Example 199),
4-(2-aminoethoxy)-3-methoxy-N-[3-(3-phenylpiperidin-1-yl)-phenyl]phenylacetamide (the compound of Example 200),
4-(2-aminoethoxy)-3-methoxy-N-[3-(2-azaspiro[5, 5]undecan-2-yl)phenyl]phenylacetamide (the compound of Example 201),
4-(2-aminoethoxy)-3-methoxy-N-[3-[2-(3-methylphenyl)ethyl]-phenyl]phenylacetamide (the compound of Example 217),
4-(2-aminoethoxy)-3-methoxy-N-[3-[2-(2-fluorophenyl)ethyl]-phenyl]phenylacetamide (the compound of Example 219),
4-(2-aminoethoxy)-3-methoxy-N-[1-oxo-2-phenylmethyl-1,2,3,4-tetrahydronaphthalen-7-yl]phenylacetamide (the compound of Example 225),
4-(2-aminoethoxy)-3-methoxy-N-[1-benzylindol-6-yl]phenylacetamide (the compound of Example 238), and
4-hydroxy-3-methoxy-N-[1-oxo-2-phenylmethyl-1,2,3,4-tetrahydronaphthalen-7-yl]phenylacetamide (the compound of Example 249).

The compounds of the formula (I) include, for example, in addition to the compounds of Examples as described below, the compounds of Table 1, and a pharmaceutically acceptable salt thereof, or a hydrate or solvate thereof.

The following abbreviations may be used in the following Table 1, Reference Examples and Examples in order to simplify the description.

Me: methyl group, Et: ethyl group, i-Pr: isopropyl group, Bu: butyl group, t-Bu: tert-butyl group, Ph: phenyl group, Ms: methanesulfonyl group, Boc: tert-butoxycarbonyl group.

TABLE 1

| $R^1$ | $R^2$ | $R^3$ | $R^4$ | $R^5$ |
|---|---|---|---|---|
| MeO | $H_2NCH_2CH_2-$ | H | (methylspiro[5.4]decyl) | H |

TABLE 1-continued

Structure: R¹, R²O on one benzene ring (positions 2, 5, 6 labeled with R³), CH₂-C(=O)-NH linker to another benzene ring (positions 2, 5, 6 labeled, with R⁴ at 4 and R⁵).

| R¹ | R² | R³ | R⁴ | R⁵ |
|---|---|---|---|---|
| HO | H | 6-I | 4-(t-Bu)phenyl | 4-CF₃ |
| MsNH | H₂NCH₂CH₂— | H | cyclohexyl | H |
| MeO | H | 5-I | 3-fluorophenyl (with Me) | H |
| MeO | H₂NCH₂CH₂— | 2-I | —Ph | 4-F |
| Cl | H₂NCH₂CH₂— | H | —CH₂CH₂Ph | H |
| PhSO₂NH | H₂NCH₂CH₂— | H | —Ph | H |
| MeO | HOCH₂CH₂HNCH₂CH₂— | H | —Ph | 3-OCF₃ |
| MeO | (HOCH₂CH₂)₂NCH₂CH₂— | H | 4-chlorophenyl | H |
| MeO | H₂NCH₂CH₂HNCH₂CH₂— | 5-Br | cyclohexyl | H |
| MeO | HOOCCH₂CH₂— | 5-Cl | 2-methoxyphenyl | H |
| NO₂ | H₂NCH₂CH₂— | H | propyl-cycloheptyl | 2-Me |
| MeO | H₂NCH₂CH₂— | H | 2-methoxycyclohexyl | H |
| MeO | H₂NCH₂CH₂— | 5-Bu-t | 2-(CF₃)-phenyl with -CH₂CH₂CH₂-OMe | H |
| NH₂ | H | H | cyclohexyl-C(=O)- | H |
| MeO | H₂NCH₂CH₂— | 5-CHO | 3-(OCF₃)phenyl-C(=O)- | H |

TABLE 1-continued

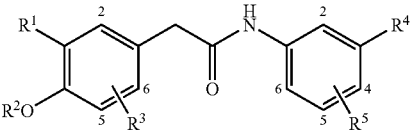

| R¹ | R² | R³ | R⁴ | R⁵ |
|---|---|---|---|---|
| Me₂N | H | H |  | H |
| MeO | PhCO— | H | 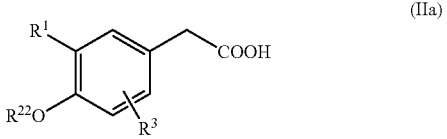 | H |
| MeO | H₂NCH₂CH₂— | H | 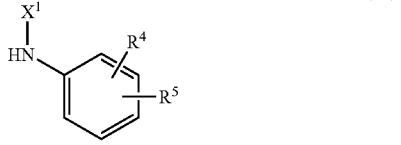 | 4-Cl |

The compounds of the formula (I) may be prepared, for example, by the following Processes.

Process A

The compound of the formula (I) wherein $R^2$ is a-hydrogen atom, a $C_{1-6}$ alkylcarbonyl group, an arylcarbonyl group or —$(CH_2)_m$—$N(R^6)(R^7)$ [m, $R^6$ and $R^7$ are as defined above, except that —$N(R^6)(R^7)$ is a primary or secondary amino group] may be prepared by reacting a compound of the formula (IIa):

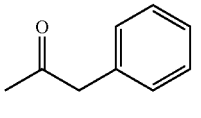

(IIa)

wherein $R^{22}$ is a hydrogen atom, a $C_{1-6}$ alkylcarbonyl group, an arylcarbonyl group or —$(CH_2)_m$—$N(R^6)(R^7)$ [m, $R^6$ and $R^7$ are as defined above, excluding the compound wherein —$N(R^6)(R^7)$ is a primary or secondary amino group], $R^1$ and $R^3$ are as defined above, with a compound of the formula (III):

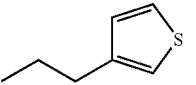

(III)

wherein $R^4$, $R^5$ and $X^1$ are as defined above.

The reaction of the compound of the formula (IIa) and the compound of the formula (III) is carried out under conventional reaction conditions for amide bond forming reaction. The compound of the formula (IIa) may be reacted with the compound of the formula (III) after it is converted into a reactive derivative at the carboxyl group thereof.

The reactive derivative of a carboxyl group of the compound of the formula (IIa) is, for example, a lower alkyl ester (especially, methyl ester), an active ester, an acid anhydride, an acid halide (especially an acid chloride). The active ester is, for example, p-nitrophenyl ester, N-hydroxysuccinimide ester, pentafluorophenyl ester. The acid anhydride is, for example, a symmetric acid anhydride or a mixed acid anhydride with ethyl chlorocarbonate, isobutyl chlorocarbonate, isovaleric acid, pivalic acid, etc.

When the compound of the formula (IIa) per se is used, the present reaction is usually carried out in the presence of a condensing agent. The condensing agent is, for example, N,N'-dicyclohexylcarbodiimide, 1-ethyl-3-(3-dimethylaminopropyl)carbodiimide hydrochloride, N,N'-carbonyldiimidazole, benzotriazol-1-yloxy-tris(pyrrolidino)phosphonium hexafluorophosphate, etc. These condensing agents are used alone, or in a combination of these condensing agents and a peptide synthesis reagent such as N-hydroxysuccinimide, N-hydroxybenzotriazole, etc.

The reaction of the compound of the formula (IIa) or a reactive derivative thereof with the compound of the formula (III) is carried out in a solvent or without a solvent. The solvent used should be selected according to the kinds of the starting compound, etc., and includes, for example, toluene, tetrahydrofuran, dioxane, ethylene glycol dimethyl ether, methylene chloride, chloroform, ethyl acetate, acetone, acetonitrile, dimethylformamide, etc. These solvents may be used alone or in the form of a mixture of two or more solvents. The compound of the formula (III) may be used in the form of an acid addition salt such as hydrochloride, etc., to produce a free basic compound in the reaction system.

This reaction is usually carried out in the presence of a base. The base includes, for example, an inorganic base such as potassium carbonate, sodium hydrogen carbonate, or an organic base such as triethylamine, ethyldiisopropylamine, N-methylmorpholine, pyridine, 4-dimethylaminopyridine, etc. The reaction temperature may vary according to the kinds of the starting compounds used, and it is usually in the range of about –30° C. to about 150° C., preferably in the range of about –10° C. to about 70° C. When the compound (IIa) or the compound (III) has a functional group participating in the reaction within the structure thereof, it is preferable to protect such functional groups by a conventional method, and to remove the protecting groups after the reaction is complete.

The starting compound (IIa) of this reaction may be commercially available ones or may be prepared by a conventional method, such as methods disclosed in Korean J. Med. Chem., 1, 36 (1991); J. Med. Chem., 39, 4942 (1996); J. Chem. Soc. Perkin Trans. 1, 833 (1984); J. Am. Chem. Soc., 72, 5163 (1950); J. Org. Chem., 24, 4658 (1983) and Synthesis, 126 (1981), or a modified method of these methods.

On the other hand, the compound of the formula (III) may be commercially available ones or may be prepared by the following Process.

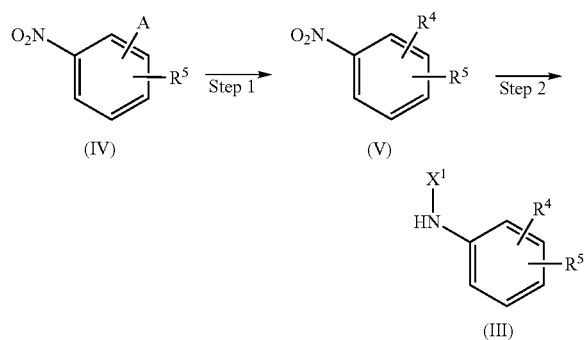

wherein A is a leaving atom or a leaving group, and $R^4$, $R^5$ and $X^1$ are as defined above.

The leaving atom or leaving group for A in the formula (IV) is, for example, a halogen atom, a trifluoromethanesulfonyloxy group, a hydroxy group, and a boronic acid group.

(Step 1)

When $R^4$ of the compound of the formula (V) is a $C_{6-10}$ alkyl group, or a group of the above formula (A) [in which Y is a single bond, a $C_{1-3}$ alkylene group, a $C_{2-3}$ alkenylene group, a $C_{2-3}$ alkynylene group or a $C_{2-3}$ alkenylenecarbonyl group, and $R^8$ is as defined above], for example, when A of the compound of the formula (IV) is a halogen atom or a trifluoromethanesulfonyloxy group, Step 1 is carried out using an organo zinc derivative, an organo tin derivative, an arylboronic acid derivative, an alkyne derivative, an alkene derivative, etc., and when the compound of the formula (IV) is an organo zinc derivative, an organo tin derivative, an arylboronic acid derivative, an alkyne derivative or an alkene derivative, then Step 1 is carried out using a halogen derivative, a trifluoromethanesulfonyloxy derivative, etc., by the method disclosed in J. Org. Chem., 56, 1445 (1991); Angew. Chem. Int. Ed. Engl., 25, 508 (1986); Synth. Commun., 11, 513 (1981); Synthesis, 627 (1980); Org. React., 27, 345 (1982) or Synthesis, 993 (1991), or by a modified method thereof.

The compound of the formula (V) wherein $R^4$ is a group of the above formula (A) (in which Y is —CO(CH$_2$)$_p$— or —CONH(CH$_2$)$_p$— and $R^8$ is as defined above) may be commercially available ones or prepared by a conventional method or a modified method thereof.

In the case of the compound of the formula (V) wherein $R^4$ is a group of the formula (A) (in which Y is —O—, —O—(CH$_2$)$_2$— or —O—(CH$_2$)$_3$— and $R^8$ is as defined above), for example, when the starting compound of the formula (IV) wherein A is a halogen atom, and a phenol derivative are used, the reaction is carried out by the method disclosed in Chem. Ber., 38, 2212 (1905) or J. Org. Chem., 50, 3717 (1985), or when the staring compound of the formula (IV) wherein A is a hydroxy group and a halogen derivative or an alcohol compound are used, the reaction is carried out by the method disclosed in J. Med. Chem., 25, 57 (1982); J. Pharm. Sci., 56, 871 (1967) or Org. React., 42, 335 (1992), or a modified method thereof.

In the case of the compound of the formula (V) wherein $R^4$ is a group of the above formula (C), for example, when the starting compound of the formula (IV) wherein A is a trifluoromethanesulfonyloxy group or a halogen atom, and an amine derivative are used, Step 1 is carried out, for example, by the method disclosed in Tetrahedron Lett., 39, 7979 (1998) or Tetrahedron, 55, 13285 (1999), or a modified method thereof.

(Step 2)

This Step is carried out by treating the compound of the formula (V) in a suitable solvent with a reducing agent suitable for reduction of a nitro group into an amino group, or by catalytic reduction. The reducing agent is, for example, a combination of a metal (e.g., iron, zinc, tin, etc.) or a metal salt (e.g., stannic chloride, etc.) and an acid or a salt thereof (e.g., hydrochloric acid, acetic acid, ammonium acetate, etc.). Stannic chloride may be used alone. The catalytic reduction is carried out in the presence of a catalyst (e.g., palladium on carbon, platinum, etc.) under atmospheric pressure or under pressure. The solvent used should be selected according to the kinds of the reducing agent or catalyst, etc., and includes, for example, ethanol, ethyl acetate, acetone, dimethylformamide, water, acetic acid, hydrochloric acid, etc., and these solvents may be used alone, or in the form of a mixture of two or more of these solvents. The reaction temperature may vary according to the kinds of the reducing agents or catalysts to be used, etc. and it is usually in the range of 20° C. to 150° C.

The compound of the formula (III) wherein $R^4$ and $R^5$ combine together with the benzene ring to which they bond, and form a tetralone ring or an indole ring may be prepared by aldole reaction or alkylation reaction in the presence of a base of a commercially available tetralone or indole derivative, followed by treating in a similar manner to the above (Step 2). Examples of this reaction are shown in Reference Example 8 and Reference Example 9.

Process B

The compound of the formula (I) wherein $R^2$ is —(CH$_2$)$_m$OH or —(CH$_2$)$_q$COOH may be prepared by hydrolysis, acid decomposition or catalytic hydrogenation of a compound of the formula (Id):

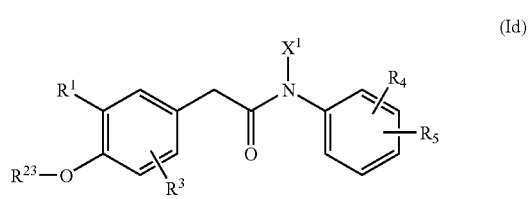

wherein $R^{23}$ is —(CH$_2$)$_m$OW$^1$ or —(CH$_2$)$_q$COOW$^1$, W$^1$ is a $C_{1-6}$ alkyl group which may optionally be substituted by a methoxy group or an ethoxy group, a benzyl group which may optionally be substituted by 1 or 2 methoxy groups, and $R^1$, $R^3$, $R^4$, $R^5$, $X^1$, m and q are as defined above.

Examples of $W^1$ of the above formula (Id) is a methyl group, an ethyl group, a tert-butyl group, a methoxymethyl group, a 2-ethoxyethyl group, a benzyl group, a 4-methoxybenzyl group, a 2,4-dimethoxybenzyl group. The hydrolysis is carried out by a conventional method, for example, by reacting with an alkali hydroxide such as sodium hydroxide, potassium hydroxide in a suitable solvent. The solvent used is, for example, methanol, ethanol, tetrahydrofuran, water, and these solvents may be used alone, or in the form of a mixture of two or more solvents.

The acid decomposition is carried out, for example, by treating with a Lewis acid (e.g., trimethylsilyl trifluoromethanesulfonic acid ester, boron trifluoride diethyl ether complex), an organic acid (e.g., trifluoroacetic acid, trifluoromethanesulfonic acid, etc.), an inorganic acid (e.g., hydrochloric acid, etc.). The solvent used is, for example, diethyl ether, methylene chloride, ethyl acetate, methanol, ethanol, tetrahydrofuran, water, and these solvents may be used alone, or in the form of a mixture of two or more solvents.

The catalytic hydrogenation is carried out in a conventional manner, for example, using palladium on carbon, palladium hydroxide, platinum as a catalyst. The solvent used is, for example, ethyl acetate, methanol, ethanol, tetrahydrofuran, water, and these solvents may be used alone, or in the form of a mixture of two or more solvents.

In addition, said reaction may be carried out by a novel method, and said method should not be defined or limited.

The compound of the above formula (Id) may be prepared by reacting a compound of the formula (IIb):

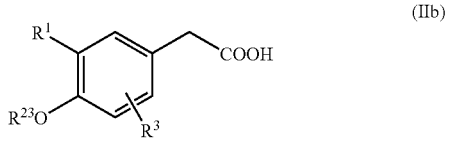

(IIb)

wherein $R^1$, $R^{23}$ and $R^3$ are as defined above, with the compound of the above formula (III) by a similar method disclosed in the above Process A.

The starting compound (IIb) may be commercially available ones or may be prepared by a conventional method, for example, it can be prepared by a similar method to the method for preparing the starting compound (IIa) in the above Process A or by a modified method thereof.

Process C

The compound of the formula (I) wherein $R^2$ is $-(CH_2)_m-NH(R^6)$ may be prepared by the hydrolysis, acid decomposition or catalytic hydrogenation as disclosed in Process B, or by reduction, catalytic hydrogenation or hydrolysis as mentioned below of a compound of the formula (Ie):

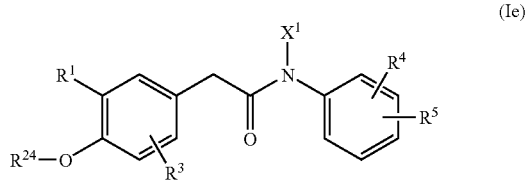

(Ie)

wherein $R^{24}$ is $-(CH_2)_m-N(R^6)(W^2)$, $-(CH_2)_m-N_3$ or $-(CH_2)_mW^3$, $W^2$ is a $C_{1-6}$ alkyloxycarbonyl group, an aryloxycarbonyl group, an aryl-$C_{1-3}$ alkyloxycarbonyl group, a $C_{1-6}$ alkylcarbonyl group or an arylcarbonyl group, $W^3$ is a cyclic imide group binding onto the nitrogen atom, and $R^1$, $R^3$, $R^4$, $R^5$, $R^6$, $X^1$ and m are as defined above. Examples of $W^2$ of the above formula (Ie) are tert-butyloxycarbonyl group, 9-fluorenyloxy-carbonyl group, benzyloxycarbonyl group. Example of $W^3$ is phthalimid-1-yl group.

The compound of the formula (Ie) wherein $R^{24}$ is $-(CH_2)_m-N_3$ may be converted into the compound of the formula (I) by treating with a reducing agent suitable for reduction of an azide group into an amino group such as triphenylphosphine, or by catalytic hydrogenation. The catalytic hydrogenation is carried out in a conventional manner, for example, using palladium on carbon, palladium hydroxide, platinum, as a catalyst. The solvent used is, for example, ethyl acetate, methanol, ethanol, tetrahydrofuran, water, and these solvents may be used alone, or in the form of a mixture of two or more solvents.

The compound of the formula (Ie) wherein $R^{24}$ is $-(CH_2)_mW^3$ may be converted into the compound of the formula (I) by a method suitable for conversion of a cyclic imide group into an amino group, for example, by treating with hydrazine, an acid or a base. The acid used is, for example, hydrochloric acid, sulfuric acid, etc., and the base used is, for example, sodium hydroxide, potassium hydroxide, etc. The solvent used is, for example, ethyl acetate, methanol, ethanol, tetrahydrofuran, water, and these solvents may be used alone, or in the form of a mixture of two or more solvents.

The compound of the above formula (Ie) may be prepared by reacting a compound of the formula (IIc):

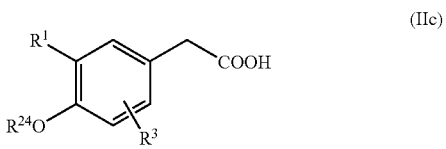

(IIc)

wherein $R^1$, $R^{24}$ and $R^3$ are as defined above, with the compound of the formula (III) in a similar manner to the above Process A.

The starting compound (IIc) may be commercially available ones, or may be prepared by a conventional method, for example, by the method disclosed in J. Med. Chem., 39, 2939 (1996), or the method for preparing the starting compound (IIa) in the above Process A, or a modified method thereof.

Process D

The compound of the formula (I) may be prepared by the reaction disclosed in Step 1 of the above Process A using as a starting compound a compound of the formula (If):

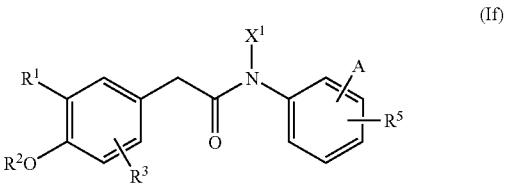

(If)

wherein $R^1$, $R^2$, $R^3$, $R^5$, $X^1$ and A are as defined above.

The starting compound (If) of this reaction may be prepared in a similar manner to the method disclosed in the above Process A, Process B and Process C.

Process E

The compound of the formula (I) may be prepared by a conventional method, for example, by the methods disclosed in WO 00/50387 and JP-A-63-295537, or a modified method thereof, using as a starting compound a compound of the formula (Ig):

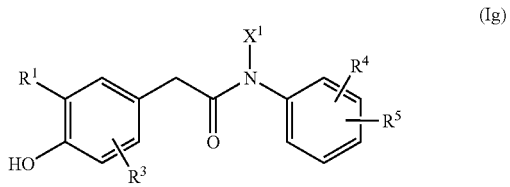

wherein $R^1$, $R^3$, $R^4$, $X^1$ and $R^5$ are as defined above.

Examples of this Process are shown in Examples 33, 69, 70, 71, 72, 73, 74, 119 and 206.

The compounds of the formula (I) obtained by the above Processes can be isolated and purified by a conventional method such as chromatography, recrystallization, re-precipitation, etc. The compound of the formula (I) can be obtained either in the form of a free base or an acid addition salt thereof, according to the kinds of functional groups within the structure, the selection of the starting compounds, and reaction conditions, and these salts can be converted into the compound of the formula (I) by a conventional method. On the other hand, the compound of the formula (I) having a group being capable of forming an acid addition salt within the structure thereof may be converted into an acid addition salt thereof by treating with various acids in a conventional manner.

The pharmacological activities of the present compounds are explained by the following pharmacological experiments on the representative compounds of the present invention, but the present invention should not be construed to be limited to these pharmacological experiments.

Experiment 1: Phenyl-1,4-benzoquinone-induced Writhing Test

Referring to the method disclosed in Proc. Soc. exp. Biol. Med., 95, 729 (1957), the effect of the test compounds on the writhing test induced by phenyl-1,4-benzoquinone (Wako Pure Chemical Industries, Ltd., Japan) (hereinafter, referred to as PBQ) was examined using male Std:ddY mice fasted overnight (five mice per group, body weight: 15 to 20 g). For subcutaneous administration, a test compound was dissolved in a physiological saline solution containing 10% Tween 80 (Sigma, USA) and 10% ethanol to give a suitable concentration. For oral administration, a test compound was suspended in 0.5% tragacanth solution. A test compound was administered 60 minutes before the intraperitoneal injection of PBQ solution (0.02% in physiological saline solution containing 5% ethanol), and the number of writhing movements for each mouse was counted for 10 minutes from 5 minutes after the injection of PBQ. In the control group, a physiological saline solution containing 10% Tween 80 and 10% ethanol was administered in the case of subcutaneous administration, or a 0.5% tragacanth solution was administered in the case of oral administration. The number of writhing movements in the test compound-treated group was compared with that in the control group, and the writhing inhibitory percentage was calculated therefrom and considered as an analgesic effect.

Writhing inhibitory percentage (%)=$[(A-B)/A] \times 100$

In the above equation, A means the number of writhing movements in the control group, and B means the number of writhing movements in the test compound-treated group. From the writhing inhibitory percentage of the test compound, $ED_{50}$ (mg/kg) was calculated by logit analysis. The test results are shown in Table 2, Table 3, Table 4 and Table 5.

TABLE 2

| Test Comp. | Inhibitory percentage (%)* |
|---|---|
| Ex. 1 | 100 |
| Ex. 3 | 91.3 |
| Ex. 4 | 79.6 |
| Ex. 5 | 83.5 |
| Ex. 6 | 68.9 |
| Ex. 9 | 93.2 |
| Ex. 11 | 88.4 |
| Ex. 12 | 78.7 |
| Ex. 13 | 100 |
| Ex. 15 | 72.8 |
| Ex. 16 | 64.1 |
| Ex. 17 | 68.3 |
| Ex. 20 | 96.1 |
| Ex. 21 | 45.2 |
| Ex. 24 | 47.1 |
| Ex. 34 | 41.5 |
| Ex. 35 | 89.4 |
| Ex. 36 | 92.3 |
| Ex. 37 | 59.6 |
| Ex. 45 | 58.3 |
| Ex. 48 | 48.6 |
| Ex. 51 | 57.7 |
| Ex. 52 | 47.6 |
| Ex. 54 | 90.4 |
| Ex. 56 | 82.7 |
| Ex. 58 | 54.4 |
| Ex. 59 | 61.0 |
| Ex. 60 | 50.5 |
| Ex. 61 | 72.8 |
| Ex. 62 | 100 |
| Ex. 63 | 100 |
| Ex. 64 | 56.1 |
| Ex. 69 | 99.0 |
| Ex. 70 | 93.2 |
| Ex. 71 | 94.2 |
| Ex. 77 | 100 |
| Ex. 78 | 94.5 |
| Ex. 80 | 100 |
| Ex. 81 | 100 |
| Ex. 82 | 66.7 |
| Ex. 83 | 83.0 |
| Ex. 84 | 67.7 |
| Ex. 85 | 76.9 |
| Ex. 86 | 78.8 |
| Ex. 87 | 95.8 |
| Ex. 88 | 76.6 |
| Ex. 93 | 65.3 |
| Ex. 95 | 62.2 |
| Ex. 96 | 47.0 |
| Ex. 97 | 54.9 |
| Ex. 100 | 100 |
| Ex. 101 | 100 |
| Ex. 102 | 58.1 |
| Ex. 114 | 98.0 |
| Ex. 160 | 47.4 |
| Ex. 167 | 55.2 |
| Ex. 189 | 65.9 |
| Ex. 210 | 40.5 |
| Ex. 233 | 67.0 |
| Ex. 238 | 70.2 |
| Ex. 243 | 62.2 |
| Ex. 245 | 55.4 |
| Ex. 247 | 59.2 |
| Ex. 249 | 89.4 |
| Ex. 250 | 55.0 |
| Ex. 251 | 42.7 |

TABLE 2-continued

| Test Comp. | Inhibitory percentage (%)* |
|---|---|
| Ex. 253 | 48.3 |
| Ex. 254 | 42.5 |
| Ex. 255 | 64.9 |
| Capsaicin | 46.6 |

*Inhibitory percentage (%) when a test compound was subcutaneously administered at a dose of 1 mg/kg.

TABLE 3

| Test Comp. | $ED_{50}$ (mg/kg sc) |
|---|---|
| Ex. 1 | 0.014 |
| Ex. 3 | 0.46 |
| Ex. 5 | 0.57 |
| Ex. 9 | 0.23 |
| Ex. 11 | 0.19 |
| Ex. 12 | 0.32 |
| Ex. 13 | 0.097 |
| Ex. 17 | 0.62 |
| Ex. 20 | 0.056 |
| Ex. 34 | 0.48 |
| Ex. 35 | 0.23 |
| Ex. 36 | 0.046 |
| Ex. 37 | 0.46 |
| Ex. 45 | 0.55 |
| Ex. 51 | 0.74 |
| Ex. 54 | 0.081 |
| Ex. 56 | 0.11 |
| Ex. 59 | 0.53 |
| Ex. 60 | 0.83 |
| Ex. 61 | 0.13 |
| Ex. 62 | 0.23 |
| Ex. 63 | 0.016 |
| Ex. 69 | 0.088 |
| Ex. 70 | 0.16 |
| Ex. 71 | 0.16 |
| Ex. 77 | 0.25 |
| Ex. 78 | 0.13 |
| Ex. 80 | 0.37 |
| Ex. 83 | 0.10 |
| Ex. 84 | 0.45 |
| Ex. 85 | 0.31 |
| Ex. 86 | 0.33 |
| Ex. 87 | 0.40 |
| Ex. 101 | 0.23 |
| Ex. 233 | 0.55 |
| Ex. 238 | 0.37 |
| Ex. 249 | 0.043 |
| Capsaicin | 1.15 |

TABLE 4

| Test Comp. | Inhibitory percentage (%)* |
|---|---|
| Ex. 20 | 97.1 |
| Ex. 59 | 75.5 |
| Ex. 61 | 89.0 |
| Ex. 62 | 96.1 |
| Ex. 63 | 100 |
| Ex. 66 | 100 |
| Ex. 67 | 90.2 |
| Ex. 69 | 73.5 |
| Ex. 70 | 68.6 |
| Ex. 122 | 99.0 |
| Ex. 123 | 100 |
| Ex. 124 | 100 |
| Ex. 125 | 93.0 |

TABLE 4-continued

| Test Comp. | Inhibitory percentage (%)* |
|---|---|
| Ex. 126 | 89.9 |
| Ex. 129 | 76.9 |
| Ex. 131 | 100 |
| Ex. 133 | 94.0 |
| Ex. 136 | 99.0 |
| Ex. 140 | 91.0 |
| Ex. 142 | 98.9 |
| Ex. 143 | 73.2 |
| Ex. 145 | 85.9 |
| Ex. 146 | 76.9 |
| Ex. 150 | 100 |
| Ex. 158 | 95.1 |
| Ex. 161 | 79.4 |
| Ex. 163 | 87.9 |
| Ex. 164 | 99.0 |
| Ex. 166 | 96.0 |
| Ex. 169 | 100 |
| Ex. 170 | 87.9 |
| Ex. 171 | 94.0 |
| Ex. 172 | 75.9 |
| Ex. 173 | 100 |
| Ex. 177 | 78.9 |
| Ex. 178 | 100 |
| Ex. 179 | 100 |
| Ex. 181 | 80.9 |
| Ex. 183 | 83.5 |
| Ex. 184 | 100 |
| Ex. 186 | 84.3 |
| Ex. 194 | 96.2 |
| Ex. 195 | 77.7 |
| Ex. 197 | 89.1 |
| Ex. 199 | 71.6 |
| Ex. 200 | 84.2 |
| Ex. 201 | 100 |
| Ex. 209 | 73.0 |
| Ex. 217 | 96.3 |
| Ex. 218 | 74.0 |
| Ex. 219 | 94.0 |
| Ex. 225 | 73.5 |
| Capsaicin | 20.6** |

*Inhibitory percentage (%) when a test compound was orally administered at a dose of 10 mg/kg.
**Inhibitory percentage (%) when Capsaicin was orally administered at a dose of 30 mg/kg.

TABLE 5

| Test Comp. | $ED_{50}$ (mg/kg po) |
|---|---|
| Ex. 20 | 1.28 |
| Ex. 59 | 0.93 |
| Ex. 60 | 0.68 |
| Ex. 61 | 3.00 |
| Ex. 62 | 0.43 |
| Ex. 63 | 0.021 |
| Ex. 69 | 2.81 |
| Ex. 70 | 9.70 |
| Ex. 122 | 0.58 |
| Ex. 123 | 0.76 |
| Ex. 124 | 0.71 |
| Ex. 125 | 0.71 |
| Ex. 126 | 2.19 |
| Ex. 129 | 1.89 |
| Ex. 131 | 1.10 |
| Ex. 133 | 1.28 |
| Ex. 136 | 3.11 |
| Ex. 140 | 2.18 |
| Ex. 142 | 1.19 |
| Ex. 143 | 3.72 |
| Ex. 146 | 2.68 |
| Ex. 150 | 1.32 |
| Ex. 158 | 2.12 |

TABLE 5-continued

| Test Comp. | ED$_{50}$ (mg/kg po) |
|---|---|
| Ex. 161 | 2.79 |
| Ex. 163 | 1.61 |
| Ex. 164 | 1.56 |
| Ex. 166 | 2.40 |
| Ex. 169 | 1.29 |
| Ex. 170 | 1.06 |
| Ex. 171 | 0.96 |
| Ex. 172 | 4.42 |
| Ex. 173 | 0.87 |
| Ex. 177 | 3.41 |
| Ex. 178 | 1.65 |
| Ex. 179 | 0.95 |
| Ex. 181 | 1.11 |
| Ex. 183 | 3.09 |
| Ex. 184 | 0.60 |
| Ex. 186 | 1.83 |
| Ex. 194 | 1.05 |
| Ex. 197 | 5.26 |
| Ex. 201 | 2.04 |
| Ex. 209 | 6.79 |
| Ex. 217 | 1.13 |
| Ex. 218 | 1.82 |
| Ex. 219 | 1.46 |
| Ex. 225 | 4.79 |
| Capsaicin | >30 |

As shown in Table 2, the compounds of the present invention exhibited a potent analgesic activity by subcutaneous administration. The compounds of Examples as shown in Table 3 showed a potent analgesic activity with an ED$_{50}$ of not more than 1 mg/kg (subcutaneous administration), and among them, the compounds of Examples 1, 13, 20, 36, 54, 63, 69, 83 and 249 especially showed an extremely potent analgesic activity with an ED$_{50}$ of not more than 0.1 mg/kg (subcutaneous administration).

The compounds of the present invention as shown in Table 4 showed a comparatively potent analgesic activity by oral administration. Especially, the compounds of Examples 59, 60, 62, 63, 122, 123, 124, 125, 171, 173, 179 and 184 showed a potent analgesic activity with an ED$_{50}$ of not more than 1 mg/kg (oral administration).

Experiment 2: Study of Pungency (Eye Wiping Test)

The pungency of the test compounds were studied referring to the method of Jancso et al. [Acta Physiol. Acad. Sci. Hung., 19, 113–131 (1961)] and the method of Szallasi et al. [Brit. J. Pharmacol., 119, 283–290 (1996)]. A test compound was dissolved in a physiological saline solution containing 10% ethanol and 10% Tween 80 into various concentrations (μg/ml), and a drop of the solution thereof was added dropwise into the eye of Jcl:SD strain male rats (5 to 25 mice per group, body weight; 220 to 280 g). Then, the number of the protective wiping movements with forefoot was counted for 3 minutes, and was considered as an index for pungency. The test results are expressed as average value±S.E.M., and the statistical significant differences between each test compound-treated group and the control group were analyzed using non-parametric Dunnett's multiple range test, and $p<0.05$ was considered as significant difference. The results are shown in Table 6.

TABLE 6

| Test Comp. | Concentration (μg/ml) | Number of wiping movements |
|---|---|---|
| Vehicle-Control group | — | 2.0 ± 0.4 |
| Capsaicin | 1 | 6.0 ± 0.8 |
| | 2 | 7.8 ± 1.4 |
| | 5 | 11.2 ± 3.0* |
| | 10 | 26.4 ± 6.0*** |
| | 20 | 38.0 ± 4.8*** |
| Vehicle-Control group | — | 3.2 ± 1.2 |
| Ex. 61 | 20 | 2.0 ± 0.8 |
| | 100 | 7.4 ± 2.1 |
| | 500 | 15.6 ± 4.5* |
| Vehicle-Control group | — | 3.2 ± 1.1 |
| Ex. 60 | 500 | 4.2 ± 1.2 |
| | 1000 | 8.4 ± 2.1 |
| Ex. 62 | 500 | 4.6 ± 1.2 |
| | 1000 | 7.6 ± 1.4 |
| Vehicle-Control group | — | 1.2 ± 0.4 |
| Ex. 63 | 50 | 7.2 ± 1.2 |
| | 200 | 12.8 ± 1.7** |
| Vehicle-Control group | — | 2.0 ± 1.1 |
| Ex. 20 | 100 | 5.0 ± 1.3 |
| | 500 | 10.6 ± 0.7** |
| Ex. 66 | 100 | 5.6 ± 2.4 |
| | 500 | 3.6 ± 1.6 |
| Ex. 67 | 100 | 3.8 ± 1.3 |
| | 500 | 13.4 ± 2.8** |
| Ex. 164 | 100 | 5.4 ± 2.8 |
| | 500 | 2.8 ± 1.7 |
| Ex. 186 | 100 | 4.0 ± 1.1 |
| | 500 | 12.2 ± 2.0** |
| Vehicle-Control group | — | 2.2 ± 1.1 |
| Ex. 225 | 500 | 4.4 ± 2.1 |
| | 1000 | 1.6 ± 1.2 |

*$p < 0.05$, $p < 0.01$, *$p < 0.001$ (in comparison with the corresponding vehicle control group)

As is shown in Table 6, capsaicin significantly increased the number of wiping movements at a dose of 5 μg/ml. On the other hand, the pungency of each compound of Examples as listed in Table 6 was one-tenth or less weaker than that of capsaicin. Among them, the compounds of Examples 60, 62, 66, 164 and 225 showed no significant increase in the number of wiping movements even at a high dose of 500 μg/ml, and their pungency is quiet weak.

As is apparent from the above test results, the compounds of the present invention, a pharmaceutically acceptable salt thereof, and a hydrate or solvate thereof exhibit a potent analgesic effect with a weak pungency, and they are efficacious even in oral administration. Therefore, the compounds of the present invention are useful as analgesic agents and antiinflammatory agents, and as an agent for treatment of neuropathic pain to which conventional analgesic agents are ineffective, or pain caused by rheumatic arthritis. In addition, the compounds of the present invention are also useful as a preventive and/or an agent for treatment of essential pruritus, allergy or nonallergic rhinitis, frequent urination and urinary incontinence with overactive bladder, stroke, irritable bowel syndrome, respiratory disorders such as asthma and chronic obstructive pulmonary disease, dermatitis, mucositis, gastric and duodenal ulcer, inflammatory bowel diseases and obesity.

The compounds of the present invention can be administered either orally, parenterally, percutaneouslly, rectally or intravaginally, but oral administration, injection and percutaneous administration are more preferable. The dose of the compounds of the present invention may vary according to the kinds of the compound, the administration routes, the conditions, ages of the patients, etc., but it is usually in the range of 0.01–150 mg/kg/day, preferably in the range of 0.1–20 mg/kg/day, which can be administered once a day or divided into several dosage forms.

The compounds of the present invention are usually administered in the form of a pharmaceutical preparation, which is prepared by mixing thereof with a pharmaceutically acceptable carrier or diluent. The pharmaceutical preparation is, for example, oral preparations such as tablets, capsules, granules, powders, syrups, etc., external preparations such as inhalants, nasal drops, ointments, patches, powders, etc., injection preparations such as intravenous injections, intramuscular injections, etc., drip infusions, eyedrops, suppositories, etc. These pharmaceutical formulations may be prepared by a conventional method.

The pharmaceutically acceptable carrier or diluent may be any conventional ones usually used in the pharmaceutical field, and does not react with the compounds of the present invention. Suitable examples of the pharmaceutically acceptable carrier or diluent for preparing tablets, capsules, granules and powders are, for example, excipients such as lactose, corn starch, white sugar, mannitol, calcium sulfate, crystalline cellulose, etc., disintegrants such as carmellose sodium, pregelatinized starch, carmellose calcium, etc., binders such as methylcellulose, gelatin, gum arabic, ethylcellulose, hydroxypropyl cellulose, polyvinylpyrrolidone, etc., lubricants such as light anhydrous silicic acid, magnesium stearate, talc, hydrogenated oil, etc. Tablets may be coated in a conventional manner with a coating agent such as carnauba wax, hydroxypropylmethylcellulose, macrogol, hydroxypropylmethyl phthalate, cellulose acetate phthalate, white sugar, titanium oxide, sorbitan fatty acid esters, calcium phosphate, etc.

Suitable examples of the pharmaceutically acceptable carrier or diluent for preparing syrups are sweetening agents such as white sugar, glucose, fructose, etc., suspending agents such as gum arabic, tragacanth, carmellose sodium, methylcellulose, sodium alginate, crystalline cellulose, bee gum, etc., dispersing agents such as sorbitan fatty acid ester, sodium lauryl sulfate, polysorbate 80, etc. If necessary, corrigents, flavors, preservatives may be added to syrups. Syrups may be in the form of a dry syrup, which is dissolved or suspended when used.

Suitable examples of the base for ointments are white petrolatum, plastivase, bleached beeswax, purified lanolin, hydrogenated caster oil, macrogol. When preparing ointments, if necessary, vegetable oils, liquid paraffin, etc. may be added thereto.

Suitable examples of the adhesive base for patches are polymer bases such as polyvinylpyrrolidone, polyisobutylene, vinyl acetate copolymer, acrylic copolymer, etc., plasticizers such as glycerin, propylene glycol, polyethylene glycol, triethyl citrate, acetyl triethyl citrate, diethyl phthalate, diethyl sebacate, dibutyl sebacate, acetylated monoglyceride, etc.

Suitable examples of the base for suppositories are cacao butter, saturated fatty acid glycerin ester, glycerogelatin, macrogol. when preparing suppositories, if necessary, surfactants, preservatives may be added to suppositories.

Injection preparations may be prepared by dissolving an acid addition salt of the compound (I) in a distilled water for injection, but if necessary, there may be added solubilizing agents, buffering agents, pH adjusters, isotonic agents, soothing agents, preservatives. Moreover, injection preparations may be in the form of a suspension, which is prepared by suspending the compound of the present invention per se in distilled water for injection or a vegetable oil. In these cases, if necessary, bases, suspending agents, thickening agents may be added thereto. Further, injection preparations may be in the form of powder or may be lyophilized, and it is dissolved when used, and in these cases, if necessary, excipients, etc. may be added thereto.

The content of the compound of the present invention in pharmaceutical compositions may vary based on the dosage forms, and it is usually in the range of 0.01 to 70% by weight to the total weight of the pharmaceutical composition. These pharmaceutical compositions may also contain other therapeutically effective compounds as well.

BEST MODE FOR CARRYING OUT THE INVENTION

The present invention will be illustrated in more detail by Reference Examples and Examples, but it should not be construed to be limited thereto. The compounds were identified by Elementary Analysis, Mass spectrum, IR spectrum, NMR spectrum, HPLC, etc.

The conditions for HPLC are as follows:

Column: CAPCELL PAK C18 SG 120 (manufactured by Shiseido Co., Ltd.), φ 4.6×150 mm, Temperature: 25° C., Flow: 1 ml/min., Solvent for elution: 10%, 20%, 25%, 30%, 40%, 45%, 50%, 65% or 75% acetonitrile/0.05% aqueous trifluoroacetic acid solution (concentration for each Example is shown in Table 36), UV (254 nm).

REFERENCE EXAMPLE 1

Preparation of 4-hydroxy-N-(3-iodophenyl)-3-methoxyphenylacetamide (Intermediate 1)

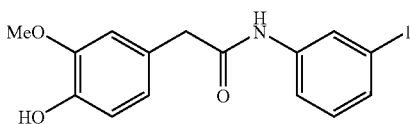

A mixture of 4-hydroxy-3-methoxyphenylacetic acid (4.65 g), pentafluorophenol (4.2 g), 1-ethyl-3-(3-dimethylaminopropyl)-carbodiimide hydrochloride (4.9 g) and methylene chloride (50 ml) was stirred at room temperature for 18 hours. The reaction solution was washed with water, and the organic layer was dried over sodium sulfate, and the solvent was evaporated under reduced pressure. The residue was purified by silica gel column chromatography (eluent: gradient from 0% to 100% hexane/ethyl acetate) to give 4-hydroxy-3-methoxyphenylacetic acid pentafluorophenyl ester (7.8 g). This product is dissolved in ethyl acetate (80 ml), and thereto is added 3-iodeaniline (7.4 g). The mixture is heated at 60° C. under stirring for 18 hours. The solvent is evaporated under reduced pressure, and the residue is purified by silica gel column chromatography (eluent: gradient from 0% to 100% hexane/ethyl acetate) to give the desired compound (6.2 g).

REFERENCE EXAMPLE 2

Preparation of 3-(cyclohexen-1-yl)aniline (Intermediate 2)

(1) Cyclohexanone (1 ml) and 2,6-di-tert-butyl-4-methylpyridine (2.4 g) are dissolved in methylene chloride (10 ml), and thereto is added trifluoromethanesulfonic anhydride (1.8 ml), and the mixture is stirred at room temperature for 18 hours. The insoluble materials are removed by filtration, and the filtrate is evaporated under reduced pressure. The residue is purified by silica gel column chromatography (eluent: gradient from 0% to 100% hexane/ethyl acetate) to give (cyclohexen-1-yl)trifluoromethyl sulfonate (1.3 g).

(2) The above product (1.3 g) is dissolved in ethylene glycol dimethyl ether (10 ml), and thereto are added 3-nitrophenylboronic acid (1.3 g), tetrakis(triphenylphosphine)palladium (0) (330 mg), lithium chloride (720 mg) and 2M aqueous sodium carbonate (8 ml), and the mixture is heated under reflux for 3 hours. To the mixture is added ethyl acetate, and the organic layer is washed with water, and the solvent is evaporated under reduced pressure. The residue is purified by silica gel column chromatography (eluent: gradient from 0% to 100% hexane/ethyl acetate) to give 3-(cyclohexen-1-yl)-1-nitrobenzene (700 mg).

(3) The above product (100 mg) is dissolved in ethanol (5 ml), and thereto are added reduced iron (140 mg), ammonium chloride (53 mg) and water (5 ml), and the mixture is heated under reflux for one hour. The insoluble materials are removed by filtration, and the solvent is evaporated under reduced pressure. The residue is purified by silica gel column chromatography (eluent: gradient from 0% to 100% hexane/ethyl acetate) to give the desired compound (60 mg).

REFERENCE EXAMPLE 3

Preparation of 3-cyclohexylaniline (Intermediate 3)

3-(Cyclohexen-1-yl)-1-nitrobenzene(7.5 g) is dissolved in ethanol (150 ml), and thereto is added 10% palladium on carbon (750 mg), and the mixture is subjected to catalytic hydrogenation at 25° C. The catalyst is removed by filtration, and the solvent is evaporated under reduced pressure. The residue is purified by silica gel column chromatography (eluent: gradient from 0% to 100% hexane/ethyl acetate) to give the desired compound (5.1 g).

REFERENCE EXAMPLE 4

Preparation of 4-[2-(tert-butoxycarbonylamino)ethoxy]-N-(3-iodophenyl)-3-methoxyphenylacetamide (Intermediate 4)

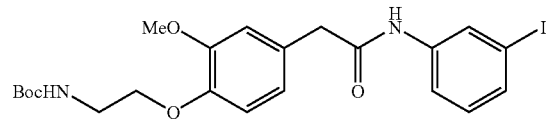

A mixture of Intermediate 1 (8.4 g), 1,2-dibromethane (160 ml), 40% aqueous potassium hydroxide solution (45 ml) and 40% aqueous tetrabutylammonium hydroxide solution (4.5 ml) is heated with stirring at 40° C. for 18 hours. The reaction solution is washed with water, and the organic layer is dried over sodium sulfate, and the solvent is evaporated under reduced pressure. The residue is dissolved in dimethylformamide (45 ml), and thereto is added potassium phthalimide (1.9 g). The mixture is stirred at 50° C. for 18 hours. The reaction solution is poured into ice-water, and the mixture is extracted with chloroform. The extract is washed with water, and the solvent is evaporated under reduced pressure. The residue is dissolved in ethanol (50 ml), and thereto is added hydrazine monohydrate (600 mg), and heated under reflux for 3 hours. The insoluble materials are removed by filtration, and the filtrate is concentrated, extracted with chloroform, washed with water, and the solvent is evaporated under reduced pressure. The residue is dissolved in chloroform (50 ml) and thereto is added di-tert-butyl dicarbonate (4.3 g). The mixture is stirred at 25° C. for 18 hours, and the solvent is evaporated under reduced pressure. The residue is purified by silica gel column chromatography (eluent: gradient from 0% to 100% hexane/ethyl acetate) to give the desired compound (5.2 g).

REFERENCE EXAMPLE 5

Preparation of 4-(2-bromoethoxy)-N-[3-(4-tert-butylcyclohexan-1-yl)phenyl]-3-methoxyphenylacetamide (Intermediate 5)

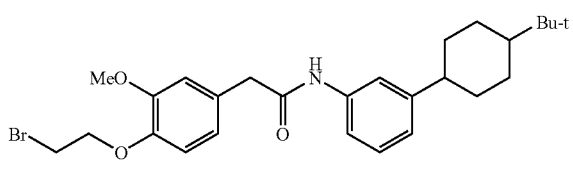

A mixture of N-[3-(4-tert-butylcyclohexan-1-yl)phenyl]-4-hydroxy-3-methoxyphenylacetamide (the compound of Example 20) (1.5 g), 1,2-dibromethane (15 ml), 40% aqueous potassium hydroxide solution (5 ml) and 40% aqueous tetrabutylammonium hydroxide solution (0.5 ml) is stirred at 50° C. for 18 hours. The reaction solution is washed with water, and the organic layer is dried over sodium sulfate, and the solvent is evaporated under reduced pressure. The residue is purified by silica gel column chromatography (eluent: gradient from 0% to 100% hexane/ethyl acetate) to give the desired compound (1.6 g).

REFERENCE EXAMPLE 6

Preparation of 4-[2-(tert-butoxycarbonylamino)ethoxy]-N-[3-(4,4,5,5-tetramethyl-1,3-dioxaboran-2-yl)phenyl]-3-methoxyphenylacetamide (Intermediate 6)

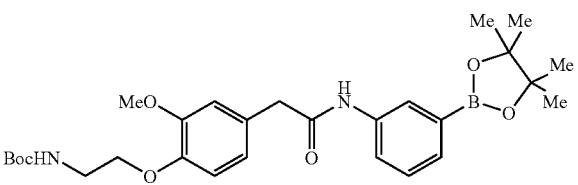

Intermediate 4 (4.2 g) is dissolved in dimethylformamide (42 ml), and thereto are added bis(pinacolato)diboron (6 g), potassium acetate (2.35 g), 1,1'-bis(diphenylphosphino)ferrocene dichloropalladium complex (652 mg), and the mixture is heated with stirring at 80° C. for 24 hours under argon atmosphere. To the reaction solution is added ethyl acetate, and the mixture is washed with water, 1 M aqueous sodium hydroxide solution, and the organic layer is dried over sodium sulfate. The solvent is evaporated under reduced pressure, and the residue is purified by silica gel column chromatography (eluent: gradient from 0% to 100% hexane/ethyl acetate) to give the desired compound (4 g).

REFERENCE EXAMPLE 7

Preparation of 4-[2-(tert-butoxycarbonylamino) ethoxy]-3-methoxyphenylacetic acid pentafluorophenyl ester (Intermediate 7)

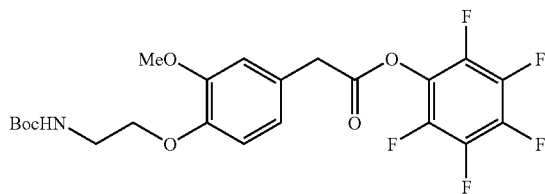

(1) 4-(2-Azidoethoxy)-3-methoxyphenylacetic acid methyl ester (72 g), which is prepared by the method disclosed in EP 0721939, is dissolved in ethanol (1 L), and thereto is added 10% palladium on carbon (5 g), and the mixture is subjected to catalytic hydrogenation at 25° C. The catalyst is removed by filtration, and the solvent is evaporated under reduced pressure to give 4-(2-aminoethoxy)-3-methoxyphenylacetic acid methyl ester. This product is dissolved in chloroform (500 ml), and thereto is added di-tert-butyl dicarbonate (90 g), and the mixture is stirred at 25° C. for 18 hours. The solvent is evaporated under reduced pressure, and the residue is purified by silica gel column chromatography (eluent: gradient from 0% to 100% hexane/ethyl acetate) to give 4-[2-(tert-butoxycarbonylamino) ethoxy]-3methoxyphenylacetic acid methyl ester (43.7 g).

(2) The above ester compound is dissolved in methanol (350 ml), and thereto is added 1 M aqueous sodium hydroxide solution (350 ml), and the mixture is stirred at 25° C. for 18 hours. The solvent is evaporated under reduced pressure, and the residue is acidified with acetic acid, and the mixture is extracted with ethyl acetate. The solvent is evaporated under reduced pressure, and the residue is dissolved in methylene chloride (500 ml), and thereto are added pentafluorophenol (22 g) and 1-ethyl-3-(3-dimethylaminopropyl)carbodiimide hydrochloride (23 g). The mixture is stirred at 25° C. for 18 hours, and the reaction solution is washed with water, and the solvent is evaporated under reduced pressure, and the residue is purified by silica gel column chromatography (eluent: gradient from 0% to 100% hexane/ethyl acetate) to give the desired compound (42.3 g).

REFERENCE EXAMPLE 8

Preparation of 7-amino-1-oxo-2-(2-pyridylmethyl)-1,2,3,4-tetrahydronaphthalene (Intermediate 8)

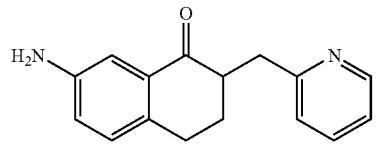

(1) 7-Nitro-1-tetralone (500 mg), pyridine-2-aldehyde (315 mg), piperidine (0.15 ml) and acetic acid (0.4 ml) are dissolved in toluene (10 ml), and the mixture is heated under reflux for 12 hours. The reaction solution is washed with water, and the organic layer is dried over sodium sulfate. The solvent is evaporated under reduced pressure. The residue is purified by silica gel chromatography (eluent: gradient from 0% to 100% hexane/ethyl acetate) to give 7-nitro-1-oxo-2-(2-pyridylmethylidene)-1,2,3,4-tetrahydronaphthalene (140 mg).

(2) The above product (140 mg) is dissolved in ethanol (5 ml), and thereto is added 10% palladium on carbon (20 mg), and the mixture is subjected to catalytic hydrogenation at 25° C. The catalyst is removed by filtration, and the solvent is evaporated. The residue is purified by silica gel column chromatography (eluent: gradient of 0% to 100% hexane/ethyl acetate) to give Intermediate 8 (35 mg).

REFERENCE EXAMPLE 9

Preparation of 6-amino-N-benzylindole (Intermediate 9)

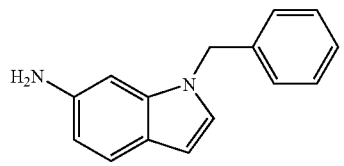

(1) 6-Nitroindole (1.0 g) and benzyl chloride (2.2 g) are dissolved in dimethylsulfoxide (10 ml), and thereto is added potassium hydroxide (1.0 g), and the mixture is stirred at room temperature for 12 hours. To the mixture is added ethyl acetate, and the organic layer is washed with water, dried over sodium sulfate, and the solvent is evaporated under reduced pressure. The residue is purified by silica gel column chromatography (eluent: gradient from 0% to 100% hexane/ethyl acetate) to give N-benzyl-6-nitroindole (1.4 g).

(2) The above product (1.4 g) is dissolved in ethanol (20 ml), and thereto are added reduced iron (1.7 g), ammonium chloride (660 mg) and water (10 ml), and the mixture is heated under reflux for one hour. The insoluble materials are removed by filtration, and the solvent is evaporated under reduced pressure. The residue is purified by silica gel column chromatography (eluent: gradient from 0% to 100% hexane/ethyl acetate) to give the title compound (660 mg).

EXAMPLE 1

Preparation of N-(3-cyclohexylphenyl)-4-hydroxy-3-methoxyphenylacetamide

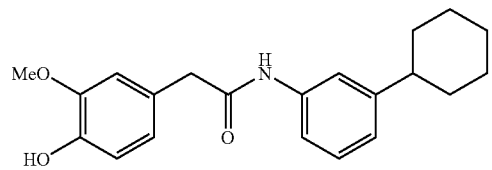

Intermediate 1 (850 mg) and tetrakis(triphenylphosphine)-palladium (0) (250 mg) are dissolved in tetrahydrofuran (16 ml), and thereto is added a 0.5 M tetrahydrofuran solution (20 ml) of cyclohexylzinc bromide under argon atmosphere at room temperature, and the mixture is stirred for 18 hours. A saturated aqueous ammonium chloride solution is added to the reaction solution, and the mixture is extracted with ethyl acetate. The organic layer is dried over sodium sulfate, and the solvent is evaporated under reduced pressure. The residue is purified by silica gel column chromatography (eluent: gradient from 0% to 100% hexane/ethyl acetate) to give the desired compound (120 mg).

$^1$H-NMR (300 MHz, CDCl$_3$, δ): 1.18–1.85 (10H, m), 2.45 (1H, m), 3.65 (2H, s), 3.90 (3H, s), 5.67 (1H, s), 6.81–6.82 (2H, m), 6.93 (1H, s), 6.95 (1H, d), 7.07 (1H, s), 7.17–7.25 (3H, m).

EXAMPLES 2 TO 6

Using various zinc bromides instead of cyclohexyl zinc bromide in Example 1, the compounds as listed in Table 7 are obtained in a similar manner to Example 1.

TABLE 7

| Ex. No. | R$^4$ |
|---|---|
| 2 | benzyl |
| 3 | adamantyl |
| 4 | cyclopentylmethyl |
| 5 | cyclohexylmethyl |
| 6 | n-butyl (—CH$_2$CH$_2$CH$_2$Me) |

EXAMPLES 7 TO 8

Instead of 4-hydroxy-N-(3-iodophenyl)-3-methoxyphenylacetamide (Intermediate 1) in Example 1, various phenylacetamide derivatives are treated in a similar manner to Example 1 to give the compounds as listed in Table 8.

TABLE 8

| Ex. No. | R$^1$ |
|---|---|
| 7 | F |
| 8 | Cl |

EXAMPLE 9

Preparation of N-[3-(cyclohexen-1-yl)phenyl]-4-hydroxy-3-methoxyphenylacetamide

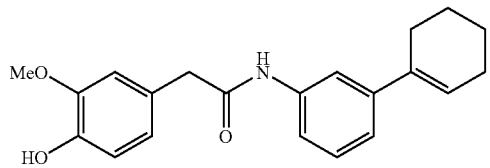

4-Hydroxy-3-methoxyphenylacetic acid pentafluorophenyl ester (60 mg) and Intermediate 2 (60 mg) are dissolved in ethyl acetate, and the mixture is stirred at 60° C. for 18 hours. The solvent is evaporated under reduced pressure, and the residue is purified by silica gel column chromatography (eluent: gradient from 0% to 100% hexane/ethyl acetate) to give the title compound (50 mg).

$^1$H-NMR (300 MHz, CDCl$_3$, δ): 1.63 (2H, m), 1.75 (2H, m), 2.17 (2H, m), 2.35 (2H, m), 3.67 (2H, s), 3.90 (3H, s), 5.65 (1H, s), 6.08 (1H, s), 6.82 (2H, m), 6.95 (1H, d), 7.05–7.15 (2H, m), 7.17–7.38 (3H, m).

EXAMPLES 10 TO 28

Instead of 3-(cyclohexen-1-yl)aniline (Intermediate 2) in Example 9, various aniline derivatives are treated in a similar manner to Example 9 to give the compounds as listed in Table 9, Table 10 and Table 11.

TABLE 9

| Ex. No. | R$^4$ |
|---|---|
| 10 | methylcycloheptanone |
| 11 | 2-phenylcyclohexyl |
| 12 | 4-methyl-phenylcyclohexyl |
| 13 | 4-methylcyclohexylmethyl |

TABLE 9-continued

[Structure: MeO, HO-phenyl-CH2-C(=O)-NH-phenyl-R4 (meta)]

| Ex. No. | R4 |
|---------|-----|
| 14 | 3-methylcyclohexanone |
| 15 | methoxycyclohexane |
| 16 | N-methylpiperidine |
| 17 | acetophenone |
| 18 | acetyl (C(=O)Me) |
| 19 | ethynyl (C≡CH) |
| 20 | 4-methyl-1-t-butylcyclohexane |

TABLE 10

[Structure: MeO, HO-phenyl-CH2-C(=O)-NH-phenyl-R4 (para)]

| Ex. No. | R4 |
|---------|-----|
| 21 | benzyl/ethylphenyl |
| 22 | styryl (CH=CH-Ph) |
| 23 | propyl (CH2CH2CH2Me) |

TABLE 10-continued

[Structure: MeO, HO-phenyl-CH2-C(=O)-NH-phenyl-R4 (para)]

| Ex. No. | R4 |
|---------|-----|
| 24 | 4-chloro-methoxyphenyl ether |
| 25 | 1-methylimidazol-yl |
| 26 | methyl-N=N-phenyl (methylazophenyl) |

TABLE 11

| Ex. No. | Compound |
|---------|----------|
| 27 | [Structure: MeO, HO-phenyl-CH2-C(=O)-NH-(2-Me, 5-(C≡C-Ph))phenyl] |
| 28 | [Structure: MeO, HO-phenyl-CH2-C(=O)-NH-(2-O-Ph)phenyl] |

EXAMPLES 29 TO 32

Instead of 4-hydroxy-3-methoxyphenylacetic acid pentafluorophenyl ester and Intermediate 2 in Example 9, various pentafluorophenyl esters and Intermediate 3 are used respectively, and treated in a similar manner to Example 9 to give the compounds as listed in Table 12.

TABLE 12

[Structure: R1, HO, R3-phenyl-CH2-C(=O)-NH-(3-cyclohexyl)phenyl]

| Ex. No. | R1 | R3 |
|---------|------|------|
| 29 | NO2 | H |
| 30 | MeO | Ph |
| 31 | t-Bu | t-Bu |
| 32 | MeO | CHO |

EXAMPLE 33

Preparation of 3-amino-4-benzyloxy-N-(3-cyclohexylphenyl)phenylacetamide

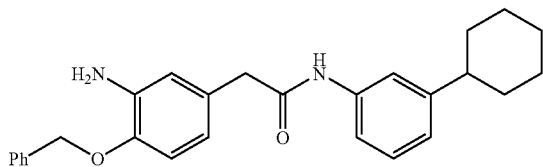

A mixture of N-(3-cyclohexylphenyl)-4-hydroxy-3-nitrophenylacetamide (the compound of Example 29) (300 mg), benzyl bromide (287 mg), potassium carbonate (500 mg) and acetone (10 ml) is heated under reflux for 18 hours. After cooling, water is added to the mixture, and the mixture is extracted with ethyl acetate. The organic layer is dried over sodium sulfate, and the solvent is evaporated under reduced pressure. The residue is purified by silica gel column chromatography (eluent: gradient from 0% to 100% hexane/ethyl acetate) to give 4-benzyloxy-N-(3-cyclohexylphenyl)-3-nitrophenylacetamide (320 mg). This product is dissolved in ethanol (5 ml), and thereto are added reduced iron (200 mg), ammonium chloride (80 mg) and water (5 ml), and the mixture is heated under reflux for one hour. The reaction solution is filtered through Celite, and the filtrate is concentrated, and the residue is dissolved in chloroform. The organic layer is washed with water, dried over sodium sulfate, and the solvent is evaporated under reduced pressure. The residue is purified by silica gel column chromatography (eluent: gradient from 0% to 100% hexane/ethyl acetate) to give the desired compound (240 mg).

$^1$H-NMR (300 MHz, CDCl$_3$, δ): 1.20–1.45 (5H, m), 1.70–1.90 (5H, m), 2.44 (1H, m), 3.59 (2H, s), 5.10 (2H, s), 6.63 (1H, dd), 6.69 (1H, d), 6.86 (1H, d), 6.92 (1H, d), 7.10 (1H, m), 7.18–7.24 (3H, m), 7.30–7.46 (5H, m).

EXAMPLE 34

Preparation of N-(3-cyclohexylphenyl)-4-hydroxy-3-(methanesulfonylamino)phenylacetamide

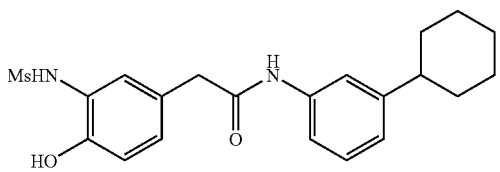

3-Amino-4-benzyloxy-N-(3-cyclohexylphenyl)phenylacetamide (the compound of Example 33) (200 mg) is dissolved in pyridine (5 ml), and thereto is added dropwise methanesulfonyl chloride (111 mg), and the mixture is stirred for 0.5 hour. Water is added to the mixture, and the mixture is extracted with ethyl acetate. The organic layer is dried under sodium sulfate, and the solvent is evaporated under reduced pressure. The residue is purified by silica gel column chromatography (eluent: gradient from 0% to 100% hexane/ethyl acetate) to give 4-benzyloxy-N-(3-cyclohexylphenyl)-3-methanesulfonylaminophenyl-acetamide (200 mg). This product is dissolved in ethanol (10 ml), and thereto is added 10% palladium on carbon (20 mg). The mixture is subjected to catalytic hydrogenation at 25° C. The catalyst is removed by filtration, and the solvent is evaporated under reduced pressure. The residue is purified by silica gel column chromatography (eluent: gradient from 0% to 10% chloroform/methanol) to give the desired compound (120 mg).

$^1$H-NMR (300 MHz, DMSO-d$_6$, δ): 1.20–1.46 (5H, m), 1.65–1.85 (5H, m), 2.42 (1H, m), 2.94 (3H, s), 3.46 (2H, s), 6.82 (1H, d), 6.87 (1H, d), 6.99 (1H, dd), 7.13–7.19 (2H, m), 7.36 (1H, d), 7.46 (1H, s), 9.99 (1H, s).

EXAMPLE 35

Preparation of 4-hydroxy-3-methoxy-N-(3-phenylphenyl)phenylacetamide

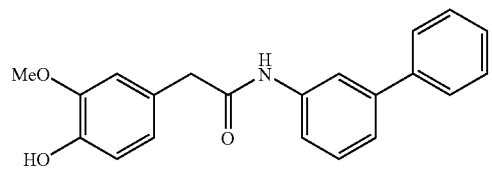

Intermediate 1 (500 mg), phenylboronic acid (300 mg), tetrakis(triphenylphosphine)palladium (0) (150 mg) are dissolved in tetrahydrofuran (20 ml), and thereto are added cesium carbonate (850 mg) and water (10 ml). The mixture is heated under reflux for 18 hours under argon atmosphere. The reaction solution is extracted with ethyl acetate, and the organic layer is dried over sodium sulfate, and the solvent is evaporated under reduced pressure. The residue is purified by silica gel column chromatography (eluent: gradient from 0% to 100% hexane/ethyl acetate) to give the desired compound (360 mg).

$^1$H-NMR (300 MHz, CDCl$_3$, δ): 3.69 (2H, s), 3.91 (3H, s), 5.65 (1H, s), 6.81–6.87 (2H, m), 6.96 (1H, d), 7.16 (1H, s), 7.29–7.50 (6H, m), 7.56 (2H, m), 7.62 (1H, s).

EXAMPLE 36

Preparation of 4-hydroxy-3-methoxy-N-[3-(2-phenylethynyl)phenyl]-phenylacetamide

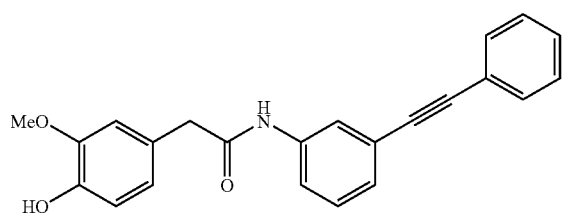

A mixture of Intermediate 1 (2.5 g), ethynylbenzene (800 mg), copper (I) iodide (124 mg), bis(triphenylphosphine)palladium (II) dichloride (1.37 g), triethylamine (19.0 g) and acetonitrile (20 ml) is heated with stirring at 50° C. under argon atmosphere. The solvent is evaporated under reduced pressure, and the residue is purified by silica gel column chromatography (eluent: gradient from 0% to 100% hexane/ethyl acetate) to give the desired compound (1.8 g).

$^1$H-NMR (300 MHz, CDCl$_3$, δ): 3.68 (2H, s), 3.91 (3H, s), 5.67 (1H, s), 6.82–6.84 (2H, m), 6.96 (1H, d), 7.10 (1H, s), 7.25–7.35 (5H, m), 7.46–7.53 (4H, m).

EXAMPLE 37

Preparation of 4-hydroxy-3-methoxy-N-[3-[2-(2-trifluoromethylphenyl)-ethynyl]phenyl]phenylacetamide

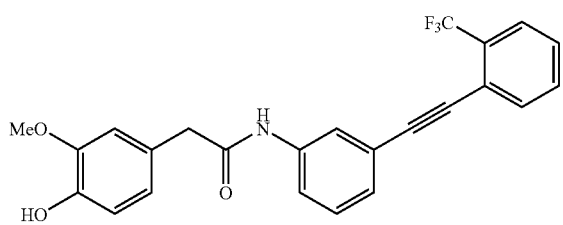

A mixture of N-(3-ethynylphenyl)-4-hydroxy-3-methoxypheny-acetamide (the compound of Example 19) (200 mg), 1-trifluoromethyl-2-iodobenzene (280 mg), copper (I) iodide (19 mg), bis(triphenylphosphine)palladium (II) dichloride (70 mg), triethylamine (1 g) and acetonitrile (3 ml) is heated with stirring at 50° C. under argon atmosphere for 18 hours. The solvent is evaporated under reduced pressure, and the residue is purified by silica gel column chromatography (eluent: gradient from 0% to 100% hexane/ethyl acetate) to give the desired compound (120 mg).

$^1$H-NMR (300 MHz, CDCl$_3$, δ): 3.68 (2H, s), 3.92 (3H, s), 5.65 (1H, s), 6.83 (2H, m), 6.96 (1H, d), 7.11 (1H, s), 7.25–7.35 (2H, m), 7.42 (1H, m), 7.44–7.60 (3H, m), 7.52–7.71 (2H, m).

EXAMPLES 38 TO 53

Instead of 1-trifluoromethyl-2-iodobenzene in Example 37, various iodobenzene derivatives are treated in a similar manner to Example 37 to give the compounds as listed in Table 13.

TABLE 13

| Ex. No. | R$^8$ |
|---|---|
| 38 | 3-Me-phenyl |
| 39 | 2,6-diMe-phenyl (2,3-diMe) |
| 40 | 2-OMe-phenyl |
| 41 | 3-OMe-phenyl |
| 42 | 3-(OCH$_2$Ph)-phenyl |
| 43 | 2-Ph-phenyl |
| 44 | 2-CH$_2$Ph-phenyl |
| 45 | 3-F-phenyl |
| 46 | 2-F-phenyl |
| 47 | 4-F-phenyl |
| 48 | 2-Cl-phenyl |
| 49 | 3-Cl-phenyl |
| 50 | 4-CF$_3$-phenyl |

TABLE 13-continued

[Structure: MeO, HO-phenyl-CH2-C(=O)-NH-phenyl-C≡C-R8]

| Ex. No. | R8 |
|---|---|
| 51 | [3-methylphenyl with CF3] |
| 52 | [methylnaphthalene] |
| 53 | [methylfluorene] |

EXAMPLE 54

Preparation of 4-hydroxy-3-methoxy-N-[3-(2-phenylethyl)phenyl]-phenylacetamide

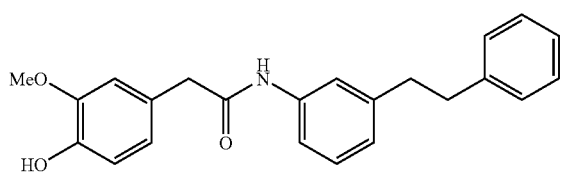

4-Hydroxy-3-methoxy-N-[3-(2-phenylethynyl)phenyl]phenylacetamide (the compound of Example 36) (250 mg) is dissolved in ethyl acetate (10 ml), and thereto is added 10% palladium on carbon (25 mg), and the mixture is subjected to catalytic hydrogenation at 25° C. The catalyst is removed by filtration, and the solvent is evaporated under reduced pressure. The residue is purified by silica gel column chromatography (eluent: gradient from 0% to 100% hexane/ethyl acetate) to give the desired compound (200 mg).

$^1$H-NMR (300 MHz, CDCl$_3$, δ): 2.86 (4H, s), 3.66 (2H, s), 3.90 (3H, s), 5.68 (1H, s), 6.81–7.01 (4H, m), 6.96 (1H, s), 7.09–7.42 (7H, m), 7.72 (1H, d).

EXAMPLE 55

Preparation of 4-hydroxy-3-methoxy-N-[4-(2-phenylethyl)phenyl]phenylacetamide

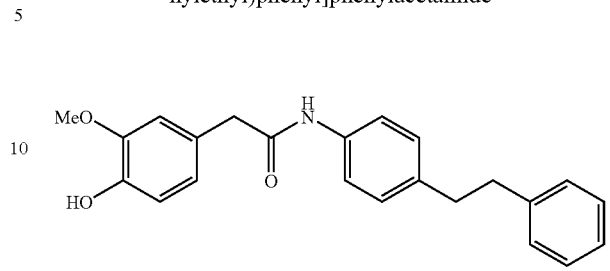

Instead of the compound of Example 36, the compound of Example 22 is treated in a similar manner to Example 54 to give the desired compound.

EXAMPLE 56

Preparation of 4-hydroxy-3-methoxy-N-[3-[(Z)-2-phenylvinyl]phenyl]-phenylacetamide

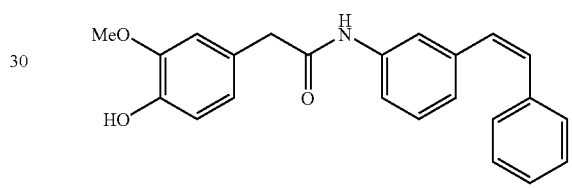

4-Hydroxy-3-methoxy-N-[3-(2-phenylethynyl)phenyl]phenylacetamide (150 mg) obtained in Example 36 is dissolved in ethyl acetate (10 ml), and thereto is added Lindlar catalyst (5% lead-poisoned palladium-calcium carbonate) (15 mg), and the mixture is subjected to catalytic hydrogenation at 25° C. The catalyst is removed by filtration, and the solvent is evaporated under reduced pressure. The residue is purified by silica gel column chromatography (eluent: gradient from 0% to 100% hexane/ethyl acetate) to give the desired compound (50 mg).

$^1$H-NMR (300 MHz, CDCl$_3$, δ): 3.62 (2H, s), 3.88 (3H, s), 5.68 (1H, s), 6.51 (1H, d), 6.59 (1H, d); 6.76–7.26 (12H, m), 7.44 (1H, d).

EXAMPLE 57

Preparation of N-[3-(N-cyclohexylcarbamoyl)phenyl]-4-hydroxy-3-methoxyphenylacetamide

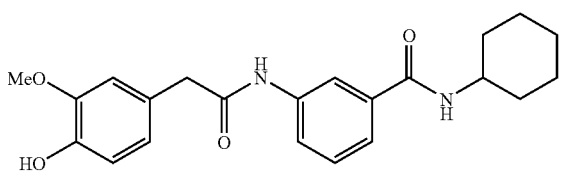

A mixture of N-(3-carboxyphenyl)-4-hydroxy-3-methoxyphenylacetamide (500 mg), pentafluorophenol (305 mg), 1-ethyl-3-(3-dimethylaminopropyl)carbodiimide hydrochloride (320 mg) and methylene chloride (10 ml) is stirred at 25° C. for 18 hours. The reaction solution is washed with water, and the solvent is evaporated under reduced pressure. To the residue are added ethyl acetate (10 ml) and cyclohexylamine (174 mg), and the mixture is heated with stirring at 60° C. for 18 hours. The solvent is evaporated and the residue is purified by silica gel column chromatography (eluent: gradient from 0% to 100% hexane/ethyl acetate) to give the desired compound (600 mg).

$^1$H-NMR (300 MHz, CDCl$_3$, δ): 1.17–1.51 (4H, m), 1.63–1.88 (4H, m), 1.95–2.07 (2H, m), 3.68 (2H, s), 3.90 (3H, s), 3.94 (1H, m), 5.70 (1H, s), 6.03 (1H, d), 6.81 (2H, m), 6.94 (1H, d), 7.32–7.46 (3H, m), 7.68 (1H, d), 7.74 (1H, s).

EXAMPLE 58

Preparation of 4-(2-aminoethoxy)-N-(3-cycloheptylphenyl)-3-methoxyphenylacetamide hydrochloride

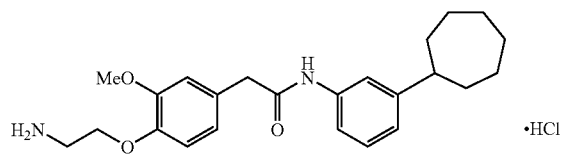

3-Methoxy-4-(2-phthalimidoethoxy)phenylacetic acid pentafluorophenyl ester (690 mg) and 3-cycloheptylaniline (500 mg) are dissolved in ethyl acetate (10 ml), and the mixture is heated with stirring at 60° C. for 18 hours. The solvent is evaporated under reduced pressure, and the residue is purified by silica gel column chromatography (eluent: gradient from 0% to 100% hexane/ethyl acetate) to give N-(3-cycloheptylphenyl)-3-methoxy-4-(2-phthalimidoethoxy)phenylacetamide (500 mg). This product is dissolved in ethanol (10 ml), and thereto is added hydrazine monohydrate (610 mg), and the mixture is heated under reflux for 2 hours. The insoluble materials are removed by filtration, and the solvent is evaporated under reduced pressure. To the residue is added water, and the mixture is extracted with chloroform. The organic layer is dried over sodium sulfate, and the residue is purified by silica gel column chromatography (eluent: gradient from 0% to 30% chloroform/methanol), and treated with 10% hydrogen chloride-methanol to give the desired compound (170 mg).

$^1$H-NMR (300 MHz, DMSO-d$_6$, δ): 1.47–1.82 (12H, m), 2.60 (1H, m), 3.16 (2H, t), 3.57 (2H, s), 3.78 (3H, s), 4.13 (2H, t), 6.86 (2H, m), 7.00 (2H, m), 7.16 (1H, t), 7.39 (1H, d), 7.48 (1H, s), 8.12 (3H, s), 10.17 (1H, s).

EXAMPLES 59 TO 62

Instead of 3-cycloheptylaniline in Example 58, the corresponding compounds are treated in a similar manner to Example 58 to give the compounds as listed in Table 14.

TABLE 14

![structure with MeO, H2N, HN, R4, HCl]

| Ex. No. | R$^4$ |
|---|---|
| 59 | phenylethynyl group |
| 60 | phenylethyl group |
| 61 | cyclohexyl group |
| 62 | 4-tert-butylcyclohexyl group |

EXAMPLE 63

Preparation of 4-(2-aminoethoxy)-3-methoxy-N-(3-phenylphenyl)phenylacetamide hydrochloride

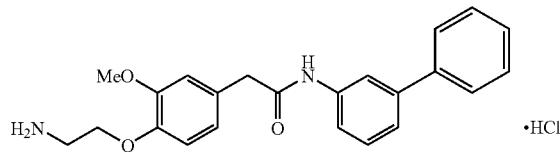

Intermediate 4 (500 mg) is dissolved in tetrahydrofuran (10 ml), and thereto are added tetrakis(triphenylphosphine)palladium (0) (110 mg), phenylboronic acid (230 mg), cesium carbonate (1.2 g) and water (2 ml), and the mixture is heated under reflux for 18 hours under argon atmosphere. The solvent is evaporated under reduced pressure, and the residue is purified by silica gel column chromatography (eluent: gradient from 0% to 100% hexane/ethyl acetate) to give 4-[2-(tert-butoxycarbonylamino)ethoxy]-3-methoxy-N-(3-phenylphenyl)phenylacetamide (350 mg). This product is treated with 10% hydrogen chloride-methanol to give the desired compound (210 mg).

$^1$H-NMR (300 MHz, DMSO-d$_6$, δ): 3.18 (2H, t), 3.61 (2H, s), 3.79 (3H, s), 4.11 (2H, t), 6.88 (1H, m), 7.01 (2H, m), 7.30–7.50 (5H, m), 7.60 (3H, m), 7.85–8.00 (4H, m), 10.25 (1H, s).

EXAMPLES 64 TO 68

Instead of phenylboronic acid in Example 63, various boronic acid derivatives are treated in a similar manner to Example 63 to give the compounds as listed in Table 15.

TABLE 15

MeO, H₂N-CH₂CH₂-O-C₆H₃-CH₂-C(O)-NH-C₆H₄-R⁴ · HCl

| Ex. No. | R⁴ |
|---|---|
| 64 | 4-(Bu-t)-phenyl |
| 65 | 4-(COOMe)-phenyl |
| 66 | 3-F-phenyl |
| 67 | 4-Cl-phenyl |
| 68 | 3-Me-phenyl |

EXAMPLE 69

Preparation of 4-acetoxy-N-[3-(4-tert-butylcyclohexan-1-yl)phenyl]-3-methoxyphenylacetamide

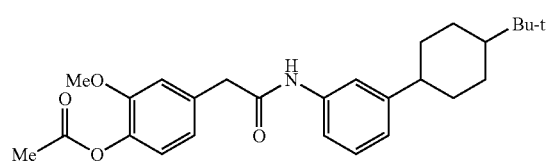

N-[3-(4-tert-Butylcyclohexan-1-yl)phenyl]-4-hydroxy-3-methoxyphenylacetamide (100 mg) obtained in Example 20, triethylamine (94 mg) and 4-dimethylaminopyridine (5 mg) are dissolved in methylene chloride (5 ml), and thereto is added dropwise acetyl chloride (40 mg) under ice-cooling. The mixture is stirred at 25° C. for 18 hours, and the reaction solution is washed with water. The organic layer is dried over sodium sulfate, and the solvent is evaporated under reduced pressure. The residue is purified by silica gel column chromatography (eluent: gradient from 0% to 100% hexane/ethyl acetate) to give the desired compound (90 mg).

$^1$H-NMR (300 MHz, CDCl$_3$, δ): 0.78, 0.86 (9H, m), 1.0–1.25 (3H, m), 1.30–1.93 (5H, m), 2.20 (1H, m), 2.32 (3H, s), 2.40, 2.98 (1H, m), 3.70 (2H, s), 3.83 (3H, s), 6.83–7.42 (8H, m).

EXAMPLES 70 TO 71

Instead of acetyl chloride in Example 69, various acyl chloride derivatives are treated in a similar manner to Example 69 to give the compounds as listed in Table 16.

TABLE 16

| Ex. No. | Compound |
|---|---|
| 70 | PhO-C(O)-O-C₆H₃(OMe)-CH₂-C(O)-NH-C₆H₄-(4-tert-butylcyclohexyl) |
| 71 | t-Bu-O-C(O)-O-C₆H₃(OMe)-CH₂-C(O)-NH-C₆H₄-(4-tert-butylcyclohexyl) |

EXAMPLE 72

Preparation of N-[3-(4-tert-butylcyclohexan-1-yl)phenyl]-4-carboxy-methyloxy-3-methoxyphenylacetamide

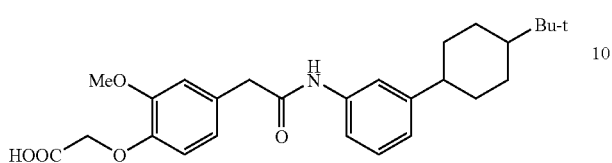

N-[3-(4-tert-butylcyclohexan-1-yl)phenyl]-4-hydroxy-3-methoxyphenylacetamide (130 mg) and ethyl bromoacetate (84 mg) are dissolved in acetone, and thereto is added potassium carbonate (180 mg), and the reaction solution is heated under reflux for 18 hours. The reaction solution is filtered, and the filtrate is concentrated. The residue is purified by silica gel column chromatography (eluent: gradient from 0% to 100% hexane/ethyl acetate) to give N-[3-(4-tert-butylcyclohexan-1-yl)phenyl]-4-ethoxycarbonylmethyloxy 3-methoxyphenylacetamide (120 mg). This product is dissolved in methanol (2 ml), and thereto is added 2 M aqueous sodium hydroxide solution (1 ml), and the mixture is stirred at 25° C. for 1 hour. The mixture is neutralized with acetic acid, and water is added thereto. The mixture is extracted with chloroform, and the organic layer is dried over sodium sulfate. The solvent is evaporated under reduced pressure, and the residue is purified by silica gel column chromatography (eluent: gradient from 0% to 25% chloroform/methanol) to give the desired compound (45 mg).

$^1$H-NMR (300 MHz, CDCl$_3$, δ): 0.79, 0.87 (9H, m), 1.05–1.95 (8H, m), 2.20 (1H, m), 2.38, 2.98 (1H, m), 3.68 (2H, s), 3.90 (3H, s), 4.69 (2H, s), 6.84–7.44 (8H, m).

EXAMPLE 73

Preparation of N-[3-(4-tert-butylcyclohexan-1-yl)phenyl]-4-[2-[N-(2-hydroxyethyl)amino]ethoxy]-3-methoxyphenylacetamide

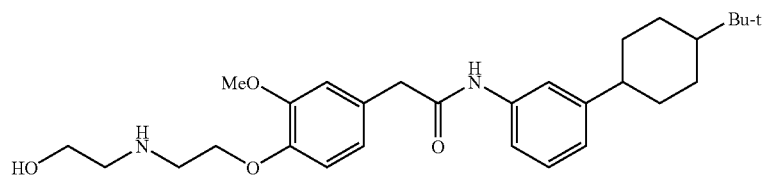

Intermediate 5 (200 mg), 2-aminoethanol (122 mg) and triethylamine (45 mg) are dissolved in acetonitrile (5 ml), and the mixture is heated under reflux for 18 hours. To the reaction solution is added chloroform, and the mixture is washed with water. The organic layer is dried over sodium sulfate, and the solvent is evaporated under reduced pressure. The residue is purified by silica gel column chromatography (eluent: gradient from 0% to 20% chloroform/methanol) to give the desired compound (170 mg).

$^1$H-NMR (300 MHz, CDCl$_3$, δ): 0.79, 0.87 (9H, m), 1.05–2.25 (9H, m), 2.40, 2.98 (1H, m), 2.90 (2H, t), 3.10 (2H, t), 3.68 (2H, s), 3.71 (2H, t), 3.86 (3H, s), 4.16 (2H, t), 6.81–7.42 (8H, m).

EXAMPLE 74

Preparation of N-[3-(4-tert-butylcyclohexan-1-yl)phenyl]-3-methoxy-4-[2-(N-methylamino)ethoxy]phenylacetamide

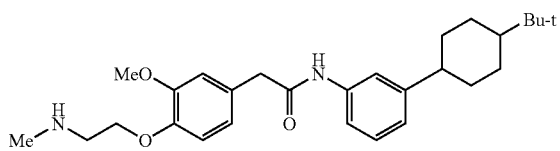

Instead of 2-aminoethanol in Example 73, methylamine is treated in a similar manner to Example 73 to give the desired compound.

EXAMPLE 75

Preparation of N-[3-(4-tert-butylcyclohexan-1-yl)phenyl]-4-[2-(N-formylamino)ethoxy]-3-methoxyphenylacetamide

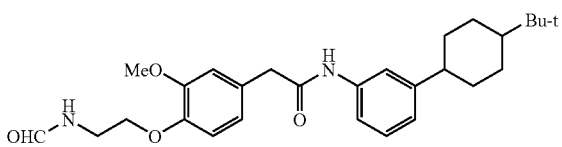

Formic acid (30 mg) is slowly added to acetic anhydride (75 mg), and the mixture is heated with stirring at 60° C. for 2 hours. To the mixture is added dry tetrahydrofuran (0.2 ml), and further added 4-(2-aminoethoxy)-N-[3-(4-tert-butylcyclohexan-1-yl)phenyl]-3-methoxyphenylacetamide (100 mg) obtained in Example 62 at −20° C. The mixture is stirred at room temperature for 3 hours. The solvent is evaporated under reduced pressure, and the residue is purified by silica gel column chromatography (eluent: gradient from 0% to 100% hexane/ethyl acetate) to give the desired compound (80 mg).

$^1$H-NMR (300 MHz, CDCl$_3$, δ): 0.79, 0.86 (9H, m), 1.03–1.94 (8H, m), 2.20 (1H, m), 2.40, 2.98 (1H, m), 3.67 (2H, s), 3.74 (2H, q), 3.88 (3H, s), 4.12 (2H, t), 6.27 (1H, m), 6.81–7.45 (8H, m), 8.24 (1H, s).

EXAMPLES 76 TO 79

Instead of cyclohexylzinc bromide in Example 1, various zinc bromide compounds are treated in a similar manner to Example 1 to give the compounds as listed in Table 17.

TABLE 17

[Structure: MeO, HO-phenyl-CH2-C(O)-NH-phenyl-$R^4$ (meta)]

| Ex. No. | $R^4$ |
|---|---|
| 76 | -(CH2)5-Me (n-hexyl) |
| 77 | -CH2-CH(Me)-CH2-Me |
| 78 | -CH2-CH(CH2Me)-Me |
| 79 | norbornyl-CH2- |

EXAMPLES 80 TO 96

Instead of 3-(cyclohexen-1-yl)aniline (Intermediate 2) in Example 9, various aniline derivatives are treated in a similar manner to Example 9 to give the compounds as listed in Table 18.

TABLE 18

[Structure: MeO, HO-phenyl-CH2-C(O)-NH-phenyl with $R^5$ (ortho) and $R^4$ (meta)]

| Ex. No. | $R^4$ | $R^5$ |
|---|---|---|
| 80 | 4-t-Bu-cyclohexenyl | H |
| 81 | 4-CF3-cyclohexyl | H |
| 82 | 2-Me-cyclohexyl | H |

TABLE 18-continued

[Structure: MeO, HO-phenyl-CH2-C(O)-NH-phenyl with $R^5$ (ortho) and $R^4$ (meta)]

| Ex. No. | $R^4$ | $R^5$ |
|---|---|---|
| 83 | 3-Me-cyclohexyl | H |
| 84 | 2,3-diMe-6-Me-cyclohexyl | H |
| 85 | 3,5-diMe-cyclohexyl | H |
| 86 | 1-Me-4-t-Bu-piperidin-4-yl | H |
| 87 | 1-Me-3-cyclohexyl-piperidin-3-yl | H |
| 88 | 1-Me-3-Me-piperidin-3-yl | H |
| 89 | 1-Me-4-Me-piperidin-4-yl | H |
| 90 | 1-Me-4-benzyl-piperidin-4-yl | H |
| 91 | —Ph | t-BuCOOCH2— |
| 92 | —Ph | Me |
| 93 | 1-Me-4,4-diF-cyclohexyl | H |
| 94 | 1-Me-2-Ph-morpholin-? | H |

TABLE 18-continued

![Structure with R4, R5 on aniline ring, MeO and HO on phenylacetamide]

| Ex. No. | R⁴ | R⁵ |
|---|---|---|
| 95 | 3-(1-methylpiperidin-3-yl)-fluorophenyl group (F) | H |
| 96 | 3-(1-methylpiperidin-3-yl)-trifluoromethylphenyl group (CF₃) | H |

EXAMPLE 97

Preparation of N-(2-benzylphenyl)-4-hydroxy-3-methoxyphenylacetamide

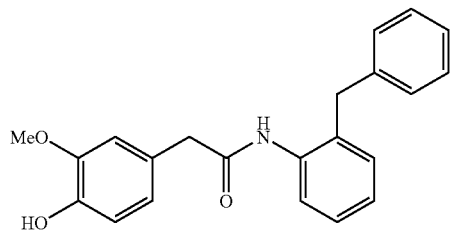

The corresponding strating compounds are treated in a similar manner to Example 9 to give the desired compounds.

EXAMPLES 98 TO 99

Instead of 3-(cyclohexen-1-yl)aniline (Intermediate 2) and 4-hydroxy-3-methoxyphenylacetic acid pentafluorophenyl ester in Example 9, 3-(4-tert-butylcyclohexan-1-yl) aniline and various pentafluorophenyl esters are used respectively and treated in a similar manner to Example 9 to give the compounds as listed in Table 19.

TABLE 19

![Structure with R2, R3 substituents and 4-tert-butylcyclohexyl group]

| Ex. No. | R² | R³ |
|---|---|---|
| 98 | H | I |
| 99 | Me | H |

EXAMPLES 100 TO 105

Instead of phenyboronic acid in Example 35, various arylboronic acid derivatives are treated in a similar manner to Example 35 to give the compounds as listed in Table 20.

TABLE 20

![Structure with R4 substituent on aniline]

| Ex. No. | R⁴ |
|---|---|
| 100 | 5-chloro-2-methylthiophen-yl |
| 101 | 2-methyl-1-(tert-butoxycarbonyl)pyrrol-yl |
| 102 | 2-methylbenzothiophen-yl |
| 103 | 3-methylquinolin-yl |
| 104 | 1,5-dimethylindol-yl |
| 105 | 5-methyl-1H-indol-yl |

EXAMPLE 106

Preparation of 4-hydroxy-3-methoxy-N-(4-phenylphenyl)phenylacetamide

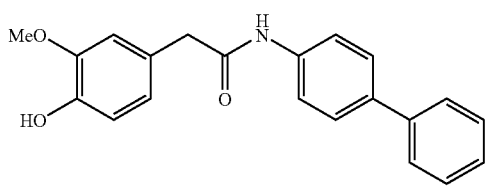

Instead of Intermediate 1 in Example 35, 4-hydroxy-N-(4-iodophenyl)-3-methoxyphenylacetamide is treated in a similar manner to Example 35 to give the desired compound.

EXAMPLE 107

Preparation of 4-hydroxy-3-methoxy-N-[2-(2-phenylethynyl)phenyl]-phenylacetamide

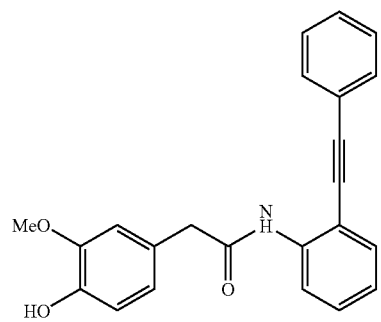

Instead of Intermediate 1 in Example 36, 4-hydroxy-N-(2-iodophenyl)-3-methoxyphenylacetamide is treated in a similar manner to Example 36 to give the desired compound.

EXAMPLES 108 TO 112

Instead of 1-trifluoromethyl-2-iodobenzene in Example 37, various iodobenzene derivatives are treated in a similar manner to Example 37 to give the compounds as listed in Table 21.

TABLE 21

| Ex. No. | $R^8$ |
|---|---|
| 108 | 3-thienyl |
| 109 | 3-furyl |
| 110 | 5-indolyl |
| 111 | 2-thiazolyl |
| 112 | benzo[1,3]dioxol-5-yl |

EXAMPLES 113 TO 116

Instead of 4-hydroxy-3-methoxy-N-[3-(2-phenylethynyl)phenyl]-phenylacetamide in Example 54, various ethynyl derivatives are treated in a similar manner to Example 54 to give the compounds as listed in Table 22.

TABLE 22

| Ex. No. | $R^8$ |
|---|---|
| 113 | 3-furyl |
| 114 | cyclohexyl |
| 115 | 5-indolyl |
| 116 | benzo[1,3]dioxol-5-yl |

EXAMPLE 117

Preparation of 4-hydroxy-3-methoxy-N-[2-(2-phenylethyl)phenyl]phenylacetamide

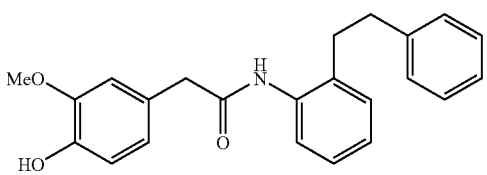

Instead of 4-hydroxy-3-methoxy-N-[3-(2-phenylethynyl)phenyl]-phenylacetamide (the compound of Example 36) in Example 54, 4-hydroxy-3-methoxy-N-[2-(2-phenylethynyl)phenyl]phenylacetamide (the compound of Example 107) is treated in a similar manner to Example 54 to give the desired compound.

EXAMPLE 118

Preparation of 4-hydroxy-3-methoxy-N-[2-[(Z)-2-phenylvinyl]phenyl]-phenylacetamide

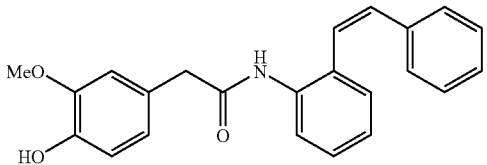

Instead of 4-hydroxy-3-methoxy-N-[3-(2-phenylethynyl)phenyl]-phenylacetamide (the compound of Example 36) in Example 56, 4-hydroxy-3-methoxy-N-[2-(2-phenylethynyl)phenyl]phenylacetamide (the compound of Example 107) is treated in a similar manner to Example 56 to give the desired compound.

EXAMPLE 119

Preparation of 4-acetoxy-3-methoxy-N-(3-phenylphenyl)phenylacetamide

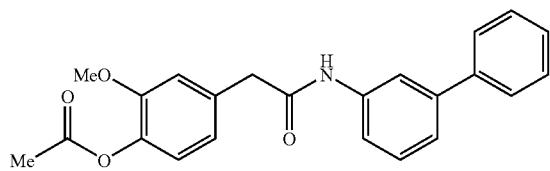

Instead of N-[3-(4-tert-butylcyclohexan-1-yl)phenyl]-4-hydroxy-3-methoxyphenylacetamide in Example 69, the compound of Example 35 is treated in a similar manner to Example 69 to give the desired compound.

EXAMPLE 120

Preparation of 4-hydroxy-3-methoxyphenyl-N-[3-(pyrrol-2-yl)phenyl]-phenylacetamide

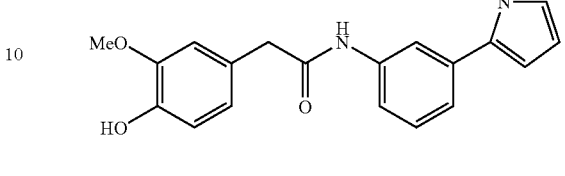

The compound of Example 101 (100 mg) is dissolved in 30% hydrochloric acid-ethanol, and the mixture is stirred at 50° C. for 10 minutes. The solvent is evaporated under reduced pressure, and the residue is purified by silica gel column chromatography (eluent: gradient from 0% to 10% chloroform/methanol) to give the desired compound (50 mg).

$^1$H-NMR (300 MHz, DMSO-$d_6$, δ): 3.51 (2H, s), 3.74 (3H, s), 6.31 (1H, m), 6.41 (1H, d), 6.69–6.72 (4H, m), 6.91 (1H, d), 7.25–7.38 (2H, m), 7.88 (1H, s), 8.81 (1H, bs), 10.15 (1H, s), 11.49 (1H, s).

EXAMPLE 121

Preparation of 4-(2-aminoethoxy)-3-methoxy-N-[3-(2-methoxycarbonylphenyl)phenyl]phenylacetamide hydrochloride

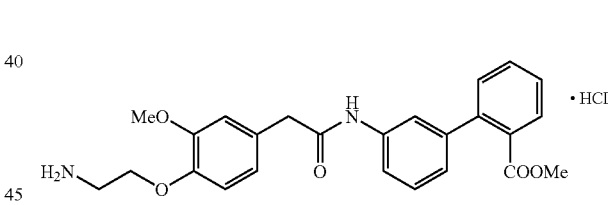

Intermediate 6 (526 mg) is dissolved in tetrahydrofuran (7 ml), and thereto are added tetrakis(triphenylphosphine)palladium (0) (115 mg), methyl 2-iodobenzoate (786 mg), cesium carbonate (978 mg) and water (1 ml), and the mixture is heated under reflux for 42 hours under argon atmosphere. The solvent is evaporated under reduced pressure, and the residue is purified by silica gel column chromatography (eluent: gradient from 0% to 100% hexane/ethyl acetate) to give 4-[2-(tert-butoxycarbonylamino)ethoxy]-3-methoxy-N-[3-(2-methoxycarbonylphenyl)phenyl]phenylacetamide (100 mg). This product is treated with 10% hydrogen chloride-methanol to give the desired compound (50 mg).

$^1$H-NMR (300 MHz, DMSO-$d_6$, δ): 3.16 (2H, t), 3.58 (3H, s), 3.61 (2H, s), 3.78 (3H, s), 4.12 (2H, t), 6.88 (1H, m), 7.01 (2H, m), 7.31–7.51 (4H, m), 7.60 (3H, m), 7.71 (1H, m), 7.73–8.40 (3H, bs), 10.34 (1H, s).

EXAMPLE 122

Preparation of 4-(2-aminoethoxy)-3-methoxy-N-[3-(2-cyclohexylphenyl)-phenyl]phenylacetamide hydrochloride

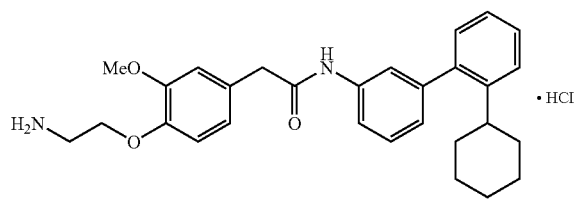

Instead of methyl 2-iodobenzoate in Example 121, 2-cyclohexyl-1-iodobenzene is treated in a similar manner to Example 121 to give the desired compound.

EXAMPLES 123 TO 168

Instead of phenylboronic acid in Example 63, various boronic acid derivatives are treated in a similar manner to Example 63 to give the compounds as listed in Table 23.

TABLE 23

| Ex. No. | $R^4$ |
|---|---|
| 123 | 2-F-C6H4 |
| 124 | 4-F-C6H4 |
| 125 | 2-Cl-C6H4 |
| 126 | 3-Cl-C6H4 |
| 127 | 3-Cl-4-F-C6H3 |
| 128 | 3,5-Cl2-C6H3 |

TABLE 23-continued

| Ex. No. | $R^4$ |
|---|---|
| 129 | 3,5-F2-C6H3 |
| 130 | 2-MeO-5-Cl-C6H3 |
| 131 | 2-Me-C6H4 |
| 132 | 2,3-Me2-C6H3 |
| 133 | 2,4,6-Me3-C6H2 |
| 134 | 4-Et-C6H4 |
| 135 | 4-Pr-i-C6H4 |
| 136 | 3-Pr-i-C6H4 |
| 137 | 2-MeO-3-Pr-i-C6H3 |
| 138 | 2-MeO-C6H4 |

TABLE 23-continued

Structure: MeO-substituted phenyl-CH2-C(=O)-NH-phenyl-R4 with H2N-CH2-CH2-O- group, ·HCl

| Ex. No. | R⁴ |
|---------|-----|
| 139 | 3,4,5-trimethoxyphenyl (OMe, OMe, OMe) |
| 140 | 4-CF₃-phenyl |
| 141 | 3-CF₃-phenyl |
| 142 | 2-CF₃-phenyl |
| 143 | 2-Ph-phenyl |
| 144 | 4-Ph-phenyl |
| 145 | 3-Ph-phenyl |
| 146 | 3-COOMe-phenyl |
| 147 | 4-COOCH₂Ph-phenyl |
| 148 | 3-COMe-phenyl |
| 149 | 2-OHC-phenyl |
| 150 | 3-OCF₃-phenyl |
| 151 | 3-NO₂-phenyl |
| 152 | 4-NO₂-phenyl |
| 153 | 2-NO₂-phenyl |
| 154 | 2-NH₂-phenyl |
| 155 | 3-NH₂-phenyl |
| 156 | 4-NH₂-phenyl |
| 157 | 3-CN-phenyl |
| 158 | 2-SMe-phenyl |
| 159 | 3-pyridyl |
| 160 | 2,4-dimethoxypyrimidin-5-yl |
| 161 | 3-thienyl |

TABLE 23-continued

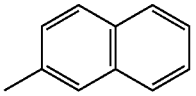

| Ex. No. | R⁴ |
|---|---|
| 162 | 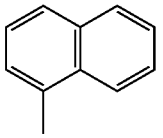 |
| 163 | 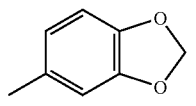 |
| 164 | 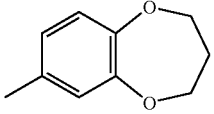 |
| 165 | 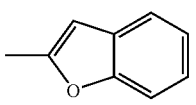 |
| 166 | 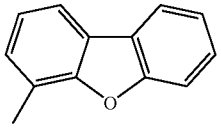 |
| 167 | 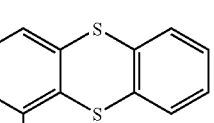 |
| 168 | 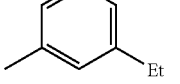 |

EXAMPLE 169

Preparation of 4-(2-aminoethoxy)-N-[3-(3-tert-butylphenyl)phenyl]-3-methoxyphenylacetamide hydrochloride

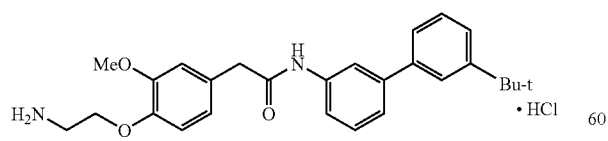

Intermediate 7 (2.4 g) and 3-(tert-butyl)aniline (1.7 g) are dissolved in ethyl acetate, and the mixture is heated under reflux for 18 hours. The solvent is evaporated under reduced pressure, and the residue is purified by silica gel column chromatography (eluent: gradient from 0% to 100% hexane/ethyl acetate) to give 4-[2-(tert-butoxycarbonylamino)ethoxy]-N-[3-(3-tert-butylphenyl)phenyl]-3-methoxyphenylacetamide (700 mg). This product is treated with 10% hydrogen chloride-methanol to give the desired compound (200 mg).

¹H-NMR (300 MHz, CD₃OD, δ): 1.33 (9H, s), 3.30 (2H, t), 3.71 (2H, s), 3.85 (3H, s), 4.17 (2H, t), 6.94 (2H, m), 7.09 (1H, s), 7.28–7.37 (5H, m), 7.62 (2H, m), 7.95 (1H, s).

EXAMPLES 170 TO 202

Instead of 3-(tert-butyl)aniline in Example 169, various aniline derivatives are treated in a similar manner to Example 169 to give the compounds as listed in Tables 24 and 25.

TABLE 24

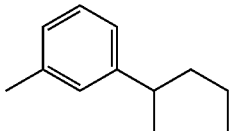

| Ex. No. | R⁵ |
|---|---|
| 170 | 6-F |
| 171 | 5-F-6-MeO |
| 172 | 6-Me |
| 173 | 4-Me |
| 174 | 2-Me |
| 175 | 2,4,6-(Me)₃ |
| 176 | 4-MeO |
| 177 | 6-MeO |
| 178 | 5-CF₃ |
| 179 | 4-CF₃O |
| 180 | 4-Ph |
| 181 | 4-Me-5-Ph |

TABLE 25

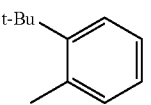

| Ex. No. | R⁴ | X¹ |
|---|---|---|
| 182 |  | H |
| 183 |  | H |
| 184 |  | H |

TABLE 25-continued

[Structure: MeO and H2N-CH2-CH2-O substituted phenyl-CH2-C(=O)-N(X¹)-phenyl-R⁴ · HCl]

| Ex. No. | R⁴ | X¹ |
|---|---|---|
| 185 | 4-methylphenyl-C(Me)(Me)-COOEt | H |
| 186 | 2-methoxyphenyl | H |
| 187 | 2-(methoxymethyl)phenyl (methoxyethylphenyl) | H |
| 188 | PhCH=CH-C(=O)-Me | H |
| 189 | 4-methyl-1,1-dimethylcyclohexyl | H |
| 190 | 4-methyl-1-tert-butylcyclohexenyl | H |
| 191 | 3,3,5-trimethyl-5-methylcyclohexyl (Me, Me, Me, Me) | H |
| 192 | 4-methyl-1-ethyl-1-propylcyclohexyl | H |
| 193 | 4-methyl-1,1-diphenylcyclohexyl | H |
| 194 | trans-4-methyl-1-tert-butylcyclohexyl | H |
| 195 | trans-4-methyl-1-tert-butylcyclohexyl | H |
| 196 | 4-methyl-1-tert-butylcyclohexyl | Me |
| 197 | N-methylpiperidin-1-yl | H |
| 198 | 4-tert-butyl-N-methylpiperidin-4-yl | H |
| 199 | 3-cyclohexyl-N-methylpiperidin-3-yl | H |
| 200 | 3-phenyl-N-methylpiperidin-3-yl | H |
| 201 | N-methyl-2-azaspiro[5.5]undecanyl | H |
| 202 | N-methylmorpholinyl | H |

EXAMPLE 203

Preparation of 4-(2-aminoethoxy)-N-[3-(3-carboxyphenyl)phenyl]-3-methoxyphenylacetamide trifluoroacetate

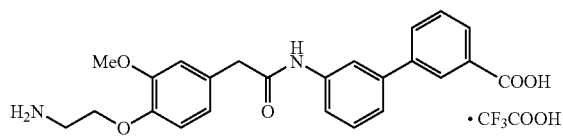

The compound of Example 146 (50 mg) is dissolved in methanol (3 ml), and thereto are added lithium hydroxide (10 mg) and water (1 ml), and the mixture is stirred at 25° C. for 5 minutes. The solvent is evaporated, and the residue is purified by CHP-20 (manufactured by Mitsubishi Kasei Corporation; high porous styrene resin: 75 to 150 μm) (eluent: gradient from 40% to 70% (0.05% aqueous trifluoroacetic acid solution)/methanol) to give the desired compound (30 mg).

$^1$H-NMR (300 MHz, DMSO-$d_6$, δ): 3.18 (2H, t), 3.61 (2H, s), 3.79 (3H, s), 4.11 (2H, t), 6.88 (1H, d), 6.70–7.04 (2H, m), 7.38–7.45 (2H, m), 7.57–7.65 (2H, m), 7.85–7.98 (3H, m), 8.15 (1H, s), 10.29 (1H, s).

EXAMPLE 204

Preparation of 4-(2-aminoethoxy)-N-[3-[4-(1-carboxy-1-methylethyl)-phenyl]phenyl]-3-methoxyphenylacetamide trifluoroacetate

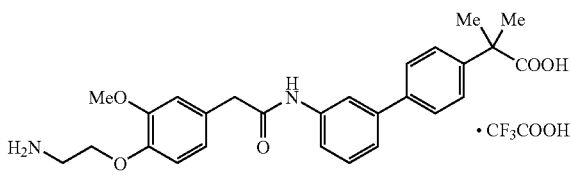

Instead of the compound of Example 146 in Example 203, the compound of Example 185 is treated in a similar manner to Example 203 to give the desired compound.

EXAMPLE 205

Preparation of N-[3-(4-tert-butylcyclohexan-1-yl) phenyl]-4-(2-hydroxyethyloxy)-3-methoxyphenylacetamide

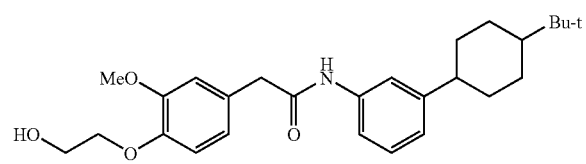

N-[3-(4-tert-Butylcyclohexan-1-yl)phenyl]-4-ethoxycarbonylmethyloxy-3-methoxyphenylacetamide (240 mg), which is an intermediate of Example 72, is dissolved in ethanol, and thereto is added sodium borohydride (35 mg), and the mixture is stirred at room temperature for 2 hours. A saturated aqueous ammonium chloride solution is added thereto, and the mixture is extracted with chloroform. The extracted is washed with water, and the solvent is evaporated under reduced pressure. The residue is purified by silica gel column chromatography (eluent: gradient from 0% to 100% hexane/ethyl acetate) to give the desired compound (110 mg).

$^1$H-NMR (300 MHz, CDCl$_3$, δ): 0.79, 0.86 (9H, m), 1.0–1.30 (3H, m), 1.33–1.48 (1H, m), 1.50–1.95 (4H, m), 2.20 (1H, m), 2.40, 2.98 (1H, m), 3.67 (2H, s), 3.87 (3H, s), 3.96 (2H, t), 4.14 (2H, t), 6.83–7.42 (8H, m).

EXAMPLE 206

Preparation of 4-(2-aminoethoxy)-N-[3-(4-tert-butylcyclohexan-1-yl)-phenyl]-3-(methanesulfonylamino)phenylacetamide hydrochloride

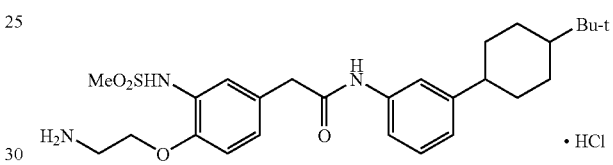

N-[3-(4-tert-Butylcyclohexan-1-yl)phenyl]-4-hydroxy-3-nitrophenylacetamide (550 mg), which is prepared in a similar manner to Example 9, is treated in a similar manner to Reference Example 4 to give N-[3-(4-tert-butylcyclohexan-1-yl)phenyl]-3-nitro-4-(2-phthalimidoethoxy)phenylacetamide (500 mg). This product is dissolved in ethanol (10 ml), and thereto are added reduced iron (240 mg), ammonium chloride (90 mg) and water (5 ml), and the mixture is heated under reflux for one hour. The insoluble materials are removed by filtration, and the solvent is evaporated under reduced pressure. The residue is purified by silica gel column chromatography (eluent: gradient from 0% to 100% hexane/ethyl acetate) to give 3-amino-N-[3-(4-tert-butylcyclohexan-1-yl)phenyl]-4-(2-phthalimidoethoxy) phenylacetamide (140 mg). This product is dissolved in methylene chloride (5 ml), and thereto is added triethylamine (33 mg). To the mixture is added dropwise methanesulfonyl chloride (33 mg), and the mixture is stirred for 2 hours. The mixture is washed with water, and the solvent is evaporated under reduced pressure. The residue is purified by silica gel column chromatography (eluent: gradient from 0% to 100% hexane/ethyl acetate) to give N-[3-(4-tert-butylcyclohexan-1-yl)phenyl]-3-methanesulfonylamino-4-(2-phthalimidoethoxy)phenylacetamide (70 mg). This product is treated with hydrazine monohydrate in a similar manner to Example 58 to give the desired compound (30 mg).

$^1$H-NMR (300 MHz, DMSO-$d_6$, δ): 0.76, 0.85 (9H, m), 1.0–1.90 (8H, m), 2.10–2.20 (1H, m), 2.50, 2.94 (1H, m), 2.95 (3H, s), 3.30 (2H, m), 3.55 (2H, s) 4.15 (2H, t), 6.85–7.60 (7H, m), 8.01 (3H, brs), 8.88 (1H, s), 10.02 (1H, m).

EXAMPLE 207

Preparation of 4-(2-aminoethoxy)-N-[3-[(E)-2-(3-methylphenyl)vinyl]-phenyl]-3-methoxyphenylacetamide hydrochloride

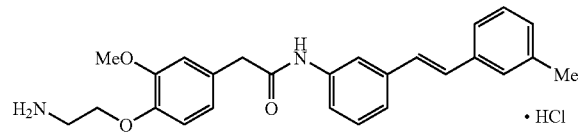

Intermediate 4 (1 g) is dissolved in dimethylformamide (10 ml), and thereto are added 3-methylvinylbenzene (826 mg), palladium (II) acetate (105 mg), tris(2-methylphenyl) phosphine (143 mg), tetra-n-butyl ammonium chloride (130 mg), and the mixture is heated with stirring at 97° C. for 18 hours under argon atmosphere. To the reaction solution is added ethyl acetate, and the mixture is washed with water and 2 M hydrochloric acid. The organic layer is dried over sodium sulfate, and the solvent is evaporated under reduced pressure. The residue is purified by silica gel column chromatography (eluent: gradient from 0% to 100% hexane/ethyl acetate) to give 4-[2-(tert-butoxycarbonylamino)-ethoxy]-3-methoxy-N-[3-[(E)-2-(3-methylphenyl)vinyl]phenyl]phenylacetamide (370 mg). This product is treated with 10% hydrogen chloride-methanol to give the desired compound (120 mg).

$^1$H-NMR (300 MHz, DMSO-d$_6$, δ): 2.33 (3H, s), 3.17 (2H, t), 3.62 (2H, s), 3.80 (3H, s), 4.14 (2H, t), 6.87–7.49 (12H, m), 7.87 (1H, s), 8.09 (3H, bs), 10.31 (1H, s).

EXAMPLES 208 TO 216

Instead of 3-methylvinylbenzene in Example 207, various vinyl derivatives are treated in a similar manner to Example 207 to give the compounds as listed in Table 26.

TABLE 26

| Ex. No. | R$^8$ |
|---|---|
| 208 | phenyl |
| 209 | 4-F-phenyl |
| 210 | 2-Cl-phenyl |
| 211 | 4-Cl-phenyl |
| 212 | 3-CF$_3$-phenyl |
| 213 | 4-SO$_2$NH$_2$-phenyl |
| 214 | 4-OH-phenyl |
| 215 | 4-pyridyl |
| 216 | 2-naphthyl |

EXAMPLE 217

Preparation of 4-(2-aminoethoxy)-3-methoxy-N-[3-[2-(3-methylphenyl)-ethyl]phenyl]phenylacetamide hydrochloride 4-[2-(tert-Butoxycarbonylamino)ethoxy]-3-methoxy-N-[3-[(E)-2-(3-methylphenyl)vinyl]phenyl]phenylacetamide (100 mg) is dissolved in methanol (10 ml) and acetic acid (1 ml), and thereto is added 10% palladium on carbon (10 mg), and the mixture is subjected to catalytic hydrogenation at 50° C. The catalyst is removed by filtration, and the solvent is evaporated to give 4-[2-(tert-butoxycarbonylamino) ethoxy]-3-methoxy-N-[3-[2-(3-methylphenyl)ethyl]phenyl] phenylacetamide (80 mg). This product is treated with 10% hydrogen chloride-methanol to give the desired compound (50 mg).

¹H-NMR (300 MHz, DMSO-d₆, δ): 2.26 (3H, s), 2.80 (4H, s), 3.17 (2H, t), 3.57 (2H, s), 3.79 (3H, s), 4.13 (2H, t), 6.85–7.44 (10H, m), 7.51 (1H, s), 8.02 (3H, bs), 10.14 (1H, s).

EXAMPLES 218 TO 224

Instead of 4-[2-(tert-butoxycarbonylamino)ethoxy]-3-methoxy-N-[3-[(E)-2-(3-methylphenyl)vinyl]phenyl]phenylacetamide in Example 217, the corresponding derivatives are treated in a similar manner to Example 217 to give the compounds as listed in Table 27.

TABLE 27

| Ex. No. | R⁸ |
|---|---|
| 218 | 4-F-phenyl |
| 219 | 2-F-phenyl |
| 220 | 3-CF₃-phenyl |
| 221 | 4-SO₂NH₂-phenyl |
| 222 | 4-OH-phenyl |
| 223 | 4-pyridyl |
| 224 | 2-naphthyl |

EXAMPLES 225 TO 235

Instead of 3-(tert-butyl)aniline in Example 169, Intermediate 8 of Reference Example 8, and 7-amino-1-oxo-1,2,3,4-tetrahydronaphthalene derivatives obtained in a similar manner to Reference Example 8 are used and treated in a similar manner to Example 169 to give the compounds as listed in Table 28.

TABLE 28

| Ex. No. | R⁹¹ |
|---|---|
| 225 | phenyl |
| 226 | 2-Me-phenyl |
| 227 | 3-Me-phenyl |
| 228 | 4-Me-phenyl |
| 229 | 3-OMe-phenyl |
| 230 | 4-OMe-phenyl |
| 231 | 2-pyridyl |
| 232 | 3-pyridyl |
| 233 | 4-pyridyl |
| 234 | 2-imidazolyl |
| 235 | 2-naphthyl |

EXAMPLES 236 TO 247

Instead of 3-(cyclohexen-1-yl)aniline in Example 9, Intermediate 9 and aminoindole derivatives obtained in a similar manner to Reference Example 9 are used and treated in a similar manner to Example 9 to give the compounds as listed in Tables 29 to 32.

TABLE 29

| Ex. No. | R⁹¹ |
|---|---|
| 236 | –CH₂–CH₂–Ph |
| 237 | –(CH₂)₇–CH₃ |

TABLE 30

| Ex. No. | R⁹¹ |
|---|---|
| 238 | –CH₂–Ph |
| 239 | –CH₂–CH₂–Ph |
| 240 | –CH₂–cyclohexyl (ethyl linker) |
| 241 | –CH₂–CH(CH₃)–CH₂–CH₃ (2-methylbutyl) |
| 242 | –(CH₂)₄–CH=CH₂ |
| 243 | –(CH₂)₇–CH₃ |

TABLE 31

| Ex. No. | R⁹¹ |
|---|---|
| 244 | –CH₂–CH₂–Ph |

TABLE 31-continued

| Ex. No. | R⁹¹ |
|---|---|
| 245 | –(CH₂)₇–CH₃ |

TABLE 32

| Ex. No. | R⁹¹ |
|---|---|
| 246 | –CH₂–CH₂–Ph |
| 247 | –(CH₂)₇–CH₃ |

EXAMPLE 248

Preparation of 4-hydroxy-3-methoxy-N-[1-oxo-2-phenylmethylidene-1,2,3,4-tetrahydronaphthalen-7-yl]phenylacetamide Instead of 3-(cyclohexen-1-yl)aniline (Intermediate 2) in Example 9, 7-amino-1-tetralone is treated in a similar manner to Example 9. The resulting 4-hydroxy-3-methoxy-N-[1-oxo-1,2,3,4-tetrahydronaphthalen-7-yl]phenylacetamide (1 g) is dissolved in 30% hydrogen chloride-ethanol (5 ml), and thereto is added benzaldehyde (433 mg). The mixture is stirred at 25° C. for 18 hours. The precipitated crystals are collected by filtration, and washed with diethyl ether to give the desired compound (700 mg).

¹H-NMR (300 MHz, CDCl₃, δ): 2.89 (2H, t), 3.10 (2H, t), 3.69 (2H, s), 3.89 (3H, s), 5.70 (1H, s), 6.80–6.85 (2H, m), 6.95 (2H, d), 7.22 (1H, d), 7.30–7.43 (5H, m), 7.66 (1H, d), 7.84 (1H, s), 8.09 (1H, dd).

EXAMPLE 249

Preparation of 4-hydroxy-3-methoxy-N-[1-oxo-2-phenylmethyl-1,2,3,4-tetrahydronaphthalen-7-yl]phenylacetamide

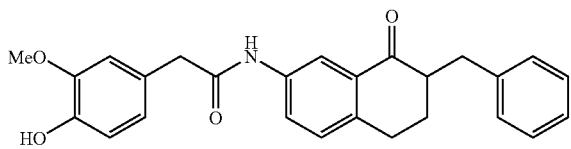

The compound of Example 248 (500 mg) is dissolved in ethyl acetate (20 ml), and thereto is added 10% palladium on carbon (50 mg), and the mixture is subjected to catalytic hydrogenation at 25° C. The catalyst is removed by filtration, and the solvent is evaporated under reduced pressure. The residue is purified by silica gel column chromatography (eluent: gradient from 0% to 100% hexane/ethyl acetate) to give the desired compound (350 mg).

$^1$H-NMR (300 MHz, CDCl$_3$, δ): 1.67–1.81 (1H, m), 2.05–2.13 (1H, m), 2.58–2.94 (4H, m), 3.43 (1H, dd), 3.67 (2H, s), 3.91 (3H, s), 5.67 (1H, s), 6.80–7.00 (3H, m), 7.25–7.35 (7H, m), 7.60 (1H, d), 8.01 (1H, dd).

EXAMPLE 250

Preparation of 4-hydroxy-3-methoxy-N-[1-oxo-2-(2-methylpropylidene-1,2,3,4-tetrahydronaphthalen-7-yl]phenylacetamide

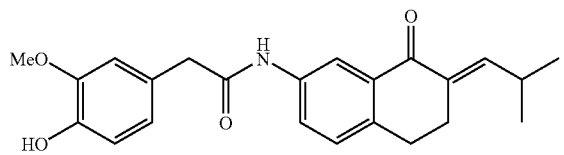

Instead of benzaldehyde in Example 248, isobutyl aldehyde is treated in a similar manner to Example 248 to give the desired compound.

EXAMPLE 251

Preparation of 4-hydroxy-3-methoxy-N-[1-oxo-2-(2-methylpropyl)-1,2,3,4-tetrahydronaphthalen-7-yl]phenylacetamide

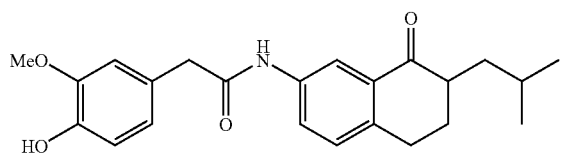

The compound of Example 250 is treated in a similar manner to Example 249 to give the desired compound.

EXAMPLES 252 TO 255

Instead of 3-cycloheptylaniline in Example 58, 6-aminoindole derivatives are treated in a similar manner to Example 58 to give the compounds as listed in Table 33.

TABLE 33

![Structure with R$^{91}$ and HCl]

| Ex. No. | R$^{91}$ |
|---------|----------|
| 252 | benzyl (CH$_2$-phenyl) |
| 253 | (naphthalen-2-yl)methyl |
| 254 | phenylsulfonyl (O$_2$S-phenyl) |
| 255 | 3-phenylpropyl |

EXAMPLES 256 TO 258

Instead of phenylboronic acid in Example 35, the corresponding derivatives are treated in a similar manner to Example 35 to give the compounds as listed in Table 34.

TABLE 34

![Structure with R$^4$]

| Ex. No. | R$^4$ |
|---------|-------|
| 256 | 2,3-dihydro-1,4-benzodioxin-6-yl |
| 257 | furan-3-yl |
| 258 | 3,5-dimethylisoxazol-4-yl |

EXAMPLES 259 TO 260

Instead of 3-(cyclohexen-1-yl)aniline in Example 9, the corresponding derivatives are treated in a similar manner to Example 9 to give the compounds as listed in Table 35.

TABLE 35

MeO, HO-phenyl-CH2-C(=O)-NH-phenyl-R4

| Ex. No. | R4 |
|---|---|
| 259 | 1-methyl-4-phenylpiperidin-4-yl |
| 260 | (1-methylpiperidin-3-yl)methyl-Ph |

The results of the analysis by HPLC of the compounds of the above Examples such as retention time (Rt) and the analysis conditions are shown in Table 36.

TABLE 36

| Ex. No. | Rt | Conditions* |
|---|---|---|
| 1 | 3.75 | a |
| 2 | 2.86 | a |
| 3 | 5.99 | a |
| 4 | 3.21 | a |
| 5 | 4.66 | a |
| 6 | 3.20 | a |
| 7 | 3.85 | a |
| 8 | 4.23 | a |
| 9 | 3.42 | a |
| 10 | 2.29 | a |
| 11 | 4.76 | a |
| 12 | 5.16 | a |
| 13** | 4.39, 4.64 | a |
| 14 | 2.15 | a |
| 15 | 3.27 | a |
| 16 | 1.50 | a |
| 17 | 2.47 | a |
| 18 | 2.01 | a |
| 19 | 2.21 | a |
| 20** | 7.85, 9.13 | a |
| 21 | 2.86 | a |
| 22 | 3.25 | a |
| 23 | 2.75 | a |
| 24 | 3.27 | a |
| 25 | 1.43 | a |
| 26 | 3.25 | a |
| 27 | 3.39 | a |
| 28 | 2.84 | a |
| 29 | 5.34 | a |
| 30 | 6.95 | a |
| 31 | 7.29 | c |
| 32 | 4.36 | a |
| 33 | 3.09 | a |
| 34 | 3.08 | a |
| 35 | 2.76 | a |
| 36 | 3.36 | a |
| 37 | 3.77 | a |
| 38 | 4.03 | a |
| 39 | 4.67 | a |
| 40 | 3.02 | a |
| 41 | 3.38 | a |
| 42 | 5.33 | a |
| 43 | 5.00 | a |
| 44 | 5.43 | a |
| 45 | 3.54 | a |
| 46 | 3.33 | a |
| 47 | 3.46 | a |
| 48 | 3.82 | a |
| 49 | 4.46 | a |
| 50 | 4.62 | a |
| 51 | 4.53 | a |
| 52 | 4.82 | a |
| 53 | 6.89 | a |
| 54 | 3.20 | a |
| 55 | 3.16 | a |
| 56 | 3.15 | a |
| 57 | 2.22 | a |
| 58 | 5.52 | b |
| 59 | 4.09 | b |
| 60 | 3.75 | b |
| 61 | 4.18 | b |
| 62** | 12.58, 16.39 | b |
| 63 | 2.68 | b |
| 64 | 7.50 | b |
| 65 | 2.67 | b |
| 66 | 3.11 | b |
| 67 | 3.96 | b |
| 68 | 3.54 | b |
| 69** | 11.49, 13.45 | a |
| 70** | 9.25, 10.46 | c |
| 71** | 10.23, 11.58 | c |
| 72** | 6.31, 7.28 | a |
| 73** | 12.22, 16.14 | b |
| 74** | 2.78, 3.07 | a |
| 75** | 5.86, 6.73 | a |
| 76 | 4.57 | a |
| 77 | 5.19 | a |
| 78 | 4.14 | a |
| 79 | 3.87 | a |
| 80 | 7.41 | a |
| 81** | 3.44, 3.68 | a |
| 82** | 3.99, 4.26 | a |
| 83** | 4.26, 4.47 | a |
| 84 | 5.07 | a |
| 85** | 5.30, 5.66 | a |
| 86 | 2.25 | d |
| 87 | 2.40 | d |
| 88 | 3.10 | f |
| 89 | 3.05 | f |
| 90 | 2.41 | d |
| 91 | 9.76 | d |
| 92 | 4.93 | d |
| 93 | 2.78 | a |
| 94 | 4.97 | d |
| 95 | 2.67 | d |
| 96 | 3.60 | d |
| 97 | 2.68 | a |
| 98** | 11.7, 14.0 | a |
| 99** | 9.72, 11.4 | a |
| 100 | 8.2 | d |
| 101 | 7.5 | d |
| 102 | 9.63 | d |
| 103 | 2.08 | d |
| 104 | 5.90 | d |
| 105 | 4.20 | d |
| 106 | 2.76 | a |
| 107 | 7.8 | d |
| 108 | 3.06 | a |
| 109 | 2.28 | a |
| 110 | 2.75 | a |
| 111 | 2.42 | a |
| 112 | 3.11 | a |
| 113 | 2.45 | a |
| 114 | 5.80 | a |
| 115 | 2.71 | a |
| 116 | 2.93 | a |
| 117 | 5.14 | d |
| 118 | 5.8 | d |
| 119 | 8.22 | d |

TABLE 36-continued

| Ex. No. | Rt | Conditions* |
|---|---|---|
| 120 | 2.15 | d |
| 121 | 2.24 | d |
| 122 | 5.57 | d |
| 123 | 2.33 | d |
| 124 | 2.44 | d |
| 125 | 2.58 | d |
| 126 | 2.80 | d |
| 127 | 2.97 | d |
| 128 | 3.81 | d |
| 129 | 2.65 | d |
| 130 | 2.89 | d |
| 131 | 2.55 | d |
| 132 | 3.03 | d |
| 133 | 3.57 | d |
| 134 | 3.20 | d |
| 135 | 3.86 | d |
| 136 | 4.04 | d |
| 137 | 3.62 | d |
| 138 | 2.39 | d |
| 139 | 2.05 | d |
| 140 | 3.24 | d |
| 141 | 2.90 | d |
| 142 | 2.59 | d |
| 143 | 3.20 | d |
| 144 | 4.14 | d |
| 145 | 4.01 | d |
| 146 | 2.41 | d |
| 147 | 4.70 | d |
| 148 | 2.05 | d |
| 149 | 2.06 | d |
| 150 | 3.13 | d |
| 151 | 2.47 | d |
| 152 | 2.49 | d |
| 153 | 2.29 | d |
| 154 | 4.28 | d |
| 155 | 2.78 | d |
| 156 | 2.64 | d |
| 157 | 2.21 | d |
| 158 | 2.48 | d |
| 159 | 2.74 | i |
| 160 | 4.69 | f |
| 161 | 3.88 | g |
| 162 | 3.2 | d |
| 163 | 3.11 | d |
| 164 | 2.27 | d |
| 165 | 2.33 | d |
| 166 | 2.84 | d |
| 167 | 5.95 | d |
| 168 | 5.20 | d |
| 169 | 4.06 | d |
| 170 | 2.26 | d |
| 171 | 2.63 | d |
| 172 | 2.21 | d |
| 173 | 2.44 | d |
| 174 | 2.16 | d |
| 175 | 2.41 | d |
| 176 | 2.14 | d |
| 177 | 2.34 | d |
| 178 | 3.25 | d |
| 179 | 3.03 | d |
| 180 | 3.30 | d |
| 181 | 4.34 | d |
| 182 | 2.94 | d |
| 183 | 6.53 | d |
| 184 | 3.67 | d |
| 185 | 3.17 | d |
| 186 | 2.28 | d |
| 187 | 2.56 | d |
| 188 | 2.35 | d |
| 189 | 4.35 | d |
| 190 | 6.85 | d |
| 191 | 6.59 | d |
| 192 | 3.82 | a |
| 193 | 6.96 | d |
| 194 | 6.60 | d |
| 195 | 8.13 | d |
| 196** | 6.34, 8.31 | d |
| 197 | 2.64 | h |
| 198 | 3.40 | f |
| 199 | 6.19 | f |
| 200 | 4.18 | f |
| 201 | 6.36 | f |
| 202 | 2.39 | f |
| 203 | 6.94 | f |
| 204 | 2.01 | d |
| 205** | 6.19, 7.13 | a |
| 206 | 6.33 | d |
| 207 | 3.43 | d |
| 208 | 2.91 | d |
| 209 | 3.11 | d |
| 210 | 3.51 | d |
| 211 | 3.77 | d |
| 212 | 3.98 | d |
| 213 | 6.09 | f |
| 214 | 2.96 | e |
| 215 | 5.61 | h |
| 216 | 4.32 | d |
| 217 | 3.37 | d |
| 218 | 2.73 | d |
| 219 | 2.97 | d |
| 220 | 3.74 | d |
| 221 | 5.74 | f |
| 222 | 2.96 | d |
| 223 | 4.05 | h |
| 224 | 4.00 | d |
| 225 | 2.79 | d |
| 226 | 3.19 | d |
| 227 | 3.36 | d |
| 228 | 3.40 | d |
| 229 | 2.70 | d |
| 230 | 2.65 | d |
| 231 | 4.38 | h |
| 232 | 5.02 | h |
| 233 | 5.02 | h |
| 234 | 3.33 | h |
| 235 | 4.11 | d |
| 236 | 2.96 | a |
| 237 | 3.69 | a |
| 238 | 2.73 | a |
| 239 | 2.96 | a |
| 240 | 3.82 | a |
| 241 | 3.57 | a |
| 242 | 2.85 | a |
| 243 | 4.60 | a |
| 244 | 3.18 | a |
| 245 | 4.48 | a |
| 246 | 3.31 | a |
| 247 | 4.77 | a |
| 248 | 3.17 | a |
| 249 | 3.23 | a |
| 250 | 3.04 | a |
| 251 | 3.39 | a |
| 252 | 2.30 | d |
| 253 | 2.98 | d |
| 254 | 2.21 | d |
| 255 | 2.96 | d |
| 256 | 4.66 | d |
| 257 | 3.84 | d |
| 258 | 3.26 | d |
| 259 | 2.28 | d |
| 260 | 2.41 | d |

*Conditions for analysis:
a: 65% acetonitrile/0.05% aqueous trifluoroacetic acid solution
b: 45% acetonitrile/0.05% aqueous trifluoroacetic acid solution
c: 75% acetonitrile/0.05% aqueous trifluoroacetic acid solution
d: 50% acetonitrile/0.05% aqueous trifluoroacetic acid solution
e: 40% acetonitrile/0.05% aqueous trifluoroacetic acid solution
f: 30% acetonitrile/0.05% aqueous trifluoroacetic acid solution
g: 25% acetonitrile/0.05% aqueous trifluoroacetic acid solution
h: 20% acetonitrile/0.05% aqueous trifluoroacetic acid solution
i: 10% acetonitrile/0.05% aqueous trifluoroacetic acid solution
**Under the conditions of these Examples, diastereomers are separated.

Preparation 1: Preparation of Tablets

| 4-(2-Aminoethoxy)-3-methoxy-N-[3-(2-phenylethynyl)phenyl]-phenylacetamide | 25 g |
|---|---|
| Lactose | 70 g |
| Corn strach | 20 g |
| Crystalline cellulose | 25 g |
| Hydroxypropyl cellulose | 3 g |

The above components are mixed and kneaded in a conventional manner, and the mixture is granulated and dried. To the mixture are added light anhydrous silicic acid (0.7 g) and magnesium stearate (1.3 g), and the mixture is further tabletted to give 1,000 tablets (each 145 mg).

Preparation 2: Preparation of Capsules

| 4-(2-Aminoethoxy)-3-methoxy-N-[3-(2-phenylethyl)phenyl]-phenylacetamide | 50 g |
|---|---|
| Lactose | 117 g |
| Corn strach | 25 g |
| Hydroxypropyl cellulose | 3.5 g |
| Purified water | 100 g |

The above components are mixed and kneaded in a conventional manner, and the mixture is granulated and dried. To the mixture are added light anhydrous silicic acid (1.8 g) and magnesium stearate (2.7 g), and each 200 mg of the resulting granule is packed into a capsule to give 1,000 capsules.

Preparation 3: Preparation of Powder

| 4-(2-Aminoethoxy)-N-(3-cyclohexylphenyl)-3-methoxyphenyl-acetamide | 200 g |
|---|---|
| Lactose | 770 g |

The above components and light anhydrous silicic acid (5 g) are mixed in a conventional manner to give a powder preparation.

Preparation 4: Preparation of Ointment Using an Oleaginous Base

| 4-(2-Aminoethoxy)-3-methoxy-N-(3-phenylphenyl)phenyl-acetamide | 0.1 g |
|---|---|
| Plastibase | 99.9 g |

The above components are mixed in a conventional manner to give an ointment.

Preparation 5: Preparation of Ointment Using an Aqueous Base

| 4-(2-Aminoethoxy)-N-[3-(4-tert-butylcyclohexan-1-yl)-phenyl]-3-methoxyphenylacetamide | 1 g |
|---|---|
| Polyethylene glycol 4000 | 44 g |
| Polyethylene glycol 400 | 55 g |

The above components are kneaded in a conventional manner with heating, if necessary, to give an ointment.

Preparation 6: Preparation of Patch

| 4-(2-Aminoethoxy)-3-methoxy-N-(3-phenylphenyl)-phenylacetamide | 10 g |
|---|---|
| Eudragit E100 | 20.5 g |
| Tributyl acetylcitrate | 10.3 g |
| Succinic acid | 0.7 g |
| Purified water | 58.5 g |

The above components are warmed, if necessary, and uniformly kneaded to give adhesive base containing a medicament for patches. The resulting base is applied and flatted onto a suitable filmy support so as to give patches containing 12.5 mg of said base per 1 cm² of the support, then, the base layer is dried and coated with a protective film, and cut into a suitable shape of a suitable size corresponding to the dose (area: 2 cm²) to give patches.

INDUSTRIAL APPLICABILITY

The compounds of the present invention exhibit a potent analgesic activity with weak pungency, and they can be effective even in oral administration. Therefore, the present compounds are useful as an agent for treatment of neuropathic pain to which conventional analgesic agents are ineffective, or pain caused by rheumatic arthritis, and as a preventive and/or a remedy for treatment of essential pruritus, allergy or nonallergic rhinitis, frequent urination and urinary incontinence with overactive bladder, stroke, irritable bowel syndrome, respiratory disorders such as asthma and chronic obstructive pulmonary disease, dermatitis, mucositis, gastric and duodenal ulcer, inflammatory bowel diseases and obesity.

The invention claimed is:

1. An N-arylphenylacetamide derivative of the following formula (I):

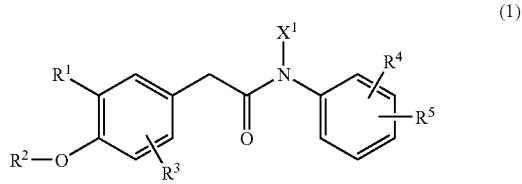

(wherein $R^1$ is a $C_{1-6}$ alkoxy group, a hydroxy group, a halogen atom, a nitro group, an amino group, a $C_{1-6}$ alkylamino group, a di-($C_{1-6}$ alkyl)-amino group, a $C_{1-6}$ alkylsulfonylamino group, or an arylsulfonylamino group, $R^2$ is a hydrogen atom, a $C_{1-6}$ alkylcarbonyl group, an arylcarbonyl group, —$(CH_2)_m$—$N(R^6)(R^7)$, —$(CH_2)_m$OH or —$(CH_2)_q$COOH (in which m is an integer of 2 to 4, q is an integer of 1 to 4, $R^6$ is a hydrogen atom, a $C_{1-3}$ alkyl group, a hydroxy-$C_{2-3}$ alkyl group, an amino-$C_{2-3}$ alkyl group, a formyl group, a $C_{1-3}$ alkylcarbonyl group, a $C_{1-4}$ alkoxycarbonyl group, an arylcarbonyl group, or an aryl-$C_{1-3}$ alkyloxycarbonyl group, $R^7$ is a hydrogen atom, a $C_{1-3}$ alkyl group, a hydroxy-$C_{2-3}$ alkyl group, or an amino-$C_{2-3}$ alkyl group), $R^3$ is a hydrogen atom, a halogen atom, a $C_{1-6}$ alkyl group, a $C_{1-4}$ alkoxy group, an aryl group, or a formyl group, $R^4$, which is located at the meta-position with respect to the group —$N(X^1)$—, is a $C_{6-10}$ alkyl group, a group of the following formula (A) or a group of the following formula (C), and the group of the formula (A) is a group of the formula:

—Y—R$^8$ (A)

[in which Y is a single bond, a $C_{1-3}$ alkylene group, a $C_{2-3}$ alkenylene group, a $C_{2-3}$ alkynylene group, —CO(CH$_2$)$_p$—, a $C_{2-3}$ alkenylenecarbonyl group, —O—, —O—(CH$_2$)$_2$—, —O—(CH$_2$)$_3$—, or —CONH(CH$_2$)$_p$—, and p is an integer of 0 to 3, R$^8$ is a monocyclic group or a polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a $C_{2-6}$ alkenyl, a $C_{2-6}$ alkynyl, a trifluoromethyl, a trifluoroethyl, an aryl, an aryl-$C_{1-6}$ alkyl, a $C_{1-6}$ alkoxy, a trifluoromethoxy, a $C_{3-7}$ cycloalkyloxy, an aryloxy, an aryl-$C_{1-3}$ alkyloxy, a $C_{1-6}$ alkylcarbonyl, a $C_{3-7}$ cycloalkylcarbonyl, a formyl, a nitro, an amino, a di-($C_{1-6}$ alkyl)amino, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl, an aryl-$C_{1-3}$ alkyloxycarbonyl, a carboxy and a sulfamoyl; a $C_{5-7}$ cycloalkenyl group which may optionally be substituted by 1 to 4 atoms or groups selected from a $C_{1-6}$ alkyl, a $C_{3-7}$ cycloalkyl, a halogen, a trifluoromethyl, a $C_{1-4}$ alkoxycarbonyl, an aryl, an aryl-$C_{1-6}$ alkyl, a $C_{1-3}$ alkoxy and a hydroxy; or a group of the formula (B):

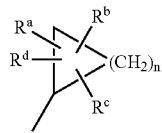

(B)

(R$^a$, R$^b$, R$^c$ and R$^d$ are the same or different and each is a hydrogen atom, a $C_{1-6}$ alkyl group, a $C_{3-7}$ cycloalkyl group, a halogen atom, a trifluoromethyl group, a $C_{1-4}$ alkoxycarbonyl group, an aryl group, an aryl-$C_{1-6}$ alkyl group, a $C_{1-3}$ alkoxy group or a hydroxy group, or when R$^a$ and R$^b$ attach to the same carbon atom, then these groups may combine to form an oxo group or a thioxo group, or when R$^c$ and R$^d$ attach to the same carbon atom, then these groups may combine together with said carbon atom to form a spiro ring, or 2 or 3 groups selected from R$^a$, R$^b$ and R$^c$ may combine to form a $C_{6-15}$ polycycloalkyl group, and n is an integer of 1 to 6)], and the group of the formula (C) is a group of the formula:

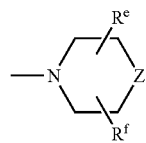

(C)

(R$^e$ and R$^f$ are the same or different and each is a hydrogen atom, a $C_{1-6}$ alkyl group, a $C_{3-7}$ cycloalkyl group, a halogen atom, a trifluoromethyl group, a $C_{1-4}$ alkoxycarbonyl group, an aryl group, an aryl-$C_{1-6}$ alkyl group, a $C_{1-3}$ alkoxy group or a hydroxy group, or when R$^e$ and R$^f$ attach to the same carbon atom, then these groups may combine together with said carbon atom to form a spiro ring, and Z is a carbon atom, an oxygen atom or a sulfur atom), R$^5$ is a hydrogen atom, a halogen atom, a $C_{1-6}$ alkyl group, a trifluoromethyl group, a $C_{1-3}$ alkoxy group, a trifluoromethoxy group, a cyano group, a nitro group, an amino group, a hydroxy group, a carboxyl group, a $C_{1-6}$ alkylcarbonyloxymethyl group, or an aryl group, or R$^4$ and R$^5$ may combine together with the benzene ring to which they bond, and form a tetralone ring or an indole ring, which is substituted by one group selected from a $C_{1-8}$ alkyl, a $C_{1-8}$ alkenyl, an aryl-$C_{1-3}$ alkyl, a $C_{3-7}$ cycloalkyl-$C_{1-3}$ alkyl, an arylsulfonyl, a $C_{1-8}$ alkylidene, a $C_{1-8}$ alkenylidene, an aryl-$C_{1-3}$ alkylidene and a $C_{3-7}$ cycloalkyl-$C_{1-3}$ alkylidene, X$^1$ is a hydrogen atom, or a pharmaceutically acceptable salt thereof, or a hydrate or solvate thereof.

2. The N-arylphenylacetamide derivative according to claim 1 of the following formula (I'):

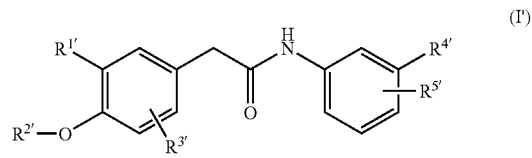

(I')

wherein R$^{1'}$ is a $C_{1-4}$ alkoxy group, a hydroxy group, a halogen atom, a nitro group, an amino group, a $C_{1-6}$ alkylsulfonylamino group or an arylsulfonylamino group, R$^{2'}$ is a hydrogen atom, a $C_{1-6}$ alkylcarbonyl group, an arylcarbonyl group or —(CH$_2$)$_2$—N(R$^{6'}$)(R$^{7'}$), in which R$^{6'}$ is a hydrogen atom, a $C_{1-3}$ alkyl group, a hydroxy-$C_{2-3}$ alkyl group, an amino-$C_{2-3}$ alkyl group, a formyl group, or an aryl-$C_{1-3}$ alkyloxycarbonyl group, and R$^{7'}$ is a hydrogen atom, a $C_{1-3}$ alkyl group, a hydroxy-$C_{2-3}$ alkyl group, or an amino-$C_{2-3}$ alkyl group, R$^{3'}$ is a hydrogen atom, a halogen atom, a $C_{1-4}$ alkyl group or an aryl group, R$^{4'}$ is a $C_{6-10}$ alkyl group, a group of the following formula (A'), or a group of the following formula (C'), in which the group of the formula (A') is a group of the formula:

—Y'—R$^{8'}$ (A')

[in which Y' is a single bond, —CH$_2$—, —(CH$_2$)$_2$—, —(CH$_2$)$_3$—, —CH=CH—, —C≡C—, —CO—, —COCH$_2$—, —CO(CH$_2$)$_2$—, —COCH=CH—, —O— or —O(CH$_2$)$_2$—, and R$^{8'}$ is a monocyclic or polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, a trifluoroethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl and a carboxy; a $C_{5-7}$ cycloalkenyl group which may optionally be substituted by 1 to 4 atoms or groups selected from a $C_{1-6}$ alkyl, a $C_{3-7}$ cycloalkyl, a fluorine, a trifluoromethyl, an aryl, a $C_{1-3}$ alkoxy and a hydroxy; or a group of the formula (B'):

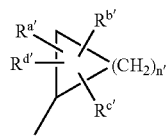

(B')

($R^{a'}$, $R^{b'}$, $R^{c'}$ and $R^{d'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group or a hydroxy group, or when $R^{a'}$ and $R^{b'}$ attach to the same carbon atom, then these groups may combine to form an oxo group, or when $R^{c'}$ and $R^{d'}$ attach to the same carbon atom, then these groups may combine together with said carbon atom to form a spiro ring, or 2 or 3 groups selected from $R^{a'}$, $R^{b'}$ and $R^{c'}$ may combine to form a $C_{6-15}$ polycycloalkyl group, and n' is an integer of 1 to 5)], and the group of the formula (C') is a group of the formula:

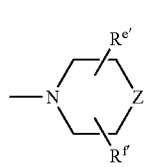

(C')

($R^{e'}$ and $R^{f'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group or a hydroxy group, or $R^{e'}$ and $R^{f'}$ attach to the same carbon atom, then these groups may combine together with said carbon atom to form a spiro ring, and Z is a carbon atom, an oxygen atom or a sulfur atom), $R^{5'}$ is a hydrogen atom, a halogen atom, a $C_{1-3}$ alkyl group, a trifluoromethyl group, a $C_{1-3}$ alkoxy group, a trifluoromethoxy group or an aryl group, or $R^{4'}$ and $R^{5'}$ may combine together with the benzene ring to which they bond, and form a tetralone ring or an indole ring, which is substituted by one group selected from a $C_{1-8}$ alkyl, an aryl-$C_{1-3}$ alkyl, a $C_{3-7}$ cycloalkyl-$C_{1-3}$ alkyl, an arylsulfonyl, a $C_{1-8}$ alkylidene, a $C_{1-8}$ alkenylidene, an aryl-$C_{1-3}$ alkylidene and a $C_{3-7}$ cycloalkyl-$C_{1-3}$ alkylidene, or a pharmaceutically acceptable salt thereof, or a hydrate or solvate thereof.

3. An N-arylphenylacetamide derivative of the formula (Ia):

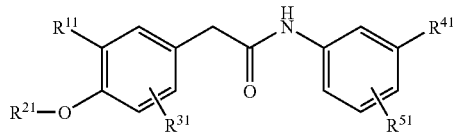

(Ia)

wherein $R^{11}$ is a $C_{1-4}$ alkoxy group, a hydroxy group, a halogen atom, a nitro group, an amino group, a $C_{1-6}$ alkylsulfonylamino group or an arylsulfonylamino group, $R^{21}$ is a hydrogen atom, a $C_{1-6}$ alkylcarbonyl group, an arylcarbonyl group or $-(CH_2)_2-N(R^{62})(R^{72})$, in which $R^{62}$ is a hydrogen atom, a $C_{1-3}$ alkyl group, a hydroxy-$C_{2-3}$ alkyl group, an amino-$C_{2-3}$ alkyl group, a formyl group, or an aryl-$C_{1-3}$ alkyloxycarbonyl group, $R^{72}$ is a hydrogen atom, a $C_{1-3}$ alkyl group, a hydroxy-$C_{2-3}$ alkyl group or an amino-$C_{2-3}$ alkyl group, $R^{31}$ is a hydrogen atom, a halogen atom, a $C_{1-4}$ alkyl group or an aryl group, $R^{41}$ is a $C_{6-10}$ alkyl group; a monocyclic group or a polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, a trifluoroethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl and carboxyl; a $C_{5-7}$ cycloalkenyl group which may optionally be substituted by 1 to 4 atoms or groups selected from a $C_{1-6}$ alkyl, a $C_{3-7}$ cycloalkyl, a fluorine, a trifluoromethyl, an aryl, a $C_{1-3}$ alkoxy and a hydroxy; a group of the formula (B'):

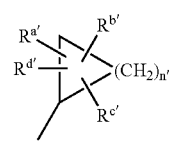

(B')

($R^{a'}$, $R^{b'}$, $R^{c'}$ and $R^{d'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group or a hydroxy group, or when $R^{a'}$ and $R^{b'}$ attach to the same carbon atom, then these groups may combine to form an oxo group, or when $R^{c'}$ and $R^{d'}$ attach to the same carbon atom, then these groups may combine together with said carbon atom to form a spiro ring, or 2 or 3 groups selected from $R^{a'}$, $R^{b'}$ and $R^{c'}$ may combine to form a $C_{6-15}$ polycycloalkyl group, and n' is an integer of 1 to 5); or a group of the formula (C'):

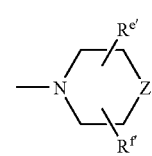

(C')

($R^{e'}$ and $R^{f'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group, or a hydroxy group, or when $R^{e'}$ and $R^{f'}$ attach to the same carbon atom, then these groups may combine together with said carbon atom to form a spiro ring, and Z is a carbon atom, an oxygen atom or a sulfur atom), $R^{51}$ is a hydrogen atom, a halogen atom, a $C_{1-3}$ alkyl group, a trifluoromethyl group, a $C_{1-3}$ alkoxy group, a trifluoromethoxy group or an aryl group, or a pharmaceutically acceptable salt thereof, or a hydrate or solvate thereof.

4. The N-arylphenylacetamide derivative according to claim 3, wherein $R^{11}$ is a methoxy group, $R^{21}$ is a hydrogen atom, an acetyl group, an ethylcarbonyl group, a propylcarbonyl group, an isopropylcarbonyl group, a butylcarbonyl group, a tert-butylcarbonyl group, a benzoyl group or a 2-aminoethyl group, $R^{31}$ is a hydrogen atom or a iodine atom, $R^{41}$ is a phenyl group, a naphthyl group, a thienyl group, a pyrrolyl group, a benzo[d]-1,3-dioxolanyl group, a benzo[b]furanyl group, a benzo[b]thiophenyl group or a dibenzo[b,d]furanyl group, which may optionally be substituted by 1 to 3 atoms or groups selected from a fluorine, a chlorine, a methyl, an ethyl, a propyl, an isopropyl, a tert-butyl, a cyclopentyl, a cyclohexyl, a trifluoromethyl, a phenyl, a fluorophenyl, a chlorophenyl, a methylphenyl, a trifluoromethylphenyl, a trifluoromethoxyphenyl, a trifluoromethoxy, a methylthio, a methoxycarbonyl, an ethoxycarbonyl, a tert-butoxycarbonyl and a carboxyl; or a cyclohexenyl group, a cyclopentyl group, a cyclohexyl group, a cycloheptyl group, a bicyclo[2,2,2]octyl group, an adamantyl group, a 1-piperidinyl group, a 7-azaspiro[4,5]decan-7-yl group, a 2-azaspiro[5,5]-undecan-2-yl group, a 1-azaspiro[5,5]undecan-1-yl group, a 4-morpholinyl group, a 4-thiomorpholinyl group or a 1-oxa-4-azaspiro-[5,5]undecan-4-yl group, which may optionally be substituted by 1 to 4 atoms or groups selected from a methyl, an ethyl, a propyl, an isopropyl, a tert-butyl, a cyclopentyl, a cyclohexyl, a fluorine, a trifluoromethyl, a phenyl, a fluorophenyl, a chlorophenyl, a methylphenyl, a trifluoromethylphenyl and a trifluoromethoxyphenyl, $R^{51}$ is a hydrogen atom, a fluorine atom, a methyl group, a trifluoromethyl group, a methoxy group, a trifluoromethoxy group or a phenyl group, or a pharmaceutically acceptable salt thereof, or a hydrate or solvate thereof.

5. An N-arylphenylacetamide derivative of the formula (Ib):

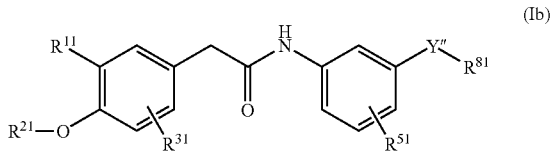

wherein $R^{11}$ is a $C_{1-4}$ alkoxy group, a hydroxy group, a halogen atom, a nitro group, an amino group, a $C_{1-6}$ alkylsulfonylamino group, or an arylsulfonylamino group, $R^{21}$ is a hydrogen atom, a $C_{1-6}$ alkylcarbonyl group, an arylcarbonyl group or —(CH$_2$)$_2$—N(R$^{62}$)(R$^{72}$), in which $R^{62}$ is a hydrogen atom, a $C_{1-3}$ alkyl group, a hydroxy-$C_{2-3}$ alkyl group, an amino-$C_{2-3}$ alkyl group, a formyl group, or an aryl-$C_{1-3}$ alkyloxycarbonyl group, and $R^{72}$ is a hydrogen atom, a $C_{1-3}$ alkyl group, a hydroxy-$C_{2-3}$ alkyl group or an amino-$C_{2-3}$ alkyl group, $R^{31}$ is a hydrogen atom, a halogen atom, a $C_{1-4}$ alkyl group or an aryl group, Y″ is —CH$_2$—, —(CH$_2$)$_2$—, —(CH$_2$)$_3$—, —CH=CH—, —C≡C—, —CO—, —COCH$_2$—, —CO(CH$_2$)$_2$—, —COCH=CH—, —O— or —O(CH$_2$)$_2$—, $R^{81}$ is a monocyclic group or a polycyclic group consisting of a 5- or 6-membered aromatic ring containing 0 to 3 heteroatoms selected from N, O and S, which may optionally be substituted by 1 to 3 atoms or groups selected from a halogen, a $C_{1-6}$ alkyl, a $C_{3-7}$ cycloalkyl, a trifluoromethyl, a trifluoroethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl and a carboxyl; a $C_{5-7}$ cycloalkenyl group which may optionally be substituted by 1 to 4 atoms or groups selected from a $C_{1-6}$ alkyl, a $C_{3-7}$ cycloalkyl, a fluorine, a trifluoromethyl, an aryl, a $C_{1-3}$ alkoxy and a hydroxy; or a group of the formula (B'):

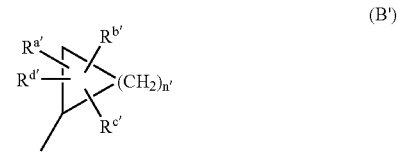

($R^{a'}$, $R^{b'}$, $R^{c'}$ and $R^{d'}$ are the same or different and each is a hydrogen atom, a $C_{1-6}$ alkyl group, a $C_{3-7}$ cycloalkyl group, a fluorine atom, a trifluoromethyl group, an aryl group, a $C_{1-3}$ alkoxy group or a hydroxy group, or when $R^{a'}$ and $R^{b'}$ attach to the same carbon atom, then these groups may combine to form an oxo group, or when $R^{c'}$ and $R^{d'}$ attach to the same carbon atom, then these groups may combine together with said carbon atom to form a spiro ring, or 2 or 3 groups selected from $R^{a'}$, $R^{b'}$ and $R^{c'}$ may combine to form a $C_{6-15}$ polycycloalkyl group, and n' is an integer of 1 to 5), $R^{51}$ is a hydrogen atom, a halogen atom, a $C_{1-3}$ alkyl group, a trifluoromethyl group, a $C_{1-3}$ alkoxy group, a trifluoromethoxy group or an aryl group, or a pharmaceutically acceptable salt thereof, or a hydrate or solvate thereof.

6. The N-arylphenylacetamide derivative according to claim 5, wherein $R^{11}$ is a methoxy group, $R^{21}$ is a hydrogen atom, an acetyl group, an ethylcarbonyl group, a propylcarbonyl group, an isopropylcarbonyl group, a butylcarbonyl group, a tert-butylcarbonyl group, a benzoyl group, a 2-aminoethyl group, $R^{31}$ is a hydrogen atom or a iodine atom, Y″ is —(CH$_2$)$_2$—, —CH=CH—, —C≡C—, —O— or —O(CH$_2$)$_2$—, $R^{81}$ is a phenyl group, a naphthyl group or a thienyl group, which may optionally be substituted by 1 to 3 atoms or groups selected from a fluorine, a chlorine, a methyl, an ethyl, a propyl, an isopropyl, a tert-butyl, a cyclopentyl, a cyclohexyl, a trifluoromethyl, a phenyl, a fluorophenyl, a chlorophenyl, a methylphenyl, a trifluoromethylphenyl, a trifluoromethoxyphenyl, a trifluoromethoxy, a methylthio and a methoxycarbonyl; or a cyclohexenyl group, a cyclopentyl group, a cyclohexyl group, a cycloheptyl group, a bicyclo[2,2,2]octyl group or an adamantyl group, which may optionally be substituted by 1 to 4 atoms or groups selected from a methyl, an ethyl, a propyl, an isopropyl, a tert-butyl, a cyclopentyl, a cyclohexyl, a fluorine, a trifluoromethyl, a phenyl, a fluorophenyl, a chlorophenyl, a methylphenyl, a trifluoromethylphenyl and a trifluoromethoxyphenyl, $R^{51}$ is a hydrogen atom, a fluorine atom, a methyl group, a trifluoromethyl group, a methoxy group, a trifluoromethoxy group or a phenyl group, or a pharmaceutically acceptable salt thereof, or a hydrate or solvate thereof.

7. An N-arylphenylacetamide derivative of the formula (Ic):

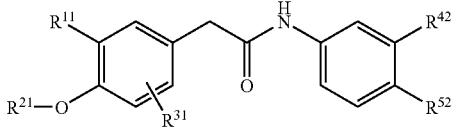

wherein $R^{11}$ is a $C_{1-4}$ alkoxy group, a hydroxy group, a halogen atom, a nitro group, an amino group, a $C_{1-6}$ alkylsulfonylamino group or an arylsulfonylamino group, $R^{21}$ is a hydrogen atom, a $C_{1-6}$ alkylcarbonyl group, an arylcarbonyl group or —$(CH_2)_2$—$N(R^{62})(R^{72})$, in which $R^{62}$ is a hydrogen atom, a $C_{1-3}$ alkyl group, a hydroxy-$C_{2-3}$ alkyl group, an amino-$C_{2-3}$ alkyl group, a formyl group or an aryl-$C_{1-3}$ alkyloxycarbonyl group, and $R^{72}$ is a hydrogen atom, a $C_{1-3}$ alkyl group, a hydroxy-$C_{2-3}$ alkyl group or an amino-$C_{2-3}$ alkyl group, $R^{31}$ is a hydrogen atom, a halogen atom, a $C_{1-4}$ alkyl group or an aryl group, $R^{42}$ and $R^{52}$ may combine together with the benzene ring to which they bond to form a group selected from the following group:

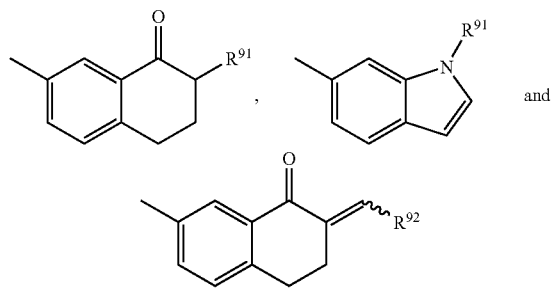

($R^{91}$ is a $C_{1-8}$ alkyl group; an aryl-$C_{1-3}$ alkyl group; a $C_{3-7}$ cycloalkyl-$C_{1-3}$ alkyl group; or an arylsulfonyl group, $R^{92}$ is a $C_{1-7}$ alkyl group; a $C_{1-7}$ alkenyl group; a phenyl group which may optionally be substituted by 1 to 3 atoms or groups selected from a halogen, a $C_{1-6}$ alkyl, a $C_{3-7}$ cycloalkyl, a trifluoromethyl, a trifluoroethyl, an aryl, an aryl-$C_{1-3}$ alkyl, a $C_{1-3}$ alkoxy, a trifluoromethoxy, an aryloxy, a $C_{1-3}$ alkylcarbonyl, a $C_{3-7}$ cycloalkylcarbonyl, a nitro, a cyano, a hydroxy, a $C_{1-3}$ alkylthio, a $C_{1-4}$ alkoxycarbonyl-$C_{1-3}$ alkyl, a carboxy-$C_{1-3}$ alkyl, a $C_{1-4}$ alkoxycarbonyl and a carboxyl; an aryl-$C_{1-2}$ alkyl group; a $C_{3-7}$ cycloalkyl group; or a $C_{3-7}$ cycloalkyl-$C_{1-2}$ alkyl group), or a pharmaceutically acceptable salt thereof, or a hydrate or solvate thereof.

8. The N-arylphenylacetamide derivative according to claim 7, wherein $R^{11}$ is a methoxy group, $R^{21}$ is a hydrogen atom, an acetyl group, an ethylcarbonyl group, a propylcarbonyl group, an isopropylcarbonyl group, a butylcarbonyl group, a tert-butylcarbonyl group, a benzoyl group, a 2-aminoethyl group, $R^{31}$ is a hydrogen atom or a iodine atom, $R^{42}$ and $R^{52}$ may combine together with the benzene ring to which they bond to form a group selected from the following group:

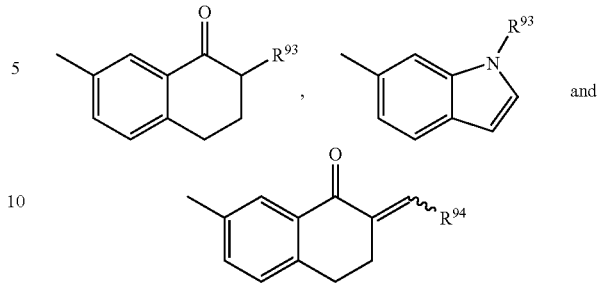

($R^{93}$ is a butyl group, a pentyl group, a hexyl group, an isobutyl group, a heptyl group, or a benzyl group, a phenethyl group or a phenylpropyl group, wherein the benzene ring moiety may optionally be substituted by 1 to 3 atoms or groups selected from a fluorine, a chlorine, a methyl, an ethyl, a propyl, an isopropyl, a tert-butyl, a cyclohexyl, a trifluoromethyl, a phenyl, a fluorophenyl, a chlorophenyl, a methylphenyl, a trifluoromethylphenyl, a trifluoromethoxyphenyl, a trifluoromethoxy, a methylthio and a methoxycarbonyl, and $R^{94}$ is an isopropyl group, or a phenyl group which may optionally be substituted by 1 to 3 atoms or groups selected from a fluorine, a chlorine, a methyl, an ethyl, a propyl, an isopropyl, a tert-butyl, a cyclohexyl, a trifluoromethyl, a phenyl, a fluorophenyl, a chlorophenyl, a methylphenyl, a trifluoromethylphenyl, a trifluoromethoxyphenyl, a trifluoromethoxy, a methylthio and a methoxycarbonyl), or a pharmaceutically acceptable salt thereof, or a hydrate or solvate thereof.

9. The N-arylphenylacetamide derivative according to claim 1, wherein $R^2$ is a hydrogen atom, or a pharmaceutically acceptable salt thereof, or a hydrate or solvate thereof.

10. The N-arylphenylacetamide derivative according to claim 1, wherein $R^2$ is a $C_{1-6}$ alkylcarbonyl group or an arylcarbonyl group, or a pharmaceutically acceptable salt thereof, or a hydrate or solvate thereof.

11. The N-arylphenylacetamide derivative according to claim 1, wherein $R^2$ is —$(CH_2)_2$—$N(R^6)(R^7)$, or a pharmaceutically acceptable salt thereof, or a hydrate or solvate thereof.

12. The N-arylphenylacetamide derivative according to claim 1, wherein $R^2$ is —$(CH_2)_m OH$ or —$(CH_2)_q COOH$, or a pharmaceutically acceptable salt thereof, or a hydrate or solvate thereof.

13. An N-arylphenylacetamide derivative selected from the following compounds:

N-(3-cyclohexylphenyl)-4-hydroxy-3-methoxyphenylacetamide,

N-[3-(adamantan-2-yl)phenyl]-4-hydroxy-3-methoxyphenylacetamide,

N-(3-cyclopentylphenyl)-4-hydroxy-3-methoxyphenylacetamide,

N-[3-(cyclohexylmethyl) phenyl]-4-hydroxy-3-methoxyphenylacetamide,

N-[3-(cyclohexen-1-yl)phenyl]-4-hydroxy-3-methoxyphenylacetamide, 4-hydroxy-3-methoxy-N-[3-(2-phenylcyclohexan-1-yl)phenyl]-phenylacetamide, 4-hydroxy-3-methoxy-N-[3-(4-methylcyclohexan-1-yl)phenyl]-phenylacetamide, N-[3-(4-tert-butylcyclohexan-1-yl)phenyl]-4-hydroxy-3-methoxyphenylacetamide, 4-hydroxy-3-methoxy-N-(3-phenylphenyl)phenylacetamide, 4-hydroxy-3-methoxy-N-[3-(2-phenylethynyl)phenyl]phenylacetamide, 4-hydroxy-3-methoxy-N-[3-(2-phenylethyl) phenyl]phenylacetamide, 4-hydroxy-3-methoxy-N-[3-[(Z)-2-phenylvinyl]phenyl]phenylacetamide, 4-(2-aminoethoxy)-3-methoxy-N-[3-(2-phenylethyl)phenyl]phenylacetamide, 4-(2-aminoethoxy)-N-(3-cyclohexylphenyl)-3-methoxyphenylacetamide, 4-(2-aminoethoxy)-N-[3-(4-tert-butylcyclohexan-1-yl)phenyl]-3-methoxyphenylacetamide, 4-(2-aminoethoxy)-3-methoxy-N-(3-phenylphenyl)phenylacetamide, 4-(2-aminoethoxy)-N-[3-(3-fluorophenyl)phenyl]-3-methoxyphenylacetamide, 4-(2-aminoethoxy)-N-[3-(4-chlorophenyl)phenyl]-3-methoxyphenylacetamide, 4-acetoxy-N-[3-(4-tert-butylcyclohexan-1-yl)phenyl]-3-methoxyphenylacetamide, 4-benzoyloxy-N-[3-(4-tert-butylcyclohexan-1-yl)phenyl]-3-methoxyphenylacetamide, 4-tert-butylcarbonyloxy-N-[3-(4-tert-butylcyclohexan-1-yl)phenyl]-3-methoxyphenylacetamide, N-[3-(4-tert-butylcyclohexen-1-yl)phenyl]-4-hydroxy-3-methoxyphenylacetamide, 4-hydroxy-3-methoxy-N-[3-(4-trifluoromethylcyclohexan-1-yl)-phenyl]phenylacetamide, 4-hydroxy-3-methoxy-N-[3-(3-methylcyclohexan-1-yl)phenyl]-phenylacetamide, N-[3-(2,6-dimethylcyclohexan-1-yl)phenyl]-4-hydroxy-3-methoxyphenylacetamide, N-[3-(3,5-dimethylcyclohexan-1-yl)phenyl]-4-hydroxy-3-methoxyphenylacetamide, N-[3-(4-tert-butylpiperidin-1-yl)phenyl]-4-hydroxy-3-methoxyphenylacetamide, N-[3-(3-cyclohexylpiperidin-1-yl)phenyl]-4-hydroxy-3-methoxyphenylacetamide, N-[3-(3-methylpiperidin-1-yl)phenyl]-4-hydroxy-3-methoxyphenylacetamide, N-[3-(4-tert-butylcyclohexan-1-yl)phenyl]-4-hydroxy-5-iodo-3-methoxyphenylacetamide, 4-hydroxy-3-methoxy-N-[3-(2-chlorothiophen-5-yl)phenyl]-phenylacetamide, 4-hydroxy-3-methoxy-N-[3-(1-tert-butoxycarbonylpyrrol-2-yl)-phenyl]phenylacetamide, 4-hydroxy-3-methoxy-N-[3-(2-cyclohexylethyl)phenyl]phenylacetamide, 4-(2-aminoethoxy)-N-[3-(2-cyclohexylphenyl)phenyl]-3-methoxyphenylacetamide, 4-(2-aminoethoxy)-N-[3-(2-fluorophenyl)phenyl]-3-methoxyphenylacetamide, 4-(2-aminoethoxy)-N-[3-(4-fluorophenyl)phenyl]-3-methoxyphenylacetamide, 4-(2-aminoethoxy)-N-[3-(2-chlorophenyl)phenyl]-3-methoxyphenylacetamide, 4-(2-aminoethoxy)-N-[3-(3-chlorophenyl)phenyl]-3-methoxyphenylacetamide, 4-(2-aminoethoxy)-N-[3-(3,5-difluorophenyl)phenyl]-3-methoxyphenylacetamide, 4-(2-aminoethoxy)-3-methoxy-N-[3-(2-methylphenyl)phenyl]-phenylacetamide, 4-(2-aminoethoxy)-3-methoxy-N-[3-(2,4,6-trimethylphenyl)phenyl]-phenylacetamide, 4-(2-aminoethoxy)-N-[3-(3-isopropylphenyl)phenyl]-3-methoxyphenylacetamide, 4-(2-aminoethoxy)-3-methoxy-N-[3-(4-trifluoromethylphenyl)-phenyl]phenylacetamide, 4-(2-aminoethoxy)-3-methoxy-N-[3-(2-trifluoromethylphenyl)-phenyl]phenylacetamide, 4-(2-aminoethoxy)-3-methoxy-N-[3-(2-phenylphenyl)phenyl]-phenylacetamide, 4-(2-aminoethoxy)-3-methoxy-N-[3-(3-phenylphenyl)phenyl]phenylacetamide, 4-(2-aminoethoxy)-N-[3-(3-methoxycarbonylphenyl)phenyl]-3-methoxyphenylacetamide, 4-(2-aminoethoxy)-3-methoxy-N-[3-(3-trifluoromethoxyphenyl)-phenyl]phenylacetamide, 4-(2-aminoethoxy)-3-methoxy-N-[3-(2-methylthiophenyl)phenyl]-phenylacetamide, 4-(2-aminoethoxy)-3-methoxy-N-[3-(thiophen-3-yl)phenyl]-phenylacetamide, 4-(2-aminoethoxy)-3-methoxy-N-[3-(naphthalen-1-yl)phenyl]-phenylacetamide, 4-(2-aminoethoxy)-N-[3-(2H-benzo[d]-1,3-dioxolan-5-yl)phenyl]-3-methoxyphenylacetamide, 4-(2-aminoethoxy)-N-[3-(benzofuran-2-yl)phenyl]-3-methoxyphenylacetamide, 4-(2-aminoethoxy)-N-[3-(3-tert-butylphenyl)phenyl]-3-methoxyphenylacetamide, 4-(2-aminoethoxy)-N-[(2-fluoro-5-phenyl)phenyl]-3-methoxyphenylacetamide, 4-(2-aminoethoxy)-N-[(2-methoxy-3-fluoro-5-phenyl)phenyl]-3-methoxyphenylacetamide, 4-(2-aminoethoxy)-N-[(2-methyl-5-phenyl)phenyl]-3-methoxyphenylacetamide, 4-(2-aminoethoxy)-3-methoxy-N-[(3-phenyl-4-methyl)phenyl]-phenylacetamide, 4-(2-aminoethoxy)-3-methoxy-N-[(2-methoxy-5-phenyl)phenyl]-phenylacetamide, 4-(2-aminoethoxy)-3-methoxy-N-[(3-trifluoromethyl-5-phenyl)-phenyl]phenylacetamide, 4-(2-aminoethoxy)-3-methoxy-N-[(3-phenyl-4-trifluoromethoxy)-phenyl]phenylacetamide, 4-(2-aminoethoxy)-3-methoxy-N-[(4-methyl-3,5-diphenyl)phenyl]-phenylacetamide, 4-(2-aminoethoxy)-N-[3-(3-cyclohexylphenyl)phenyl]-3-methoxyphenylacetamide, 4-(2-aminoethoxy)-N-[3-(2-tert-butylphenyl)phenyl]-3-methoxyphenylacetamide, 4-(2-aminoethoxy)-3-methoxy-N-[3-(3-phenoxyphenyl)phenyl]-phenylacetamide, 4-(2-aminoethoxy)-3-methoxy-N-[3-(2-phenylethyloxy)phenyl]-phenylacetamide, 4-(2-aminoethoxy)-N-[3-[(cis)-4-tert-butylcyclohexan-1-yl]phenyl]-3-methoxyphenylacetamide, 4-(2-aminoethoxy)-N-[3-[(trans)-4-tert-butylcyclohexan-1-yl]-phenyl]-3-methoxyphenylacetamide, 4-(2-aminoethoxy)-3-methoxy-N-[3-(piperidin-1-yl)phenyl]phenylacetamide, 4-(2-aminoethoxy)-N-[3-(3-cyclohexylpiperidin-1-yl)phenyl]-3-methoxyphenylacetamide, 4-(2-aminoethoxy)-3-methoxy-N-[3-(3-phenylpiperidin-1-yl)-phenyl]phenylacetamide, 4-(2-aminoethoxy)-3-methoxy-N-[3-(2-azaspiro[5,5]undecan-2-yl)-phenyl]phenylacetamide, 4-(2-aminoethoxy)-3-methoxy-N-[3-[2-(3-methylphenyl)ethyl]-phenyl]phenylacetamide, 4-(2-aminoethoxy)-3-methoxy-N-[3-[2-(2-fluorophenyl)ethyl]-phenyl]phenylacetamide, 4-(2-aminoethoxy)-3-methoxy-N-[1-oxo-2-phenylmethyl-1,2,3,4-tetrahydronaphthalen-7-yl]phenylacetamide, 4-(2-aminoethoxy)-3-methoxy-N-[1-benzylindol-6-yl]phenylacetamide, and 4-hydroxy-3-methoxy-N-[1-oxo-2-phenylmethyl-1,2,3,4-tetrahydronaphthalen-7-yl]phenylacetamide, or a pharmaceutically acceptable salt thereof, or a hydrate or solvate thereof.

14. A pharmaceutical composition, which comprises as an active ingredient the N-arylphenylacetamide derivative as set forth in any one of claims 1 to 13, or a pharmaceutically acceptable salt thereof, or a hydrate or solvate thereof.

15. An analgesic agent or an antiinflammatory agent, which comprises as an active ingredient the N-arylphenylacetamide derivative as set forth in any one of claims 1 to 13, or a pharmaceutically acceptable salt thereof, or a hydrate or solvate thereof.

16. A method for treatment of pain or inflammation, which comprises administering an effective amount of the N-arylphenylacetamide derivative as set forth in any one of claims 1 to 13, or a pharmaceutically acceptable salt thereof, or a hydrate or solvate thereof, to a patient having a pain or an inflammation.

* * * * *